US012799102B2

(12) United States Patent
Zhang et al.

(10) Patent No.: US 12,799,102 B2
(45) Date of Patent: Nov. 17, 2026

(54) TRIAZINE DIONE DERIVATIVE, PREPARATION METHOD THEREFOR AND APPLICATION THEREOF IN MEDICINE

(71) Applicant: Jiangsu Hengrui Pharmaceuticals Co., Ltd., Lianyungang (CN)

(72) Inventors: Xiaomin Zhang, Shanghai (CN); Weimin Hu, Shanghai (CN); Hongbo Fei, Shangai (CN); Feng He, Shanghai (CN); Weikang Tao, Shanghai (CN)

(73) Assignee: JIANGSU HENGRUI PHARMACEUTICALS CO., LTD., Lianyungang (CN)

( * ) Notice: Subject to any disclaimer, the term of this patent is extended or adjusted under 35 U.S.C. 154(b) by 571 days.

(21) Appl. No.: 18/253,704

(22) PCT Filed: Nov. 19, 2021

(86) PCT No.: PCT/CN2021/131642

§ 371 (c)(1),
(2) Date: May 19, 2023

(87) PCT Pub. No.: WO2022/105852

PCT Pub. Date: May 27, 2022

(65) Prior Publication Data

US 2024/0010639 A1 Jan. 11, 2024

(30) Foreign Application Priority Data

Nov. 20, 2020 (CN) ......................... 202011310827.4
Jan. 8, 2021 (CN) ......................... 202110021509.4
Mar. 5, 2021 (CN) ......................... 202110244090.9
Apr. 28, 2021 (CN) ......................... 202110464375.3

(51) Int. Cl.

*C07D 405/12* (2006.01)
*A61P 9/00* (2006.01)
*C07D 251/46* (2006.01)
*C07D 401/12* (2006.01)
*C07D 405/04* (2006.01)

(52) U.S. Cl.

CPC .............. *C07D 405/12* (2013.01); *A61P 9/00* (2018.01); *C07D 251/46* (2013.01); *C07D 401/12* (2013.01); *C07D 405/04* (2013.01)

(58) Field of Classification Search

CPC .. C07D 405/12; C07D 251/46; C07D 401/12; C07D 405/04; C07D 405/14; A61P 9/00; A61P 9/04; A61P 9/10; Y02A 50/30; A61K 31/53

See application file for complete search history.

(56) References Cited

U.S. PATENT DOCUMENTS 3,959,469 A 5/1976 Kay
4,254,122 A 3/1981 Brown
9,181,200 B2 11/2015 Oslob et al.
RE50,050 E 7/2024 Oslob et al.
2006/0205685 A1 9/2006 Phiasivongsa et al.
2011/0319400 A1* 12/2011 Flores ..................... A61P 25/02 514/227.8
2011/0319414 A1* 12/2011 Kai ...................... C07D 413/12 544/212
2013/0172317 A1 7/2013 Kai et al.
2014/0378464 A1* 12/2014 Oslob ................. A61K 31/513 544/312
2014/0378491 A1 12/2014 Oslob et al.
2016/0176868 A1 6/2016 Oslob et al.
2020/0048257 A1 2/2020 Masuda et al.
2022/0089551 A1 3/2022 Shao
2024/0262804 A1* 8/2024 Zhu ...................... C07D 405/12
2025/0326743 A1 10/2025 Zhang et al.

FOREIGN PATENT DOCUMENTS

CA 1036491 A 8/1978
CN 105473576 A 4/2016
CN 110698415 A 1/2020
CN 111116492 A 5/2020
GB 1435585 A 5/1976
GB 1599518 A 10/1981

(Continued)

OTHER PUBLICATIONS

Wermuth (“The Practice of Medicinal Chemistry”, 4th ed. (2015), Ch. 8, pp. 181-241 provided). (Year: 2015).*

(Continued)

*Primary Examiner* — Robert H Havlin

(74) *Attorney, Agent, or Firm* — WILSON SONSINI GOODRICH & ROSATI

(57) ABSTRACT

Provided are a triazine dione derivative, a preparation method therefor and an application thereof in medicine. Specifically, provided are a triazine dione derivative represented by general formula (I), a preparation method therefor, a pharmaceutical composition containing the derivative and a use thereof as a therapeutic agent, particularly a use in preparing a myosin inhibitor and a use in preparing a drug for treating hypertrophic cardiomyopathy (HCM) or heart diseases having pathophysiological features related to HCM.

(I)

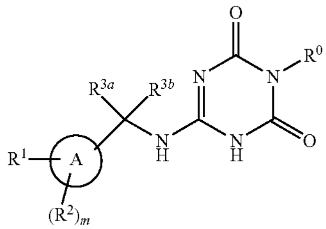

2 Claims, No Drawings

(56) References Cited

FOREIGN PATENT DOCUMENTS

| | | | |
|---|---|---|---|
| JP | S54154779 | A | 12/1979 |
| JP | 2006524668 | A | 11/2006 |
| JP | 2019182806 | A | 10/2019 |
| JP | 2019182865 | A | 10/2019 |
| WO | WO-2010040661 | A1 | 4/2010 |
| WO | WO-2012020749 | A1 | 2/2012 |
| WO | 2014205223 | A1 | 12/2014 |
| WO | 2014205234 | A1 | 12/2014 |
| WO | WO-2018074390 | A1 | 4/2018 |
| WO | WO-2019028360 | A1 | 2/2019 |
| WO | 2020047447 | A1 | 3/2020 |
| WO | 2020092208 | A1 | 5/2020 |
| WO | 2020151605 | A1 | 7/2020 |
| WO | WO-2022105852 | A1 | 5/2022 |
| WO | WO-2022194236 | A1 | 9/2022 |
| WO | WO-2023222103 | A1 | 11/2023 |

OTHER PUBLICATIONS

International Search Report and Written Opinion for International Application No. PCT/CN2021/131642, filed Nov. 19, 2021, mailed Feb. 15, 2022.
Chuang, Chihyuan et al. Discovery of aficamten (CK-274), a next-generation cardiac myosin inhibitor for the treatment of hypertrophic cardiomyopathy. Journal of medicinal chemistry 64(19):14142-14152 (2021).
Frey, Norbert et al. Mechanisms of disease: hypertrophic cardiomyopathy. Nature Reviews Cardiology 9(2):91-100 (2012).
Green, Eric M. et al. A small-molecule inhibitor of sarcomere contractility suppresses hypertrophic cardiomyopathy in mice. Science 351(6273):617-621 (2016).
Kai, Hiroyuki et al. Dioxotriazine derivatives as a new class of P2X3 receptor antagonists: Identification of a lead and initial SAR studies. Bioorg Med Chem Lett 37:127833, 1-7 (2021).
Kawas, Raja F. et al. A small-molecule modulator of cardiac myosin acts on multiple stages of the myosin chemomechanical cycle. Journal of Biological Chemistry 292(40):16571-16577 (2017).
Kiefer, Karin et al. New relevant pesticide transformation products in groundwater detected using target and suspect screening for agricultural and urban micropollutants with LC-HRMS. Water Research 165:114972, 1-11 (2019).
Kong, Kah Hoe et al. A Versatile Thiouronium-Based Solid-Phase Synthesis of 1, 3, 5-Triazines. Chemistry A European Journal 18(5):1476-1486 (2012).
Meena, Chhuttan L. et al. Triazine-Based Janus G-C Nucleobase as a Building Block for Self-Assembly, Peptide Nucleic Acids, and Smart Polymers. J Org Chem 86(4):3186-3195 (2021).
PCT/CN2021/131642 International Preliminary Report on Patentability dated Jun. 1, 2023.
PCT/CN2022/081361 International Preliminary Report on Patentability dated Sep. 28, 2023.
PCT/CN2022/081361 International Search Report and Written Opinion dated Jun. 21, 2022.
PCT/CN2023/095172 International Preliminary Report on Patentability dated Dec. 5, 2024.
PCT/CN2023/095172 International Search Report and Written Opinion dated Sep. 1, 2023.
Piskala, Alois et al. Synthesis, molecular conformation and biological activity of 6-amino-5-azacytidine. Collection of Czechoslovak chemical communications 54(9):2502-2512 (1989).
Sommese, Ruth F. et al. Molecular consequences of the R453C hypertrophic cardiomyopathy mutation on human-cardiac myosin motor function. PNAS USA 110(31):12607-12612 (2013).
STN 1998650-16-0 (entered Sep. 23, 2016) (pp. 1-2).
Tower-Rader, Albree et al. Mavacamten: a novel small molecule modulator of beta-cardiac myosin for treatment of hypertrophic cardiomyopathy. Expert Opin Investig Drugs 29(11):1171-1178 (2020).
Yu, Yongping et al. A traceless approach for the solid-phase synthesis of 6-amino-1, 3, 5-triazine-2, 4-diones. Journal of Combinatorial Chemistry 6(1):83-85 (2004).
Kay, Ian T. et al. 1,3,5-Triazine-2,6-dione and pharmaceutical compositions containing it CAS:98:34604 (1983).
U.S. Appl. No. 18/550,666 Office Action dated Jan. 13, 2026.
Pochet, S. et al. Amino-4 Dihydroxy-2, 6 (Desoxy-2-D-ribofurannosyl)-1-s-Triazines. Nucleosides and Nucleotides 5(2):153-157 (1986) (English Abstract).
U.S. Appl. No. 18/550,666 Office Action dated May 21, 2026.

* cited by examiner

TRIAZINE DIONE DERIVATIVE, PREPARATION METHOD THEREFOR AND APPLICATION THEREOF IN MEDICINE

CROSS-REFERENCE TO RELATED APPLICATIONS

This is the U.S. national stage application, filed under 35 U.S.C. § 371, of International Patent Application No. PCT/CN2021/131642, filed on Nov. 19, 2021, which claims the benefit and priority of Chinese patent application No. 202011310827.4, filed on Nov. 20, 2020, No. 202110021509.4, filed on Jan. 8, 2021, No. 202110244090.9, filed on Mar. 5, 2021, and No. 202110464375.3, filed on Apr. 28, 2021, with the China National Intellectual Property Administration (CNIPA), the disclosures of all of which are hereby incorporated by reference in their entireties.

TECHNICAL FIELD

The present disclosure is in the field of pharmaceutics and relates to a triazine dione derivative, a preparation method therefor and pharmaceutical use thereof. In particular, the present disclosure relates to a triazine dione derivative of general formula (I), a preparation method therefor and a pharmaceutical composition comprising the derivative, as well as use thereof in preparing a myosin inhibitor and in preparing a medicament for treating hypertrophic cardiomyopathy (HCM) or heart diseases with HCM-related pathophysiological characteristics.

BACKGROUND

Hypertrophic cardiomyopathy (HCM) is a dominant hereditary cardiomyopathy associated with genetic mutations. Its global incidence is about 0.2%. It is the biggest cause of sudden death in young people under 35 (C. Vaughan Tuohy, et al., European Journal of Heart Failure, 22, 2020, 228-240). Clinically, it is characterized by asymmetric left ventricular wall hypertrophy, typical thickening of ventricular septum, reduced ventricular cavity size, obstructed left ventricular blood filling, and decreased ventricular diastolic compliance. The disease is classified into obstructive and non-obstructive hypertrophic cardiomyopathy according to the presence or absence of obstruction in the outflow tract of the left ventricle. In clinical practice, β-blockers and calcium channel blockers are commonly used to reduce cardiac contraction and relieve symptoms in the treatment of hypertrophic cardiomyopathy. However, all of these treatments are targeted at the symptoms rather than the root cause. When HCM becomes advanced, the patient has to have a heart transplant (Radhakrishnan Ramaraj, Cardiology in Review, 16(4), 2008, 172-180). Therefore, it is very urgent to find a treatment targeted at the root cause of HCM.

Research has found that 70% of HCM cases are caused by mutations in the sarcomeric protein genes. Multiple site mutations are found in 5-7% of patients. More than 70 pathogenic mutations have been identified, but most of them are family-specific, and only a few hotspots are identified, e.g., MYH7 R403Q and R453C mutations (Norbert Frey, et al., Nature Reviews Cardiology, 9, 2011, 91-100; M. Sabater-Molina, et al., Clinical Genetics, 93, 2018, 3-14). A study on the pathogenic probability of genetic mutation reveals that about 30% of patients contain mutations in the MYH7 gene. MYH7 causes early onset of disease and more severe myocardial hypertrophy than other sarcomeric protein genes. Myosin is the constituent of thick filaments in myofibrils and plays an important role in the motion of muscles. The molecule takes the shape of a beansprout and consists of two heavy chains and several light chains. The myosin heads bind actin to form cross-bridges, which greatly increase the ATPase activity of myosin. Myosin catalyzes ATP hydrolysis and the energy produced causes the cross-bridges to slide and thus muscle contraction. Research findings show that the MYH7 gene results in an increase in the ATPase activity of myosin, a decrease in the proportion of the super-relaxed state (SRX) of myosin, and more cross-bridges between myosin and actin, and thus abnormal systolic function (Eric M. Green, et al., Science, 351(6273), 2016, 617-621; Ruth F. Sommese, et al., Proceedings of the National Academy Sciences, 110(31), 2013, 12607-12612). Myosin is therefore an important target for the treatment of hypertrophic cardiomyopathy.

Disclosed patent applications of myosin inhibitors include WO2014205223A1, WO2014205234A1, WO2019028360A1, WO2020092208A1, CN110698415A, etc.

SUMMARY

The present disclosure aims to provide a compound of general formula (I) or a pharmaceutically acceptable salt thereof:

(I)

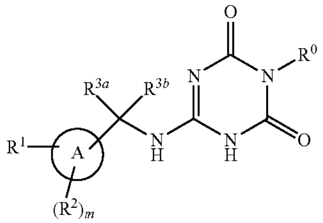

wherein:

ring A is selected from the group consisting of cycloalkyl, heterocyclyl, aryl and heteroaryl, $R^1$ is selected from the group consisting of halogen, alkyl, alkenyl, alkynyl, alkoxy, haloalkyl, haloalkoxy, cyano, amino, nitro, hydroxy, hydroxyalkyl, $C(O)R^6$, $C(O)OR^7$, $S(O)_tR^8$, $S(O)_tNR^9R^{10}$, $C(O)NR^9R^{10}$, $NR^9R^{10}$ and

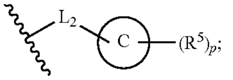

$R^2$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, $C(O)R^6$, $C(O)OR^7$, $S(O)_tR^8$, $S(O)_tNR^9R^{10}$, $C(O)NR^9R^{10}$ and $NR^9R^{10}$;

alternatively, $R^1$ and one adjacent $R^2$, or two adjacent $R^2$, fuse with ring A to form cycloalkyl or heterocyclyl, wherein the cycloalkyl or heterocyclyl is optionally substituted with one or more substituents selected from the group consisting of a hydrogen atom, halogen, alkyl, haloalkyl, alkoxy, haloalkoxy, cyano, amino, nitro and hydroxy;

$L_2$ is selected from the group consisting of a covalent bond, $(CH_2)_r$, C(O), $NR^a$, an oxygen atom and a sulfur atom;

$R^a$ is selected from the group consisting of a hydrogen atom, alkyl, haloalkyl, hydroxyalkyl, cycloalkyl, heterocyclyl, aryl and heteroaryl;

ring C is selected from the group consisting of cycloalkyl, heterocyclyl, aryl and heteroaryl;

$R^5$ are identical or different and are each independently selected from the group consisting of a hydrogen atom, halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl;

$R^{3a}$ is selected from the group consisting of halogen, alkyl, alkenyl, alkynyl, alkoxy, haloalkyl, haloalkoxy, cyano, amino, nitro, hydroxy, hydroxyalkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkoxy, haloalkoxy, cyano, amino, nitro and hydroxy;

$R^{3b}$ is a hydrogen atom;

$R^0$ is alkyl or

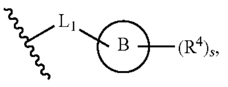

wherein the alkyl is optionally substituted with one or more substituents selected from the group consisting of halogen, alkoxy, haloalkoxy, cyano, amino, nitro and hydroxy;

$L_1$ is a covalent bond or $(CH_2)_r$;

ring B is selected from the group consisting of cycloalkyl, heterocyclyl, aryl and heteroaryl;

$R^4$ are identical or different and are each independently selected from the group consisting of a hydrogen atom, halogen, alkyl, alkenyl, alkynyl, alkoxy, haloalkyl, haloalkoxy, oxo, cyano, nitro, hydroxy, hydroxyalkyl, $C(O)R^6$, $C(O)OR^7$, $S(O)_tR^8$, $S(O)_tNR^9R^{10}$, $C(O)NR^9R^{10}$, cycloalkyl, $—(CH_2)_r$-cycloalkyl, heterocyclyl, $—(CH_2)_r$-heterocyclyl, aryl, $—(CH_2)_r$-aryl, heteroaryl and $—(CH_2)_r$-heteroaryl;

$R^6$ are identical or different at each occurrence and are each independently selected from the group consisting of a hydrogen atom, alkyl, haloalkyl, cycloalkyl, heterocyclyl, aryl and heteroaryl, wherein the alkyl, cycloalkyl, heterocyclyl, aryl and heteroaryl are each independently optionally substituted with one or more substituents selected from the group consisting of halogen, alkyl, alkenyl, alkynyl, alkoxy, haloalkyl, haloalkoxy, cyano, amino, nitro, hydroxy and hydroxyalkyl;

$R^7$ are identical or different at each occurrence and are each independently selected from the group consisting of a hydrogen atom, alkyl, alkenyl, alkynyl, haloalkyl, hydroxyalkyl, cycloalkyl, heterocyclyl, aryl and heteroaryl;

$R^8$ are identical or different at each occurrence and are each independently selected from the group consisting of a hydrogen atom, alkyl, alkenyl, alkynyl, haloalkyl, hydroxyalkyl, hydroxy, cycloalkyl, heterocyclyl, aryl and heteroaryl;

$R^9$ and $R^{10}$ are identical or different at each occurrence and are each independently selected from the group consisting of a hydrogen atom, alkyl, alkenyl, alkynyl, haloalkyl, hydroxyalkyl, cycloalkyl, $—(CH_2)_r$-cycloalkyl, heterocyclyl, $—(CH_2)_r$-heterocyclyl, aryl, $—(CH_2)_r$-aryl, heteroaryl and $—(CH_2)_r$-heteroaryl; alternatively, $R^9$ and $R^{10}$, together with the nitrogen atom to which they are attached, form heterocyclyl, and the heterocyclyl is optionally substituted with one or more substituents selected from the group consisting of halogen, alkyl, oxo, alkenyl, alkynyl, alkoxy, haloalkyl, haloalkoxy, cyano, amino, nitro, hydroxy, hydroxyalkyl, cycloalkyl, heterocyclyl, aryl and heteroaryl;

p is 0, 1, 2, 3, 4, 5 or 6;

r is 0, 1, 2, 3, 4, 5 or 6;

m is 0, 1, 2, 3 or 4;

s is 0, 1, 2, 3, 4, 5 or 6; and t is 0, 1 or 2.

In some embodiments of the present disclosure, the compound of general formula (I) or the pharmaceutically acceptable salt thereof is a compound of general formula (I-1) or a pharmaceutically acceptable salt thereof:

(I-1)

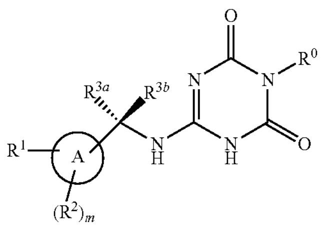

wherein:

ring A, $R^0$, $R^1$, $R^2$, $R^{3a}$, $R^{3b}$ and m are as defined in general formula (I).

In some embodiments of the present disclosure, the compound of general formula (I) or general formula (I-1) or the pharmaceutically acceptable salt thereof is provided, wherein ring A is selected from the group consisting of 3- to 8-membered cycloalkyl, 3- to 12-membered heterocyclyl, 6- to 10-membered aryl and 5- to 10-membered heteroaryl; preferably, ring A is phenyl.

In some embodiments of the present disclosure, the compound of general formula (I) or the pharmaceutically acceptable salt thereof is a compound of general formula (II) or a pharmaceutically acceptable salt thereof:

(II)

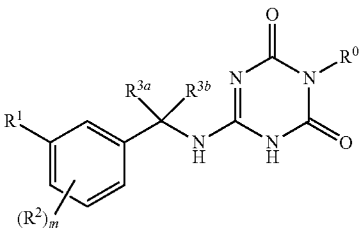

wherein:

$R^0$, $R^1$, $R^2$, $R^{3a}$, $R^{3b}$ and m are as defined in general formula (I).

In some embodiments of the present disclosure, the compound of general formula (I), general formula (I-1) or general formula (II) or the pharmaceutically acceptable salt thereof is a compound of general formula (II-1) or a pharmaceutically acceptable salt thereof:

(II-1)

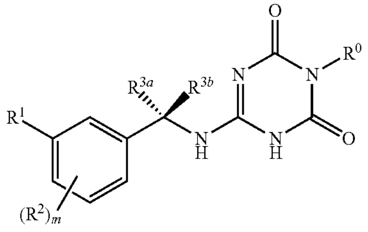

wherein:

$R^0$, $R^1$, $R^2$, $R^{3a}$, $R^{3b}$ and m are as defined in general formula (I).

In some embodiments of the present disclosure, the compound of general formula (I), general formula (I-1), general formula (II) or general formula (II-1) or the pharmaceutically acceptable salt thereof is provided, wherein $R^0$ is $C_{1-6}$ alkyl or

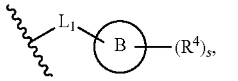

wherein the $C_{1-6}$ alkyl is optionally substituted with one or more substituents selected from the group consisting of halogen, $C_{1-6}$ alkoxy, $C_{1-6}$ haloalkoxy, cyano, amino and hydroxy; $L_1$ is a covalent bond or $(CH_2)_r$; ring B is selected from the group consisting of 3- to 8-membered cycloalkyl, 3- to 12-membered heterocyclyl, 6- to 10-membered aryl and 5- to 10-membered heteroaryl; $R^4$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, oxo, cyano, hydroxy and $C_{1-6}$ hydroxyalkyl; r is 0, 1, 2, 3, 4, 5 or 6; s is 0, 1 or 2.

In some embodiments of the present disclosure, the compound of general formula (I), general formula (I-1), general formula (II) or general formula (II-1) or the pharmaceutically acceptable salt thereof is provided, wherein $R^0$ is selected from the group consisting of $C_{1-6}$ alkyl, 3- to 8-membered cycloalkyl and 3- to 12-membered heterocyclyl; preferably, $R^0$ is selected from the group consisting of $C_{1-6}$ alkyl, 3- to 6-membered cycloalkyl and 3- to 6-membered heterocyclyl; more preferably, $R^{10}$ is selected from the group consisting of isopropyl, tetrahydropyranyl and cyclohexyl; even more preferably, $R^0$ is isopropyl or tetrahydropyranyl; most preferably, $R^0$ is tetrahydropyranyl.

In some embodiments of the present disclosure, the compound of general formula (I), general formula (I-1), general formula (II) or general formula (II-1) or the pharmaceutically acceptable salt thereof is provided, wherein $R^0$ is $C_{1-6}$ alkyl; preferably, $R^0$ is isopropyl.

In some embodiments of the present disclosure, the compound of general formula (I), general formula (I-1), general formula (II) or general formula (II-1) or the pharmaceutically acceptable salt thereof is provided, wherein $R^1$ is selected from the group consisting of halogen, $C_{1-6}$ alkyl, $C_{1-6}$ alkoxy, $C_{1-6}$ haloalkyl, $C_{1-6}$ haloalkoxy and

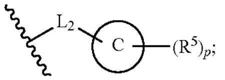

preferably, $R^1$ is selected from the group consisting of $C_{1-6}$ alkyl, $C_{1-6}$ haloalkoxy and

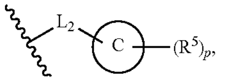

wherein ring C, $L_2$, $R^5$ and p are as defined in general formula (I).

In some embodiments of the present disclosure, the compound of general formula (I), general formula (I-1), general formula (II) or general formula (II-1) or the pharmaceutically acceptable salt thereof is provided, wherein $R^1$ is selected from the group consisting of halogen, $C_{1-6}$ alkyl, $C_{1-6}$ alkoxy, $C_{1-6}$ haloalkyl, $C_{1-6}$ haloalkoxy and

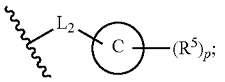

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6.

In some embodiments of the present disclosure, the compound of general formula (I), general formula (I-1), general formula (II) or general formula (II-1) or the pharmaceutically acceptable salt thereof is provided, wherein $R^1$ is selected from the group consisting of halogen, $C_{1-6}$ alkyl, $C_{1-6}$ alkoxy, $C_{1-6}$ haloalkyl, $C_{1-6}$ haloalkoxy and

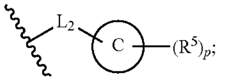

preferably, $R^1$ is selected from the group consisting of $C_{1-6}$ alkyl, $C_{1-6}$ haloalkoxy and

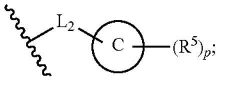

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2.

In some embodiments of the present disclosure, the compound of general formula (I), general formula (I-1), general formula (II) or general formula (II-1) or the pharmaceutically acceptable salt thereof is provided, wherein $R^1$ is selected from the group consisting of halogen, $C_{1-6}$ alkyl, $C_{1-6}$ alkoxy, $C_{1-6}$ haloalkyl, $C_{1-6}$ haloalkoxy and

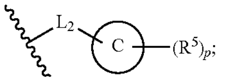

preferably, $R^1$ is selected from the group consisting of $C_{1-6}$ alkyl. $C_{1-6}$ haloalkoxy and

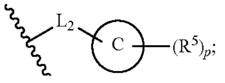

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2.

In some embodiments of the present disclosure, the compound of general formula (I), general formula (I-1), general formula (II) or general formula (II-1) or the pharmaceutically acceptable salt thereof is provided, wherein $R^1$ is $C_{1-6}$ haloalkoxy or

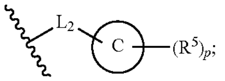

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2.

In some embodiments of the present disclosure, the compound of general formula (I), general formula (I-1), general formula (II) or general formula (II-1) or the pharmaceutically acceptable salt thereof is provided, wherein $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; preferably, $R^2$ are identical or different and are each independently a hydrogen atom or halogen; more preferably, $R^2$ are identical or different and are each independently halogen; most preferably, $R^2$ are fluorine atoms.

In some embodiments of the present disclosure, the compound of general formula (I) or general formula (I-1) or the pharmaceutically acceptable salt thereof is provided, wherein $R^1$ and one adjacent $R^2$, or two adjacent $R^2$, fuse with ring A to form 3- to 8-membered cycloalkyl or 3- to 12-membered heterocyclyl; preferably, $R^1$ and one adjacent $R^2$, or two adjacent $R^2$, fuse with ring A to form 3- to 6-membered cycloalkyl or 3- to 6-membered heterocyclyl; more preferably, $R^1$ and one adjacent $R^2$ fuse with ring A to form cyclobutyl, tetrahydrofuranyl, cyclopentyl and cyclohexyl.

In some embodiments of the present disclosure, the compound of general formula (I) or general formula (I-1) or the pharmaceutically acceptable salt thereof is provided, wherein $R^1$ and one adjacent $R^2$, or two adjacent $R^2$, fuse with ring A to form 3- to 8-membered cycloalkyl or 3- to 12-membered heterocyclyl; preferably, $R^1$ and one adjacent $R^2$ fuse with ring A to form cyclopentyl.

In some embodiments of the present disclosure, the compound of general formula (II) or general formula (II-1) or the pharmaceutically acceptable salt thereof is provided, wherein $R^1$ and one adjacent $R^2$, or two adjacent $R^2$, fuse with phenyl to form 3- to 8-membered cycloalkyl or 3- to 12-membered heterocyclyl; preferably, $R^1$ and one adjacent $R^2$, or two adjacent $R^2$, fuse with phenyl to form 3- to 6-membered cycloalkyl or 3- to 6-membered heterocyclyl; more preferably, $R^1$ and one adjacent $R^2$ fuse with phenyl to form cyclobutyl, tetrahydrofuranyl, cyclopentyl and cyclohexyl.

In some embodiments of the present disclosure, the compound of general formula (II) or general formula (II-1) or the pharmaceutically acceptable salt thereof is provided, wherein $R^1$ and one adjacent $R^2$, or two adjacent $R^2$, fuse with phenyl to form 3- to 8-membered cycloalkyl or 3- to 12-membered heterocyclyl; preferably, $R^1$ and one adjacent $R^2$ fuse with phenyl to form cyclopentyl.

In some embodiments of the present disclosure, the compound of general formula (I) or general formula (I-1) or the pharmaceutically acceptable salt thereof is provided, wherein $R^1$ is selected from the group consisting of halogen, $C_{1-6}$ alkyl, $C_{1-6}$ alkoxy, $C_{1-6}$ haloalkyl, $C_{1-6}$ haloalkoxy and

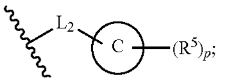

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; alternatively, $R^1$ and one adjacent $R^2$, or two adjacent $R^2$, fuse with ring A to form 3- to 8-membered cycloalkyl or 3- to 12-membered heterocyclyl.

In some embodiments of the present disclosure, the compound of general formula (I) or general formula (I-1) or the pharmaceutically acceptable salt thereof is provided, wherein $R^1$ is selected from the group consisting of $C_{1-6}$ alkyl, $C_{1-6}$ haloalkoxy and

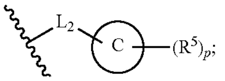

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; alternatively, $R^1$ and one adjacent $R^2$ fuse with ring A to form 3- to 6-membered cycloalkyl or 3- to 6-membered heterocyclyl.

In some embodiments of the present disclosure, the compound of general formula (I) or general formula (I-1) or the pharmaceutically acceptable salt thereof is provided, wherein $R^1$ is selected from the group consisting of $C_{1-6}$ alkyl, $C_{1-6}$ haloalkoxy and

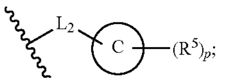

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; alternatively, $R^1$ and one adjacent $R^2$ fuse with ring A to form cyclobutyl, tetrahydrofuranyl, cyclopentyl and cyclohexyl.

In some embodiments of the present disclosure, the compound of general formula (I) or general formula (I-1) or the pharmaceutically acceptable salt thereof is provided, wherein $R^1$ is $C_{1-6}$ haloalkoxy or

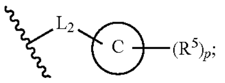

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; alternatively, $R^1$ and one adjacent $R^2$ fuse with ring A to form cyclobutyl, tetrahydrofuranyl, cyclopentyl and cyclohexyl.

In some embodiments of the present disclosure, the compound of general formula (I) or general formula (I-1) or the pharmaceutically acceptable salt thereof is provided, wherein $R^1$ is $C_{1-6}$ haloalkoxy or

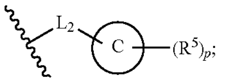

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; alternatively, $R^1$ and one adjacent $R^2$ fuse with ring A to form cyclopentyl.

In some embodiments of the present disclosure, the compound of general formula (II) or general formula (II-1) or the pharmaceutically acceptable salt thereof is provided, wherein $R^1$ is selected from the group consisting of halogen, $C_{1-6}$ alkyl, $C_{1-6}$ alkoxy, $C_{1-6}$ haloalkyl, $C_{1-6}$ haloalkoxy and

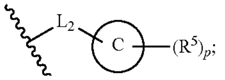

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; alternatively, $R^1$ and one adjacent $R^2$, or two adjacent $R^2$, fuse with phenyl to form 3- to 8-membered cycloalkyl or 3- to 12-membered heterocyclyl.

In some embodiments of the present disclosure, the compound of general formula (II) or general formula (II-1) or the pharmaceutically acceptable salt thereof is provided, wherein $R^1$ is selected from the group consisting of $C_{1-6}$ alkyl, $C_{1-6}$ haloalkoxy and

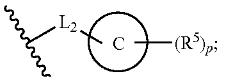

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2; $R^2$ are identical or different and are each independently a hydrogen atom or halogen; alternatively, $R^1$ and one adjacent $R^2$ fuse with phenyl to form 3- to 6-membered cycloalkyl or 3- to 6-membered heterocyclyl.

In some embodiments of the present disclosure, the compound of general formula (II) or general formula (II-1) or the pharmaceutically acceptable salt thereof is provided, wherein $R^1$ is $C_{1-6}$ haloalkoxy or

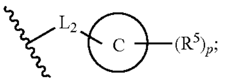

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; alternatively, $R^1$ and one adjacent $R^2$ fuse with phenyl to form cyclobutyl, tetrahydrofuranyl, cyclopentyl and cyclohexyl.

In some embodiments of the present disclosure, the compound of general formula (II) or general formula (II-1) or the pharmaceutically acceptable salt thereof is provided, wherein $R^1$ is $C_{1-6}$ haloalkoxy or

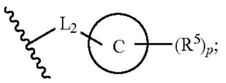

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; alternatively, $R^1$ and one adjacent $R^2$ fuse with phenyl to form cyclopentyl.

In some embodiments of the present disclosure, the compound of general formula (I), general formula (I-1), general formula (II) or general formula (II-1) or the pharmaceutically acceptable salt thereof is provided, wherein $R^{3a}$ is selected from the group consisting of halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; preferably, $R^{3a}$ is $C_{1-6}$ alkyl; more preferably, $R^{3a}$ is methyl.

In some embodiments of the present disclosure, the compound of general formula (I), general formula (I-1), general formula (II) or general formula (II-1) or the pharmaceutically acceptable salt thereof is provided, wherein m is 0, 1 or 2; preferably, m is 0 or 1.

In some embodiments of the present disclosure, the compound of general formula (I) or general formula (I-1) or the pharmaceutically acceptable salt thereof is provided, wherein

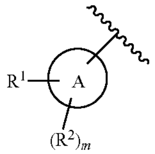

is

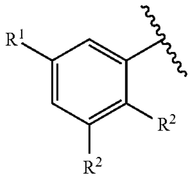

or

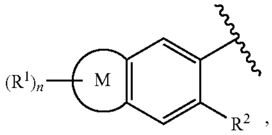

wherein ring M is 3- to 8-membered cycloalkyl or 3- to 12-membered heterocyclyl, $R^f$ is selected from the group consisting of a hydrogen atom, halogen and $C_{1-6}$ alkyl, n is 0 or 1, and $R^1$ and $R^2$ are as defined in general formula (I) or general formula (I-1); preferably,

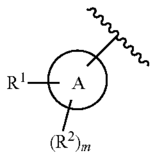

is

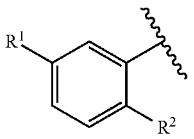

or

-continued

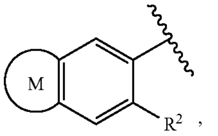

wherein ring M is 3- to 6-membered cycloalkyl or 3- to 6-membered heterocyclyl, and $R^1$ and $R^2$ are as defined in general formula (I) or general formula (I-1), more preferably,

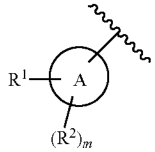

is selected from the group consisting of

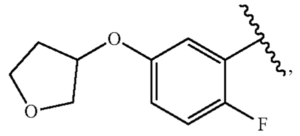

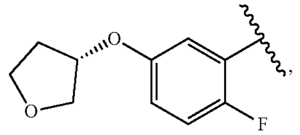

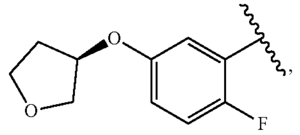

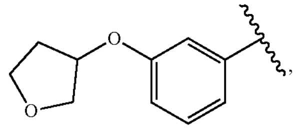

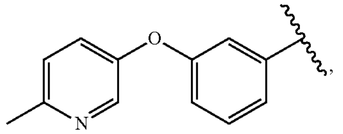

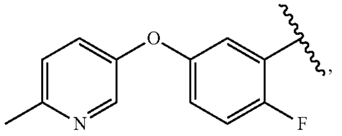

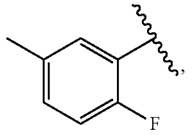

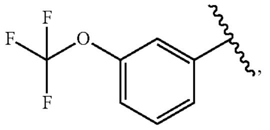

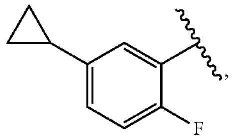

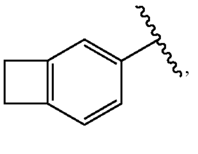

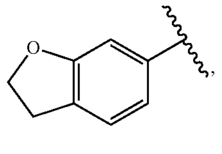

-continued

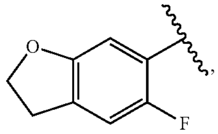,
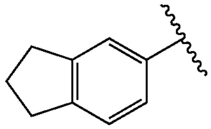
and
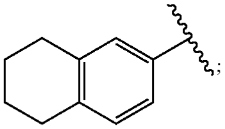;

most preferably,

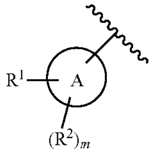
is
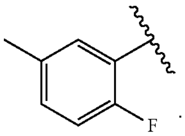.

In some embodiments of the present disclosure, the compound of general formula (I) or general formula (I-1) or the pharmaceutically acceptable salt thereof is provided, wherein

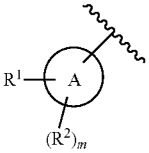

is selected from the group consisting of

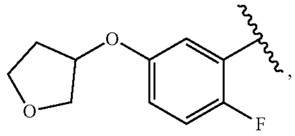,
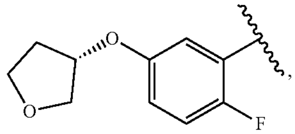,
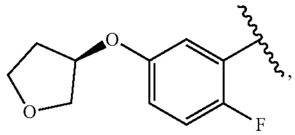,
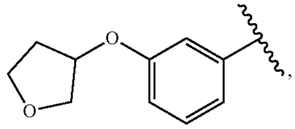,
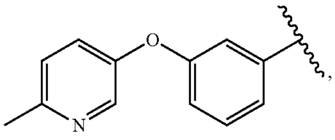,

-continued

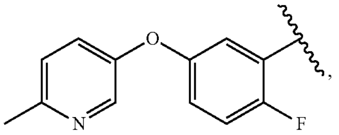,
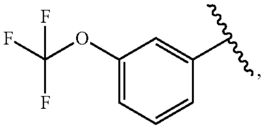,
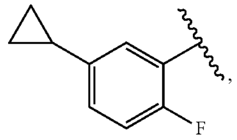,
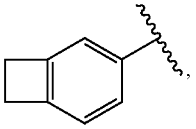,
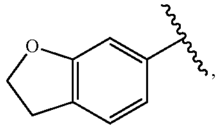,
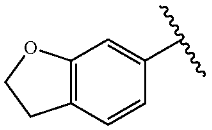
and
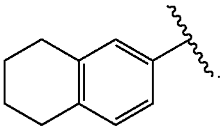.

In some embodiments of the present disclosure, the compound of general formula (II) or general formula (II-1) or the pharmaceutically acceptable salt thereof is provided, wherein

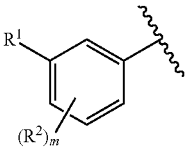
is
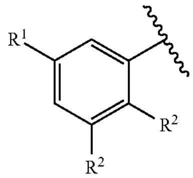
or
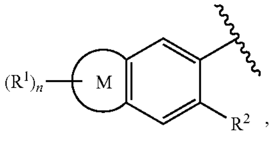, wherein ring M is 3- to 8-membered cycloalkyl or 3- to 12-membered heterocyclyl, $R^f$ is selected from the group consisting of a hydrogen atom, halogen and $C_{1-6}$ alkyl, n is 0 or 1, and $R^1$ and $R^2$ are as defined in general formula (II) or general formula (II-1); preferably,

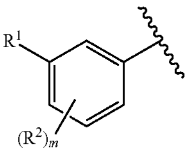
is
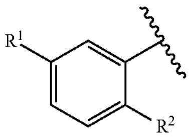
or
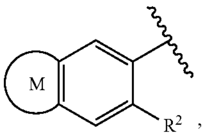, wherein ring M is 3- to 6-membered cycloalkyl or 3- to 6-membered heterocyclyl, and $R^1$ and $R^2$ are as defined in general formula (II) or general formula (II-1), more preferably,

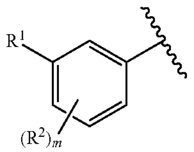
is selected from the group consisting of
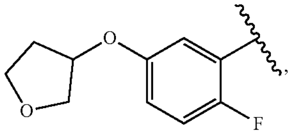
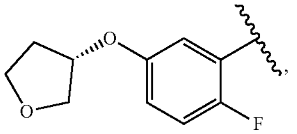
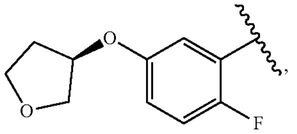
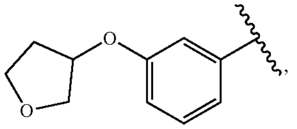
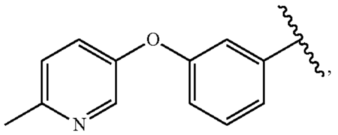
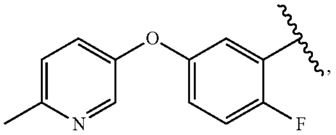
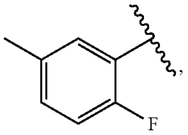
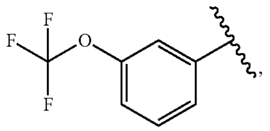
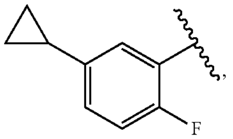
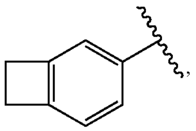
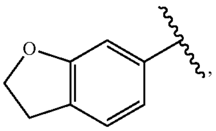
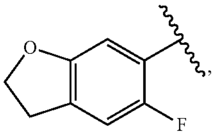
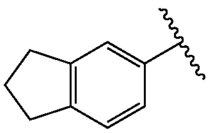
and
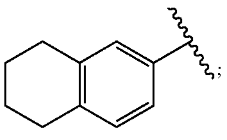
;
most preferably,
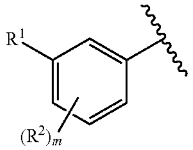
is
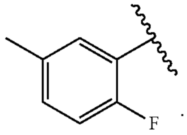
.
In some embodiments of the present disclosure, the compound of general formula (II) or general formula (II-1) or the pharmaceutically acceptable salt thereof is provided, wherein
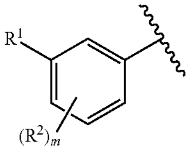
is selected from the group consisting of
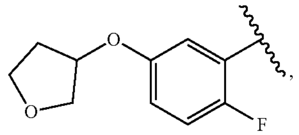
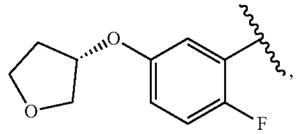
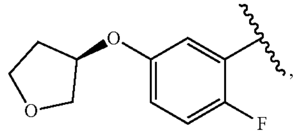
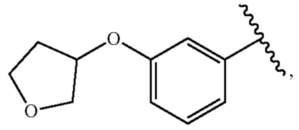
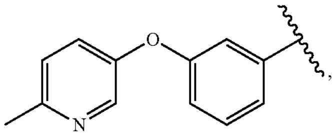
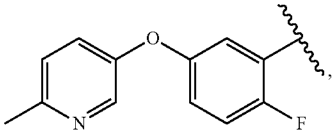
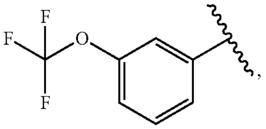
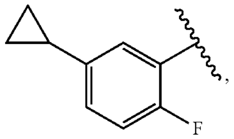
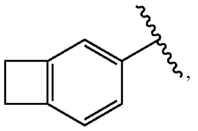
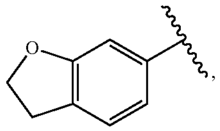

-continued

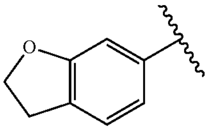 and 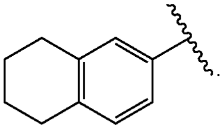.

In some embodiments of the present disclosure, the compound of general formula (I) or general formula (I-1) or the pharmaceutically acceptable salt thereof is provided, wherein ring A is phenyl; $R^0$ is selected from the group consisting of $C_{1-6}$ alkyl, 3- to 8-membered cycloalkyl and 3- to 12-membered heterocyclyl; $R^1$ is selected from the group consisting of halogen, $C_{1-6}$ alkyl, $C_{1-6}$ alkoxy, $C_{1-6}$ haloalkyl, $C_{1-6}$ haloalkoxy and

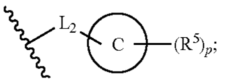

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; alternatively, $R^1$ and one adjacent $R^2$, or two adjacent $R^2$, fuse with ring A to form 3- to 8-membered cycloalkyl or 3- to 12-membered heterocyclyl; $R^{3a}$ is selected from the group consisting of halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; $R^{3b}$ is a hydrogen atom; m is 0, 1 or 2.

In some embodiments of the present disclosure, the compound of general formula (I) or general formula (I-1) or the pharmaceutically acceptable salt thereof is provided, wherein ring A is phenyl; $R^0$ is $C_{1-6}$ alkyl; $R^1$ is selected from the group consisting of halogen, $C_{1-6}$ alkyl, $C_{1-6}$ alkoxy, $C_{1-6}$ haloalkyl, $C_{1-6}$ haloalkoxy and

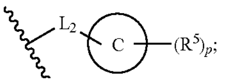

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; alternatively, $R^1$ and one adjacent $R^2$, or two adjacent $R^2$, fuse with ring A to form 3- to 8-membered cycloalkyl or 3- to 12-membered heterocyclyl; $R^{3a}$ is selected from the group consisting of halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; $R^{3b}$ is a hydrogen atom; m is 0, 1 or 2.

In some embodiments of the present disclosure, the compound of general formula (II) or general formula (II-1) or the pharmaceutically acceptable salt thereof is provided, wherein $R^0$ is selected from the group consisting of $C_{1-6}$ alkyl, 3- to 6-membered cycloalkyl and 3- to 6-membered heterocyclyl; $R^1$ is selected from the group consisting of $C_{1-6}$ alkyl, $C_{1-6}$ haloalkoxy and

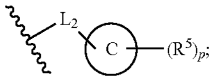

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2; $R^2$ are identical or different and are each independently a hydrogen atom or halogen; alternatively, $R^1$ and one adjacent $R^2$ fuse with phenyl to form 3- to 6-membered cycloalkyl or 3- to 6-membered heterocyclyl; $R^{3a}$ is methyl; $R^{3b}$ is a hydrogen atom; m is 0 or 1.

In some embodiments of the present disclosure, the compound of general formula (II) or general formula (II-1) or the pharmaceutically acceptable salt thereof is provided, wherein $R^0$ is $C_{1-6}$ alkyl; $R^1$ is selected from the group consisting of $C_{1-6}$ alkyl, $C_{1-6}$ haloalkoxy and

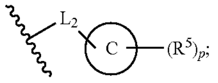

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2; $R^2$ are identical or different and are each independently a hydrogen atom or halogen; alternatively, $R^1$ and one adjacent $R^2$ fuse with phenyl to form 3- to 6-membered cycloalkyl or 3- to 6-membered heterocyclyl; $R^{3a}$ is methyl; $R^{3b}$ is a hydrogen atom; m is 0 or 1.

In some embodiments of the present disclosure, the compound of general formula (II) or general formula (II-1) or the pharmaceutically acceptable salt thereof is provided, wherein $R^0$ is $C_{1-6}$ alkyl; $R^1$ is $C_{1-6}$ haloalkoxy or

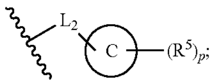

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; alternatively, $R^1$ and one adjacent $R^2$ fuse with phenyl to form cyclobutyl, tetrahydrofuranyl, cyclopentyl and cyclohexyl; $R^{3a}$ is methyl; $R^{3b}$ is a hydrogen atom; m is 0 or 1.

In some embodiments of the present disclosure, the compound of general formula (I) or general formula (I-1) or the pharmaceutically acceptable salt thereof is provided, wherein

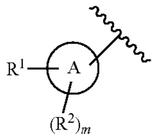
is
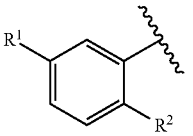
or
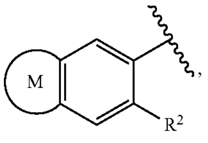

wherein ring M is 3- to 6-membered cycloalkyl or 3- to 6-membered heterocyclyl; $R^0$ is selected from the group consisting of $C_{1-6}$ alkyl, 3- to 8-membered cycloalkyl and 3- to 12-membered heterocyclyl; $R^1$ is selected from the group consisting of $C_{1-6}$ alkyl, $C_{1-6}$ haloalkoxy and

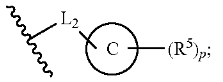

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$, alkoxy, $C_{1-6}$ haloalkyl and $C_{1-6}$ haloalkoxy; $R^{3a}$ is selected from the group consisting of halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; $R^{3b}$ is a hydrogen atom; m is 0, 1 or 2.

In some embodiments of the present disclosure, the compound of general formula (I) or general formula (I-1) or the pharmaceutically acceptable salt thereof is provided, wherein

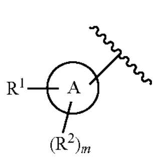
is
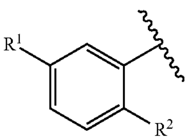
or

-continued

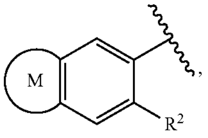

wherein ring M is 3- to 6-membered cycloalkyl or 3- to 6-membered heterocyclyl; $R^0$ is $C_{1-6}$ alkyl; $R^1$ is selected from the group consisting of $C_{1-6}$ alkyl, $C_{1-6}$ haloalkoxy and

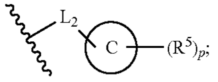

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; $R^{3a}$ is selected from the group consisting of halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; $R^{3b}$ is a hydrogen atom; m is 0, 1 or 2.

In some embodiments of the present disclosure, the compound of general formula (I) or general formula (I-1) or the pharmaceutically acceptable salt thereof is provided, wherein

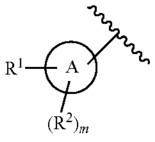
is
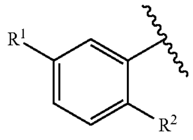
or
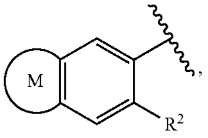

wherein ring M is 3- to 6-membered cycloalkyl or 3- to 6-membered heterocyclyl; $R^0$ is $C_{1-6}$ alkyl; $R^1$ is $C_{1-6}$ haloalkoxy or

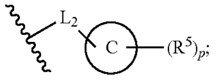

$L_2$ is a covalent bond or an oxygen atom; ring C is selected from the group consisting of 3- to 8-membered cycloalkyl, 3- to 12-membered heterocyclyl, 6- to 10-membered aryl and 5- to 10-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1, 2, 3, 4, 5 or 6; $R^2$ are identical or different and are each independently selected from the group consisting of a hydrogen atom, halogen, $C_{1-6}$ alkyl, $C_{2-6}$ alkenyl, $C_{2-6}$ alkynyl, $C_{1-6}$ alkoxy, $C_{1-6}$ haloalkyl and $C_{1-6}$ haloalkoxy; $R^{3a}$ is selected from the group consisting of halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; $R^{3b}$ is a hydrogen atom; m is 0, 1 or 2.

In some embodiments of the present disclosure, the compound of general formula (II) or general formula (II-1) or the pharmaceutically acceptable salt thereof is provided, wherein

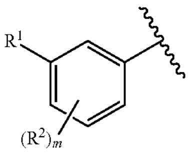 is 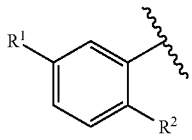 or

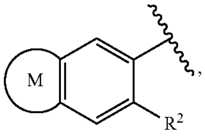, wherein ring M is 3- to 6-membered cycloalkyl or 3- to 6-membered heterocyclyl; $R^0$ is selected from the group consisting of $C_{1-6}$ alkyl, 3- to 6-membered cycloalkyl and 3- to 6-membered heterocycyl; $R^1$ is selected from the group consisting of $C_{1-6}$ alkyl, $C_{1-6}$ haloalkoxy and

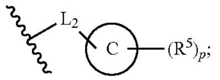;

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2; $R^2$ are identical or different and are each independently a hydrogen atom or halogen; $R^{3a}$ is methyl; $R^{3b}$ is a hydrogen atom; m is 0 or 1.

In some embodiments of the present disclosure, the compound of general formula (II) or general formula (II-1) or the pharmaceutically acceptable salt thereof is provided, wherein

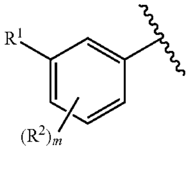 is 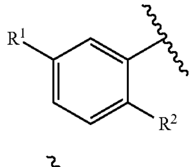 or

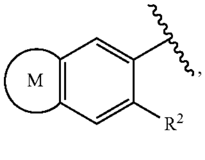, wherein ring M is 3- to 6-membered cycloalkyl or 3- to 6-membered heterocyclyl; $R^0$ is $C_{1-6}$ alkyl; $R^1$ is selected from the group consisting of $C_{1-6}$ alkyl, $C_{1-6}$ haloalkoxy and

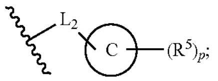;

$L_2$ is a covalent bond or an oxygen atom; ring C is selected from the group consisting of 3- to 6-membered cycloalkyl, 3- to 6-membered heterocyclyl and 5- or 6-membered heteroaryl; $R^5$ are identical or different and are each independently selected from the group consisting of a hydrogen atom, halogen, $C_{1-6}$ alkyl, $C_{1-6}$ alkoxy, $C_{1-6}$ haloalkyl, $C_{1-6}$ haloalkoxy and $C_{1-6}$ hydroxyalkyl; p is 0, 1 or 2; $R^2$ are identical or different and are each independently a hydrogen atom or halogen; $R^{3a}$ is methyl; $R^{3b}$ is a hydrogen atom; m is 0 or 1.

In some embodiments of the present disclosure, the compound of general formula (II) or general formula (II-1) or the pharmaceutically acceptable salt thereof is provided, wherein

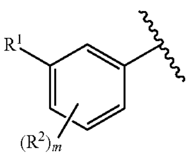 is 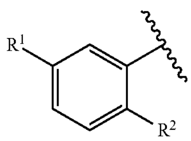 or

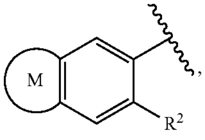, wherein ring M is 3- to 6-membered cycloalkyl or 3- to 6-membered heterocyclyl; $R^0$ is $C_{1-6}$ alkyl; $R^1$ is $C_{1-6}$ haloalkoxy or

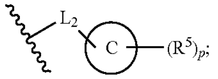;

$L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2; $R^2$ are identical or different and are each independently a hydrogen atom or halogen; $R^{3a}$ is methyl; $R^{3b}$ is a hydrogen atom; m is 0 or 1.

In some embodiments of the present disclosure, the compound of general formula (II) or general formula (II-1) or the pharmaceutically acceptable salt thereof is provided, wherein $R^0$ is selected from the group consisting of isopropyl, tetrahydropyranyl and cyclohexyl;

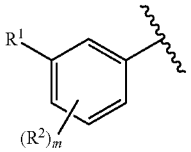 is 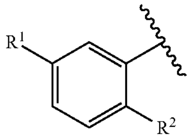 or

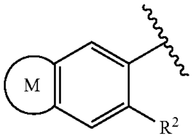 , wherein ring M is 3- to 6-membered cycloalkyl or 3- to 6-membered heterocyclyl; $R^1$ is selected from the group consisting of $C_{1-6}$ alkyl, $C_{1-6}$ haloalkoxy and

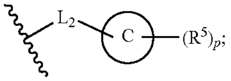

$R^2$ are identical or different and are each independently a hydrogen atom or halogen; alternatively, $R^1$ and one adjacent $R^2$ fuse with phenyl to form cyclobutyl, tetrahydrofuranyl, cyclopentyl and cyclohexyl; $R^{3a}$ is methyl; $R^{3b}$ is a hydrogen atom; $L_2$ is a covalent bond or an oxygen atom; ring C is selected from the group consisting of cyclopropyl, tetrahydrofuranyl and pyridinyl; $R^5$ are identical or different and are each independently selected from the group consisting of a hydrogen atom, halogen and $C_{1-6}$ alkyl; p is 0, 1 or 2.

In some embodiments of the present disclosure, the compound of general formula (II) or general formula (II-1) or the pharmaceutically acceptable salt thereof is provided, wherein $R^0$ is tetrahydropyranyl,

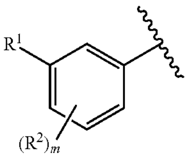 is 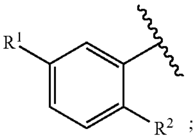 ;

$R^1$ is $C_{1-6}$ alkyl; $R^2$ is a hydrogen atom or halogen, $R^{3a}$ is methyl; $R^{3b}$ is a hydrogen atom.

TABLE A

| Typical compounds disclosed herein include, but are not limited to: | |
|---|---|
| Example No. | Structures and names of compounds |
| 1 | 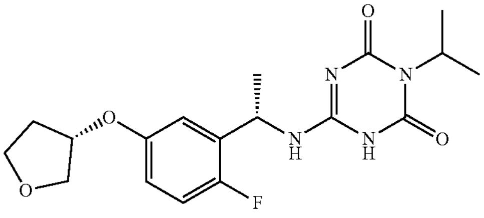<br>1 |

TABLE A-continued

| Typical compounds disclosed herein include, but are not limited to: | |
|---|---|
| Example No. | Structures and names of compounds |
| | 6-(((S)-1-(2-Fluoro-5-(((S)-tetrahydrofuran-3-yl)oxy)phenyl)ethyl)amino)-3-isopropyl-1,3,5-triazine-2,4(1H,3H)-dione 1 |
| | 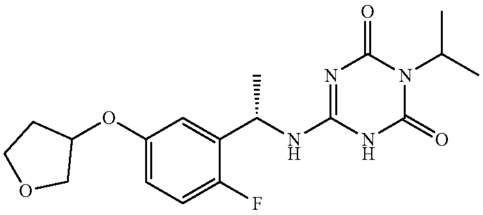 [SMILES: CC(C)n1c(=O)nc(N[C@@H](C)c2cc(OC3CCOC3)ccc2F)[nH]c1=O]<br>6-(((S)-1-(2-Fluoro-5-((tetrahydrofuran-3-yl)oxy)phenyl)ethyl)amino)-3-isopropyl-1,3,5-triazine-2,4(1H,3H)-dione |
| 2 | 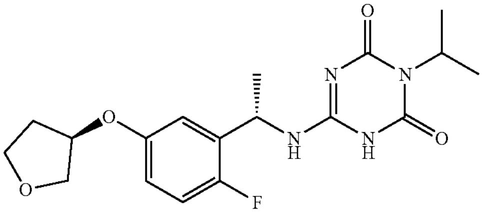<br>2<br>6-(((S)-1-(2-Fluoro-5-(((R)-tetrahydrofuran-3-yl)oxy)phenyl)ethyl)amino)-3-isopropyl-1,3,5-triazine-2,4(1H,3H)-dione 2 |
| 3 | 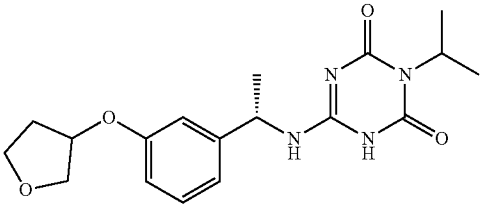<br>3<br>3-Isopropyl-6-(((1S)-1-(3-((tetrahydrofuran-3-yl)oxy)phenyl)ethyl)amino)-1,3,5-triazine-2,4(1H,3H)-dione 3 |
| 4 | 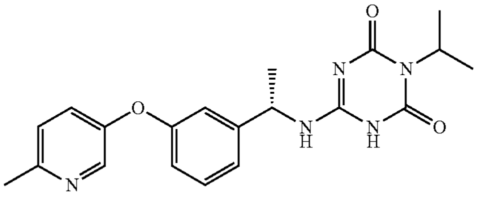<br>4<br>(S)-3-Isopropyl-6-((1-(3-((6-methylpyridin-3-yl)oxy)phenyl)ethyl)amino)-1,3,5-triazine-2,4(1H,3H)-dione 4 |

TABLE A-continued

| Typical compounds disclosed herein include, but are not limited to: | |
|---|---|
| Example No. | Structures and names of compounds |
| 5 | 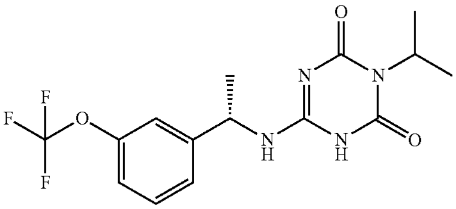<br>5<br>(S)-3-Isopropyl-6-((1-(3-(trifluoromethoxy) phenyl)ethyl)amino)-1,3,5-triazine-2,4(1H,3H)-dione 5 |
| 6 | 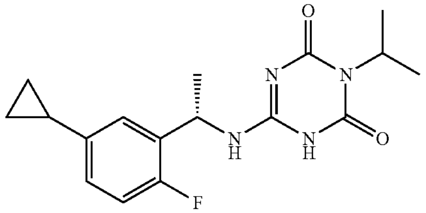<br>6<br>(S)-6-((1-(5-Cyclopropyl-2-fluorophenyl)ethyl)amino)-3-isopropyl-1,3,5-triazine-2,4(1H,3H)-dione 6 |
| 7 | 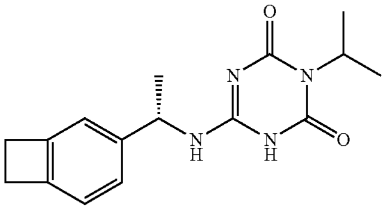<br>7<br>(S)-6-((1-(Bicyclo[4.2.0]ctan-1(6),2,4-trien-3-yl)ethyl)amino)-3-isopropyl-1,3,5-triazine-2,4(1H,3H)-dione 7 |
| 8 | 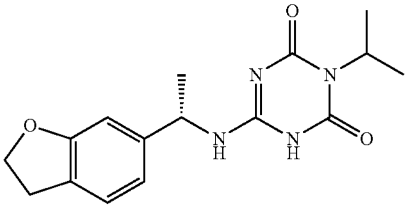<br>8<br>(S)-6-((1-(2,3-Dihydrobenzofuran-6-yl)ethyl)amino)-3-isopropyl-1,3,5-triazine-2,4(1H,3H)-dione 8 |

TABLE A-continued

| Typical compounds disclosed herein include, but are not limited to: | |
|---|---|
| Example No. | Structures and names of compounds |
| 9 | 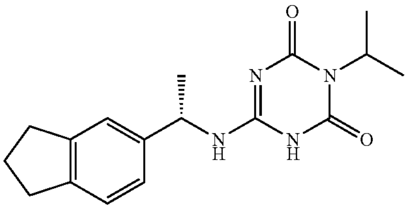<br>9<br>(S)-6-((1-(2,3-Dihydro-1H-inden-5-yl)ethyl)amino)-3-isopropyl-1,3,5-triazine-2,4(1H,3H)-dione 9 |
| 10 | 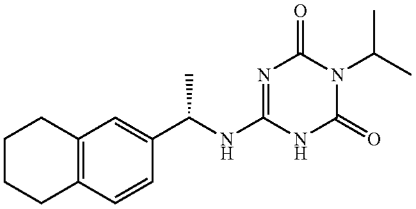<br>10<br>(S)-3-Isopropyl-6-((1-(5,6,7,8-tetrahydronaphthalen-2-yl)ethyl)amino)-1,3,5-triazine-2,4(1H,3H)-dione 10 |
| 11 | 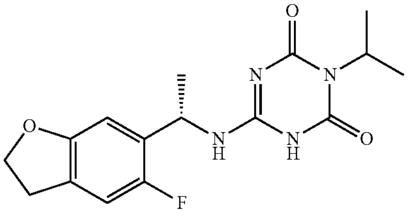<br>11<br>(S)-6-((1-(5-Fluoro-2,3-dihydrobenzofuran-6-yl)ethyl)amino)-3-isopropyl-1,3,5-triazine-2,4(1H,3H)-dione 11 |
| 12 | 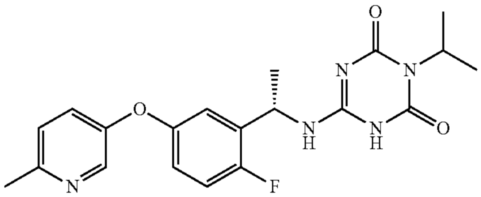<br>12<br>(S)-6-((1-(2-Fluoro-5-((6-methylpyridin-3-yl)oxy)phenyl)ethyl)amino)-3-isopropyl-1,3,5-triazine-2,4(1H,3H)-dione 12 |

TABLE A-continued

Typical compounds disclosed herein include, but are not limited to:

| Example No. | Structures and names of compounds |
| --- | --- |
| 13 | 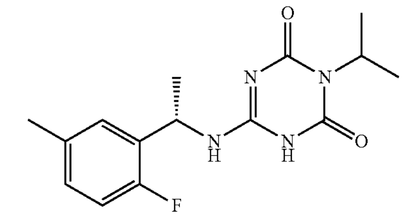 13 (S)-6-((1-(2-Fluoro-5-methylphenyl)ethyl)amino)-3-isopropyl-1,3,5-triazine-2,4(1H,3H)-dione 13 |
| 14 | 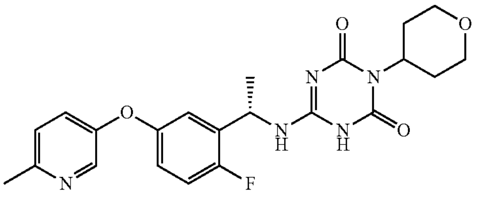 14 (S)-6-((1-(2-Fluoro-5-((6-methylpyridin-3-yl)oxy)phenyl)ethyl)amino)-3-(tetrahydro-2H-pyran-4-yl)-1,3,5-triazine-2,4(1H,3H)-dione 14 |
| 15 | 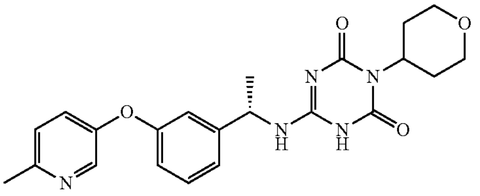 15 (S)-6-((1-(3-((6-Methylpyridin-3-yl)oxy)phenyl)ethyl)amino)-3-(tetrahydro-2H-pyran-4-yl)-1,3,5-triazine-2,4(1H,3H)-dione 15 |
| 16 | 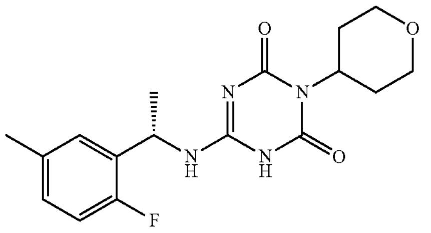 16 (S)-6-((1-(2-Fluoro-5-methylphenyl)ethyl)amino)-3-(tetrahydro-2H-pyran-4-yl)-1,3,5-triazine-2,4(1H,3H)-dione 16 |
| 17 | 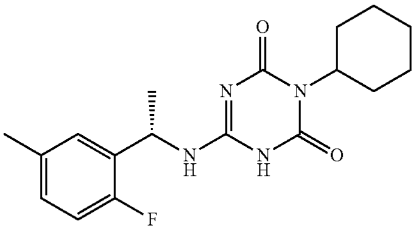 17 (S)-3-Cyclohexyl-6-((1-(2-fluoro-5-methylphenyl)ethyl)amino)-1,3,5-triazine-2,4(1H,3H)-dione 17 |

Another aspect of the present disclosure relates to a method for preparing a compound of general formula (I) or a pharmaceutically acceptable salt thereof, which comprises:

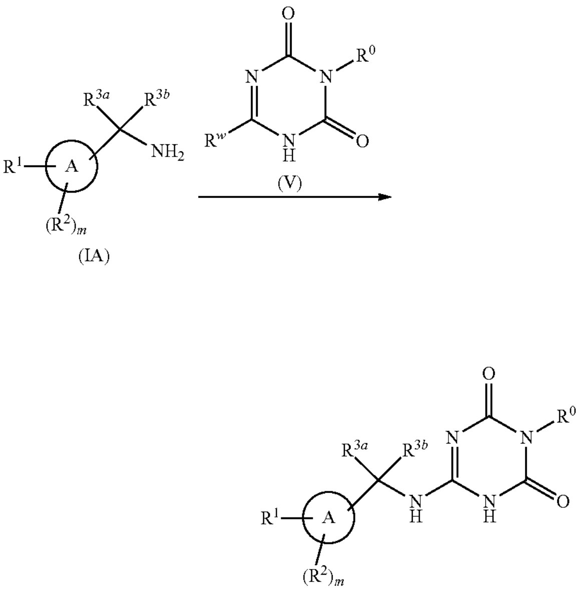

(I)

conducting a nucleophilic substitution reaction of a compound of general formula (IA) or a salt (preferably hydrochloride) thereof with a compound of general formula (V) to give the compound of general formula (I) or the pharmaceutically acceptable salt thereof; wherein:

$R^w$ is a leaving group, preferably pyrazolyl;

ring A, $R^0$, $R^1$, $R^2$, $R^{3a}$, $R^{3b}$ and m are as defined in general formula (I).

Another aspect of the present disclosure relates to a method for preparing a compound of general formula (I-1) or a pharmaceutically acceptable salt thereof, which comprises:

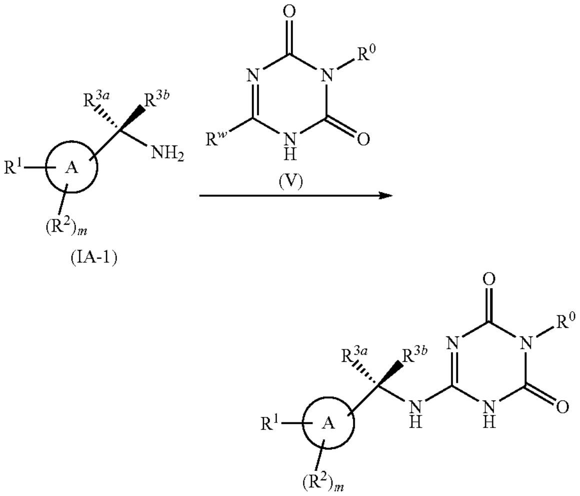

(IA-1) (V) (I-1)

conducting a nucleophilic substitution reaction of a compound of general formula (IA-1) or a salt (preferably hydrochloride) thereof with a compound of general formula (V) to give the compound of general formula (I-1) or the pharmaceutically acceptable salt thereof;

wherein:

$R^w$ is a leaving group, preferably pyrazolyl;

ring A, $R^0$, $R^1$, $R^2$, $R^{3a}$, $R^{3b}$ and m are as defined in general formula (I-1).

Another aspect of the present disclosure relates to a method for preparing a compound of general formula (II) or a pharmaceutically acceptable salt thereof, which comprises:

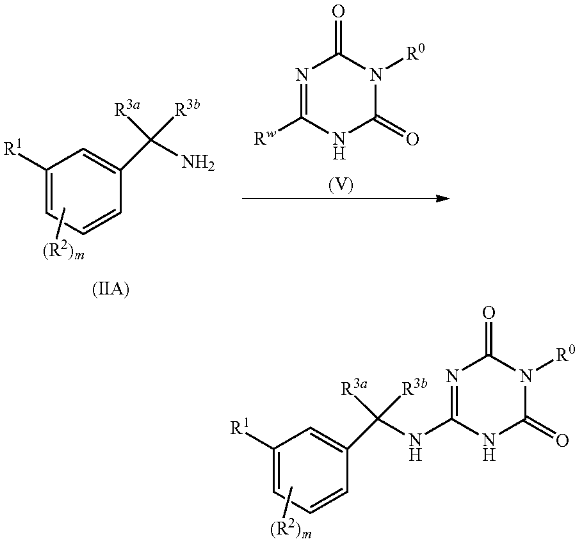

(IIA) (V) (II)

conducting a nucleophilic substitution reaction of a compound of general formula (IIA) or a salt (preferably hydrochloride) thereof with a compound of general formula (V) to give the compound of general formula (II) or the pharmaceutically acceptable salt thereof; wherein:

$R^w$ is a leaving group, preferably pyrazolyl;

$R^0$, $R^1$, $R^2$, $R^{3a}$, $R^{3b}$ and m are as defined in general formula (II).

Another aspect of the present disclosure relates to a method for preparing a compound of general formula (II-1) or a pharmaceutically acceptable salt thereof, which comprises:

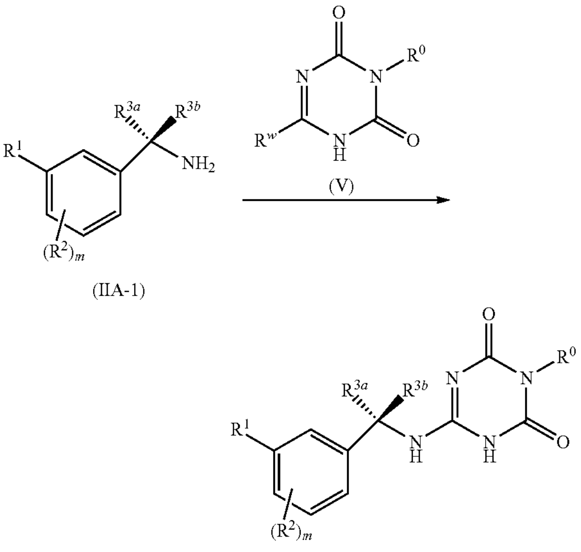

(IIA-1) (V) (II-1)

conducting a nucleophilic substitution reaction of a compound of general formula (IIA-1) or a salt (preferably hydrochloride) thereof with a compound of general formula (V) to give the compound of general formula (II-1) or the pharmaceutically acceptable salt thereof;

wherein:

$R^w$ is a leaving group, preferably pyrazolyl;

$R^0$, $R^1$, $R^2$, $R^{3a}$, $R^{3b}$ and m are as defined in general formula (II-1).

Another aspect of the present disclosure relates to a pharmaceutical composition comprising the compounds of general formula (I), general formula (I-1), general formula (II) and general formula (II-1) disclosed herein and the compounds shown in Table A or pharmaceutically acceptable salts thereof, and one or more pharmaceutically acceptable carriers, diluents or excipients.

The present disclosure further relates to use of the compounds of general formula (I), general formula (I-1), general formula (II) and general formula (II-1) and the compounds shown in Table A or pharmaceutically acceptable salts thereof, or the pharmaceutical composition comprising the same, in preparing a myosin inhibitor.

The present disclosure further relates to use of the compounds of general formula (I), general formula (I-1), general formula (II) and general formula (II-1) and the compounds shown in Table A or pharmaceutically acceptable salts thereof, or the pharmaceutical composition comprising the same, in preparing a medicament for treating a disease or condition selected from the group consisting of diastolic heart failure with preserved ejection fraction, ischemic heart disease, angina pectoris, restrictive cardiomyopathy, diastolic dysfunction, hypertrophic cardiomyopathy (HCM) (e.g., non-obstructive hypertrophic cardiomyopathy (nHCM) or obstructive hypertrophic cardiomyopathy (oHCM)), heart failure with preserved ejection fraction (HFpEF), heart failure with mid-range ejection fraction (HFmREF), valvular diseases, aortic stenosis, inflammatory cardiomyopathy, Löeffler endocarditis, endomyocardial fibrosis, infiltrative cardiomyopathy, hemochromatosis, Fabry disease, glycogen storage disease, congenital heart defect, tetralogy of Fallot, left ventricular hypertrophy, refractory angina and Chagas disease, preferably from the group consisting of ischemic heart disease, restrictive cardiomyopathy, hypertrophic cardiomyopathy (HCM), inflammatory cardiomyopathy, infiltrative cardiomyopathy, congenital heart defect and left ventricular hypertrophy, more preferably from hypertrophic cardiomyopathy (HCM), and most preferably from non-obstructive hypertrophic cardiomyopathy (nHCM) or obstructive hypertrophic cardiomyopathy (oHCM).

The present disclosure further relates to use of the compounds of general formula (I), general formula (I-1), general formula (II) and general formula (II-1) and the compounds shown in Table A or pharmaceutically acceptable salts thereof, or the pharmaceutical composition comprising the same, in preparing a medicament for treating a myosin-mediated disease or condition, wherein the disease or condition is selected from the group consisting of diastolic heart failure with preserved ejection fraction, ischemic heart disease, angina pectoris, restrictive cardiomyopathy, diastolic dysfunction, hypertrophic cardiomyopathy (HCM), heart failure with preserved ejection fraction (HFpEF), heart failure with mid-range ejection fraction (HFmREF), valvular diseases, aortic stenosis, inflammatory cardiomyopathy, Löefler endocarditis, endomyocardial fibrosis, infiltrative cardiomyopathy, hemochromatosis, Fabry disease, glycogen storage disease, congenital heart defect, tetralogy of Fallot, left ventricular hypertrophy, refractory angina and Chagas disease, preferably from the group consisting of ischemic heart disease, restrictive cardiomyopathy, hypertrophic cardiomyopathy (HCM), inflammatory cardiomyopathy, infiltrative cardiomyopathy, congenital heart defect and left ventricular hypertrophy, more preferably from hypertrophic cardiomyopathy (HCM), and most preferably from non-obstructive hypertrophic cardiomyopathy (nHCM) or obstructive hypertrophic cardiomyopathy (oHCM).

The present disclosure further relates to a method for inhibiting myosin comprising administering to a patient in need thereof a therapeutically effective amount of the compounds of general formula (I), general formula (I-1), general formula (II) and general formula (II-1) and the compounds shown in Table A or pharmaceutically acceptable salts thereof, or the pharmaceutical composition comprising the same.

The present disclosure further relates to a method for treating a disease or condition comprising administering to a patient in need thereof a therapeutically effective amount of the compounds of general formula (I), general formula (I-1), general formula (II) and general formula (II-1) and the compounds shown in Table A or pharmaceutically acceptable salts thereof, or the pharmaceutical composition comprising the same, wherein the disease or condition is selected from the group consisting of diastolic heart failure with preserved ejection fraction, ischemic heart disease, angina pectoris, restrictive cardiomyopathy, diastolic dysfunction, hypertrophic cardiomyopathy (HCM), heart failure with preserved ejection fraction (HFpEF), heart failure with mid-range ejection fraction (HFmREF), valvular diseases, aortic stenosis, inflammatory cardiomyopathy, Löeffler endocarditis, endomyocardial fibrosis, infiltrative cardiomyopathy, hemochromatosis, Fabry disease, glycogen storage disease, congenital heart defect, tetralogy of Fallot, left ventricular hypertrophy, refractory angina and Chagas disease, preferably from the group consisting of ischemic heart disease, restrictive cardiomyopathy, hypertrophic cardiomyopathy (HCM), inflammatory cardiomyopathy, infiltrative cardiomyopathy, congenital heart defect and left ventricular hypertrophy, more preferably from hypertrophic cardiomyopathy (HCM), and most preferably from non-obstructive hypertrophic cardiomyopathy (nHCM) or obstructive hypertrophic cardiomyopathy (oHCM).

The present disclosure further relates to a method for treating a myosin-mediated disease or condition comprising administering to a patient in need thereof a therapeutically effective amount of the compounds of general formula (I), general formula (I-1), general formula (II) and general formula (II-1) and the compounds shown in Table A or pharmaceutically acceptable salts thereof, or the pharmaceutical composition comprising the same, wherein the disease or condition is selected from the group consisting of diastolic heart failure with preserved ejection fraction, ischemic heart disease, angina pectoris, restrictive cardiomyopathy, diastolic dysfunction, hypertrophic cardiomyopathy (HCM), heart failure with preserved ejection fraction (HFpEF), heart failure with mid-range ejection fraction (HFmREF), valvular diseases, aortic stenosis, inflammatory cardiomyopathy, Löeffler endocarditis, endomyocardial fibrosis, infiltrative cardiomyopathy, hemochromatosis, Fabry disease, glycogen storage disease, congenital heart defect, tetralogy of Fallot, left ventricular hypertrophy, refractory angina and Chagas disease, preferably from the group consisting of ischemic heart disease, restrictive cardiomyopathy, hypertrophic cardiomyopathy (HCM), inflammatory cardiomyopathy, infiltrative cardiomyopathy, congenital heart defect and left ventricular hypertrophy, more preferably from hypertrophic cardiomyopathy (HCM), and most preferably from non-obstructive hypertrophic cardiomyopathy (nHCM) or obstructive hypertrophic cardiomyopathy (oHCM).

The present disclosure further relates to compounds of general formula (I), general formula (I-1), general formula (II) and general formula (II-1) and the compounds shown in Table A or pharmaceutically acceptable salts thereof, or a pharmaceutical composition comprising the same, for use as a medicament.

The present disclosure further relates to compounds of general formula (I), general formula (I-1), general formula (II) and general formula (II-1) and the compounds shown in Table A or pharmaceutically acceptable salts thereof, or a pharmaceutical composition comprising the same, for use as a myosin inhibitor.

The present disclosure further relates to compounds of general formula (I), general formula (I-1), general formula (II) and general formula (II-1) and the compounds shown in Table A or pharmaceutically acceptable salts thereof, or a pharmaceutical composition comprising the same, for use in treating a disease or condition selected from the group consisting of diastolic heart failure with preserved ejection fraction, ischemic heart disease, angina pectoris, restrictive cardiomyopathy, diastolic dysfunction, hypertrophic cardiomyopathy (HCM), heart failure with preserved ejection fraction (HFpEF), heart failure with mid-range ejection fraction (HFmREF), valvular diseases, aortic stenosis, inflammatory cardiomyopathy, Löeffler endocarditis, endomyocardial fibrosis, infiltrative cardiomyopathy, hemochromatosis, Fabry disease, glycogen storage disease, congenital heart defect, tetralogy of Fallot, left ventricular hypertrophy, refractory angina and Chagas disease, preferably from the group consisting of ischemic heart disease, restrictive cardiomyopathy, hypertrophic cardiomyopathy (HCM), inflammatory cardiomyopathy, infiltrative cardiomyopathy, congenital heart defect and left ventricular hypertrophy, more preferably from hypertrophic cardiomyopathy (HCM), and most preferably from non-obstructive hypertrophic cardiomyopathy (nHCM) or obstructive hypertrophic cardiomyopathy (oHCM).

The present disclosure further relates to compounds of general formula (I), general formula (I-1), general formula (II) and general formula (II-1) and the compounds shown in Table A or pharmaceutically acceptable salts thereof, or a pharmaceutical composition comprising the same, for use in treating a myosin-mediated disease or condition, wherein the disease or condition is selected from the group consisting of diastolic heart failure with preserved ejection fraction, ischemic heart disease, angina pectoris, restrictive cardiomyopathy, diastolic dysfunction, hypertrophic cardiomyopathy (HCM), heart failure with preserved ejection fraction (HFpEF), heart failure with mid-range ejection fraction (HFmREF), valvular diseases, aortic stenosis, inflammatory cardiomyopathy, Löeffler endocarditis, endomyocardial fibrosis, infiltrative cardiomyopathy, hemochromatosis, Fabry disease, glycogen storage disease, congenital heart defect, tetralogy of Fallot, left ventricular hypertrophy, refractory angina and Chagas disease, preferably from the group consisting of ischemic heart disease, restrictive cardiomyopathy, hypertrophic cardiomyopathy (HCM), inflammatory cardiomyopathy, infiltrative cardiomyopathy, congenital heart defect and left ventricular hypertrophy, more preferably from hypertrophic cardiomyopathy (HCM), and most preferably from non-obstructive hypertrophic cardiomyopathy (nHCM) or obstructive hypertrophic cardiomyopathy (oHCM).

The compounds of general formula (I), general formula (I-1), general formula (II) and general formula (II-1) disclosed herein and the compounds shown in Table A or pharmaceutically acceptable salts thereof, or the pharmaceutical composition comprising the same, can change the natural history of HCM and other diseases rather than merely relieve symptoms. The mechanisms that confer clinical benefit to HCM patients can extend to patients with other forms of heart disease that share similar pathophysiology, with or without significant genetic influence. For example, an effective treatment for HCM, by improving ventricular relaxation during diastole, can also be effective in a broader population characterized by diastolic dysfunction.

The compounds of general formula (I), general formula (I-1), general formula (II) and general formula (II-1) disclosed herein and the compounds shown in Table A or pharmaceutically acceptable salts thereof, or the pharmaceutical composition comprising the same, can specifically target the root causes of conditions or act on other downstream pathways. Accordingly, the compounds of general formula (I), general formula (I-1), general formula (II) and general formula (II-1) disclosed herein and the compounds shown in Table A or pharmaceutically acceptable salts thereof, or the pharmaceutical composition comprising the same, can confer benefit to patients suffering from diastolic heart failure with preserved ejection fraction, ischemic heart disease, angina pectoris or restrictive cardiomyopathy.

The compounds of general formula (I), general formula (I-1), general formula (II) and general formula (II-1) disclosed herein and the compounds shown in Table A or pharmaceutically acceptable salts thereof, or the pharmaceutical composition comprising the same, can also promote beneficial ventricular remodeling of left ventricular hypertrophy due to volume or pressure overload; e.g., chronic mitral regurgitation, chronic aortic stenosis or chronic systemic hypertension; the compounds and pharmaceutically acceptable salts thereof are used in combination with therapies aimed at correcting or alleviating the main cause of volume or pressure overload (valve repair/replacement, effective antihypertensive therapy). By reducing the left ventricular filling pressure, the compounds can reduce the risk of pulmonary edema and respiratory failure. Reducing or eliminating functional mitral regurgitation and/or lowering the left atrial pressure can reduce the risk of paroxysmal or permanent atrial fibrillation, and it reduces the attendant risk of arterial thromboembolic complications including but not limited to cerebral arterial embolic stroke. Reducing or eliminating dynamic and/or static left ventricular outflow obstruction can reduce the likelihood of requiring septal ablation therapy (surgical or percutaneous) and their attendant risks of short-term and long-term complications.

The compounds of general formula (I), general formula (I-1), general formula (II) and general formula (II-1) disclosed herein and the compounds shown in Table A or pharmaceutically acceptable salts thereof, or the pharmaceutical composition comprising the same, can reduce the severity of the HCM-related chronic ischemic state and thereby the risk of sudden cardiac death (SCD) or its equivalents in patients with implantable cardioverter-defibrillators (frequent and/or repeated ICD discharges) and/or the need for potentially toxic antiarrhythmic drugs.

The compounds of general formula (I), general formula (I-1), general formula (II) and general formula (II-1) disclosed herein and the compounds shown in Table A or pharmaceutically acceptable salts thereof, or the pharmaceutical composition comprising the same, may be valuable in reducing or eliminating the need for concomitant drugs (with their attendant potential toxicities, drug-drug interactions and/or side effects).

The compounds of general formula (I), general formula (I-1), general formula (II) and general formula (II-1) disclosed herein and the compounds shown in Table A or pharmaceutically acceptable salts thereof, or the pharmaceutical composition comprising the same, can reduce interstitial myocardial fibrosis and/or slow the progression, and arrest or reverse left ventricular hypertrophy.

Compound MYK-461

(MYK-461

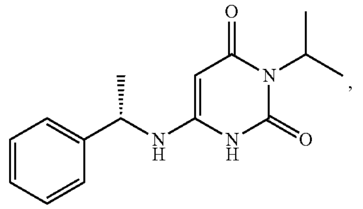

Example 1 of WO2014205223A1) has a longer $T_{1/2}$, so the accumulation is more serious clinically, and the clinical administration needs to be constantly adjusted, which increases the medication risk. In comparison, the compound of Example 16 of the present disclosure has a significantly shorter $T_{1/2}$. In addition, the compound of Example 16 of the present disclosure did not show significant accumulation in rats after 14 days of repeated intragastric administration, while compound MYK-461 did. In an experiment for identifying reactive metabolites in human liver microsomes, no glutathione (GSH) conjugate associated with the compound of Example 16 of the present disclosure was detected, but a GSH conjugate associated with compound MYK-461 was detected. It can be seen that the compound of Example 16 of the present disclosure has significant pharmacokinetic and toxicokinetic advantages over compound MYK-461 and thus is safer.

The active compound may be formulated into a form suitable for administration by any suitable route, and one or more pharmaceutically acceptable carriers are used to formulate the composition of the present disclosure by conventional methods. Thus, the active compound of the present disclosure may be formulated into a variety of dosage forms for oral administration, administration by injection (e.g., intravenous, intramuscular or subcutaneous), or administration by inhalation or insufflation. The compound of the present disclosure may also be formulated into a sustained-release dosage form, such as tablets, hard or soft capsules, aqueous or oily suspensions, emulsions, injections, dispersible powders or granules, suppositories, lozenges or syrups.

As a general guide, the active compound is preferably in a form of a unit dose, or in a form of a single dose that can be self-administered by a patient. The unit dose of the compound or composition of the present disclosure may be in a tablet, capsule, cachet, vial, powder, granule, lozenge, suppository, regenerating powder or liquid formulation. A suitable unit dose may be 0.1-1000 mg.

The pharmaceutical composition of the present disclosure may comprise, in addition to the active compound, one or more auxiliary materials selected from the group consisting of a filler (diluent), a binder, a wetting agent, a disintegrant, an excipient and the like. Depending on the method of administration, the composition may comprise 0.1 wt. % to 99 wt. % of the active compound.

The tablet comprises the active ingredient and a non-toxic pharmaceutically acceptable excipient that is used for mixing and is suitable for the preparation of the tablet. Such an excipient may be an inert excipient, a granulating agent, a disintegrant, a binder and a lubricant. Such a tablet may be uncoated or may be coated by known techniques for masking the taste of the drug or delaying the disintegration and absorption of the drug in the gastrointestinal tract and thus enabling sustained release of the drug over a longer period.

An oral formulation in a soft gelatin capsule where the active ingredient is mixed with an inert solid diluent or with a water-soluble carrier or oil vehicle may also be provided.

An aqueous suspension comprises the active substance and an excipient that is used for mixing and is suitable for the preparation of the aqueous suspension. Such an excipient is a suspending agent, a dispersant or a wetting agent. The aqueous suspension may also comprise one or more preservatives, one or more colorants, one or more corrigents and one or more sweeteners.

An oil suspension may be formulated by suspending the active ingredient in a vegetable oil, or in a mineral oil. The oil suspension may comprise a thickening agent. The sweeteners and corrigents described above may be added to provide a palatable formulation. Antioxidants may also be added to preserve the compositions.

The pharmaceutical composition of the present disclosure may also be in the form of an oil-in-water emulsion. The oil phase may be a vegetable oil or a mineral oil, or a mixture thereof. Suitable emulsifiers may be naturally occurring phospholipids, and the emulsion may also comprise a sweetener, a corrigent, a preservative and an antioxidant. Such a formulation may also comprise a palliative, a preservative, a colorant and an antioxidant. The pharmaceutical composition of the present disclosure may be in the form of a sterile injectable aqueous solution. Acceptable vehicles or solvents that can be used include water, Ringer's solution and isotonic sodium chloride solution. A sterile injectable formulation may be a sterile injectable oil-in-water microemulsion in which an active ingredient is dissolved in an oil phase. The injection or microemulsion can be locally injected into the bloodstream of a patient in large quantities. Alternatively, it may be desirable to administer the solution and microemulsion in such a way as to maintain a constant circulating concentration of the compound of the present disclosure. To maintain such a constant concentration, a continuous intravenous delivery device may be used. An example of such a device is a Deltec CADD-PLUS™ 5400 intravenous injection pump.

The pharmaceutical composition of the present disclosure may be in the form of a sterile injectable aqueous or oil suspension for intramuscular and subcutaneous administration. The suspension can be prepared according to the prior art using those suitable dispersants or wetting agents and suspending agents as described above. The sterile injectable formulation may also be a sterile injection or suspension prepared in a parenterally acceptable non-toxic diluent or solvent. In addition, a sterile fixed oil may be conventionally used as a solvent or a suspending medium. For this purpose, any blend fixed oil may be used. In addition, fatty acids may also be used to prepare injections.

The compound of the present disclosure may be administered in the form of a suppository for rectal administration. Such a pharmaceutical composition can be prepared by mixing a drug with a suitable non-irritating excipient which is a solid at ambient temperature but a liquid in the rectum and therefore will melt in the rectum to release the drug.

The compound of the present disclosure can be administered in the form of dispersible powders and granules that are formulated into aqueous suspensions by adding water. Such a pharmaceutical composition can be prepared by mixing the active ingredient with a dispersant or a wetting agent, a suspending agent, or one or more preservatives.

As is well known to those skilled in the art, the dose of the drug administered depends on a variety of factors, including but not limited to, the activity of the particular compound used, the age of the patient, the body weight of the patient, the health condition of the patient, the behavior of the patient, the diet of the patient, the time of administration, the route of administration, the rate of excretion, the combination of drugs, the severity of the disease, and the like. In addition, the optimal treatment regimen, such as the mode of administration, the daily dose of the compound or the type of pharmaceutically acceptable salts, can be verified according to conventional treatment regimens.

Description of the Terms

Unless otherwise stated, the terms used in the specification and claims have the following meanings.

The term "alkyl" refers to a saturated straight-chain or branched-chain aliphatic hydrocarbon group containing 1 to 20 (e.g., 1, 2, 3, 4, 5, 6, 7, 8, 9, 10, 11, 12, 13, 14, 15, 16, 17, 18, 19 or 20) carbon atoms (i.e., $C_{1-20}$ alkyl). The alkyl is preferably an alkyl group containing 1 to 12 carbon atoms (i.e., $C_{1-12}$ alkyl), more preferably an alkyl group containing 1 to 6 carbon atoms (i.e., $C_{1-6}$ alkyl). Non-limiting examples of alkyl include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, and the like. Most preferred is a lower alkyl group containing 1 to 6 carbon atoms; non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, I-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. Alkyl may be substituted or unsubstituted. When substituted, it may be substituted at any accessible connection site, and the substituent is preferably selected from one or more of a D atom, halogen, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkylene" refers to a divalent alkyl group, wherein the alkyl is as defined above; it contains 1 to 20 (e.g., 1, 2, 3, 4, 5, 6, 7, 8, 9, 10, 11, 12, 13, 14, 15, 16, 17, 18, 19 or 20) carbon atoms (i.e., $C_{1-20}$ alkylene). The alkylene is preferably an alkylene group containing 1 to 12 carbon atoms (i.e., $C_{1-12}$ alkylene), and more preferably an alkylene group containing 1 to 6 carbon atoms (i.e., $C_{1-6}$ alkylene). Non-limiting examples of alkylene include, but are not limited to, methylene ($-CH_2-$), 1,1-ethylene ($-CH(CH_3)-$), 1,2-ethylene ($-CH_2CH_2-$), 1,1-propylene ($-CH(CH_2CH_3)-$), 1,2-propylene ($-CH_2CH(CH_3)-$), 1,3-propylene ($-CH_2CH_2CH_2-$), 1,4-butylene ($-CH_2CH_2CH_2CH_2-$), and the like. Alkylene may be substituted or unsubstituted. When substituted, it may be substituted at any accessible connection site, and the substituent is preferably selected from one or more of alkenyl, alkynyl, alkoxy, haloalkoxy, cycloalkyloxy, heterocyclyloxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkenyl" refers to an alkyl group containing at least one carbon-carbon double bond in the molecule, wherein the alkyl is as defined above; it is preferably an alkenyl group containing 2 to 12 (e.g., 2, 3, 4, 5, 6, 7, 8, 9, 10, 11 or 12) carbon atoms (i.e., $C_{2-12}$ alkenyl). The alkenyl is preferably an alkenyl group containing 2 to 6 carbon atoms (i.e., $C_{2-6}$ alkenyl). Non-limiting examples include ethenyl, propenyl, isopropenyl, butenyl, and the like. Alkenyl may be substituted or unsubstituted. When it is substituted, the substituent is preferably selected from one or more of alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkynyl" refers to an alkyl group containing at least one carbon-carbon triple bond in the molecule, wherein the alkyl is as defined above; it is an alkynyl group containing 2 to 12 (e.g., 2, 3, 4, 5, 6, 7, 8, 9, 10, 11 or 12) carbon atoms (i.e., $C_{2-12}$ alkynyl). The alkynyl is preferably an alkynyl group containing 2 to 6 carbon atoms (i.e., $C_{2-6}$ alkynyl). Non-limiting examples include ethynyl, propynyl, butynyl, pentynyl, hexynyl, and the like. Alkynyl may be substituted or unsubstituted. When it is substituted, the substituent is preferably selected from one or more of alkoxy, halogen, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "alkoxy" refers to —O-(alkyl), wherein the alkyl is as defined above. Non-limiting examples include methoxy, ethoxy, propoxy, butoxy, and the like. Alkoxy may be substituted or unsubstituted. When substituted, it may be substituted at any accessible connection site, and the substituent is preferably selected from one or more of a D atom, halogen, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "cycloalkyl" refers to a saturated or partially unsaturated monocyclic or polycyclic hydrocarbon substituent, and the cycloalkyl ring contains 3 to 20 (e.g., 3, 4, 5, 6, 7, 8, 9, 10, 11, 12, 13, 14, 15, 16, 17, 18, 19 or 20) carbon atoms (i.e., 3- to 20-membered cycloalkyl), preferably 3 to 12 carbon atoms (i.e., 3- to 12-membered cycloalkyl), preferably 3 to 8 carbon atoms (i.e., 3- to 8-membered cycloalkyl), and more preferably 3 to 6 carbon atoms (i.e., 3- to 6-membered cycloalkyl). Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), and it may contain one or more double bonds. It is preferably 6- to 14-membered, and more preferably 7- to 10-membered (e.g., 7-membered, 8-membered, 9-membered or 10-membered). According to the number of the spiro atoms shared among the rings, the spiro cycloalkyl may be monospiro cycloalkyl or polyspiro cycloalkyl (e.g., bispiro cycloalkyl), preferably monospiro cycloalkyl and bispiro cycloalkyl, and more preferably 3-membered/5-membered, 3-membered/6-membered, 4-membered/4-membered, 4-membered/5-membered, 4-membered/6-membered, 5-membered/5-membered, 5-membered/6-membered, 6-membered/6-membered, 6-membered/4-membered or 6-membered/5-membered monospiro cycloalkyl. Non-limiting examples of spiro cycloalkyl include:

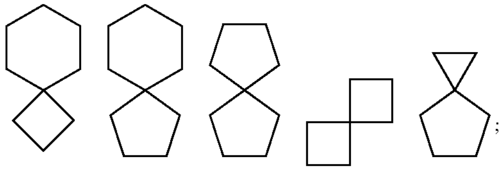;

the connection point could be at any position.

The term "fused cycloalkyl" refers to a 5- to 20-membered all-carbon polycyclic group in which rings share a pair of adjacent carbon atoms, wherein one or more rings may contain one or more double bonds. It is preferably 6- to 14-membered, and more preferably 7- to 10-membered (e.g., 7-membered, 8-membered, 9-membered or 10-membered). According to the number of constituent rings, the fused cycloalkyl may be bicyclic, tricyclic, tetracyclic, etc., preferably bicyclic or tricyclic, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 5-membered/7-membered, 6-membered/3-membered, 6-membered/4-membered, 6-membered/5-membered, 6-membered/6-membered, 6-membered/7-membered, 7-membered/5-membered or 7-membered/6-membered bicyclic alkyl. Non-limiting examples of fused cycloalkyl include:

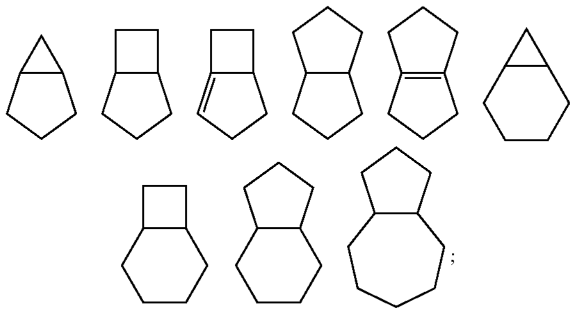

;

the connection point could be at any position.

The term "bridged cycloalkyl" refers to a 5- to 20-membered all-carbon polycyclic group in which any two rings share two carbon atoms that are not directly connected, and it may contain one or more double bonds. It is preferably 6- to 14-membered, and more preferably 7- to 10-membered (e.g., 7-membered, 8-membered, 9-membered or 10-membered). According to the number of constituent rings, the bridged cycloalkyl may be bicyclic, tricyclic, tetracyclic, etc., preferably bicyclic, tricyclic or tetracyclic, and more preferably bicyclic or tricyclic. Non-limiting examples of bridged cycloalkyl include:

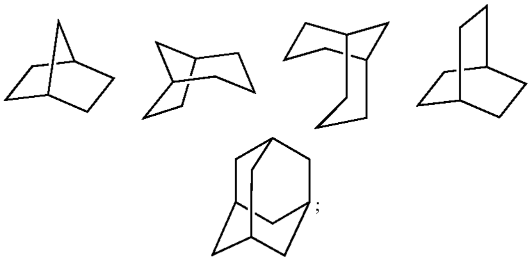

;

the connection point could be at any position.

The cycloalkyl ring includes those in which the cycloalkyl described above (including monocyclic, spiro, fused and bridged ones) fuses with an aryl, heteroaryl or heterocycloalkyl ring, wherein the ring connected to the parent structure is cycloalkyl; non-limiting examples include

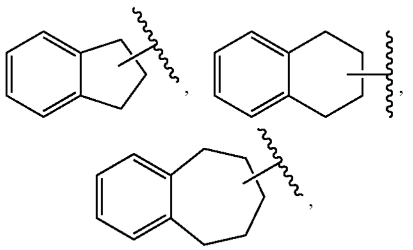

etc., preferably

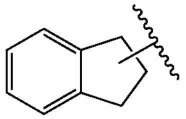

and

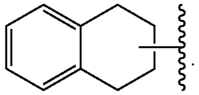

.

Cycloalkyl may be substituted or unsubstituted. When substituted, it may be substituted at any accessible connection site, and the substituent is preferably selected from one or more of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl. The term "heterocyclyl" refers to a saturated or partially unsaturated monocyclic or polycyclic substituent containing 3 to 20 ring atoms, of which one or more are heteroatoms selected from the group consisting of nitrogen, oxygen and sulfur, and the sulfur may optionally be substituted with oxo (i.e., to form sulfoxide or sulfone), but excluding a cyclic portion of —O—O—, —O—S— or —S—S—; the other ring atoms are carbon. Preferably, it contains 3 to 12 (e.g. 3, 4, 5, 6, 7, 8, 9, 10, 11 or 12) ring atoms, of which 1-4 (e.g. 1, 2, 3 and 4) are heteroatoms (i.e. 3- to 12-membered heterocyclyl); more preferably, it contains 3 to 8 ring atoms (e.g., 3, 4, 5, 6, 7 and 8), of which 1-3 are heteroatoms (e.g., 1, 2 and 3) (i.e., 3- to 8-membered heterocyclyl); more preferably, it contains 3 to 6 ring atoms, of which 1-3 are heteroatoms (i.e. 3- to 6-membered heterocyclyl); most preferably, it contains 5 or 6 ring atoms, of which 1-3 are heteroatoms (i.e. 5- or 6-membered heterocyclyl). Non-limiting examples of monocyclic heterocyclyl include pyrrolidinyl, tetrahydropyranyl, 1,2,3,6-tetrahydropyridinyl, piperidinyl, piperazinyl, morpholinyl, thiomorpholinyl, homopiperazinyl, and the like. Polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen and sulfur, and the sulfur may optionally be substituted with oxo (i.e., to form sulfoxide or sulfone); the other ring atoms are carbon. It may contain one or more double bonds. It is preferably 6- to 14-membered, and more preferably 7- to 10-membered (e.g., 7-membered, 8-membered, 9-membered or 10-membered). According to the number of spiro atoms shared among the rings, the spiro heterocyclyl may be monospiro heterocyclyl or polyspiro heterocyclyl (e.g., bispiro heterocyclyl), preferably monospiro heterocyclyl and bispiro heterocyclyl, and more preferably 3-membered/5-membered, 3-membered/6-membered, 4-membered/4-membered, 4-membered/5-membered, 4-membered/6-membered, 5-membered/5-membered, 5-membered/6-membered or 6-membered/6-membered monospiro heterocyclyl. Non-limiting examples of spiro heterocyclyl include:

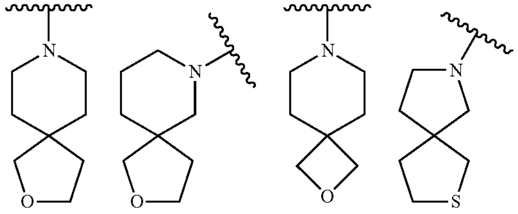

-continued

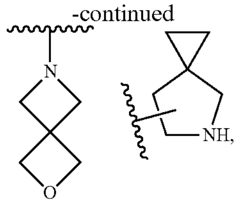

and the like.

The term "fused heterocyclyl" refers to a 5- to 20-membered polycyclic heterocyclyl group in which rings share a pair of adjacent atoms, and one or more rings may contain one or more double bonds, wherein one or more ring atoms are heteroatoms selected from the group consisting of nitrogen, oxygen and sulfur, and the sulfur may optionally be substituted with oxo (i.e., to form sulfoxide or sulfone); the other ring atoms are carbon.

It is preferably 6- to 14-membered, and more preferably 7- to 10-membered (e.g., 7-membered, 8-membered, 9-membered or 10-membered). According to the number of constituent rings, the fused heterocyclyl may be bicyclic, tricyclic, tetracyclic, etc., preferably bicyclic or tricyclic, and more preferably 3-membered/4-membered, 3-membered/5-membered, 3-membered/6-membered, 4-membered/4-membered, 4-membered/5-membered, 4-membered/6-membered, 5-membered/3-membered, 5-membered/4-membered, 5-membered/5-membered, 5-membered/6-membered, 6-membered/3-membered, 6-membered/4-membered, 6-membered/5-membered, 6-membered/6-membered, 6-membered/7-membered, 7-membered/5-membered or 7-membered/6-membered bicyclic fused heterocyclyl. Non-limiting examples of fused heterocyclyl include:

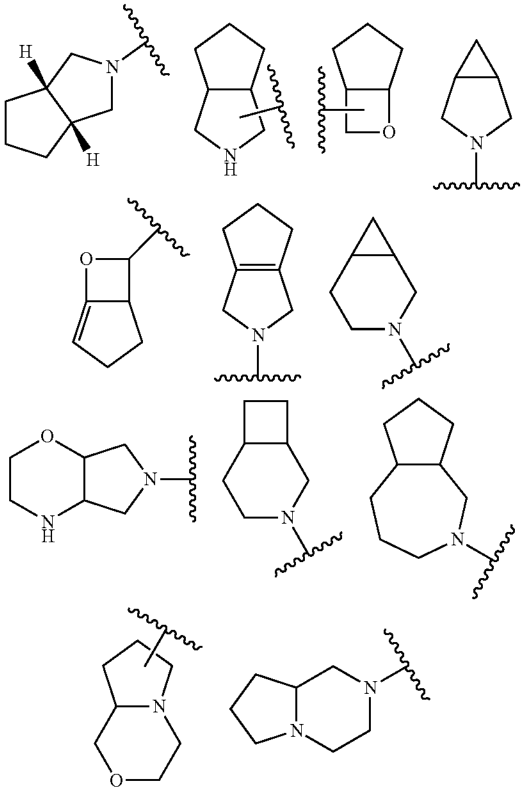

-continued

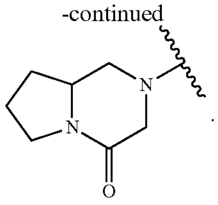

and the like.

The term "bridged heterocyclyl" refers to a 5- to 14-membered polycyclic heterocyclyl group in which any two rings share two atoms that are not directly connected, and it may contain one or more double bonds, wherein one or more ring atoms are heteroatoms selected from the group consisting of nitrogen, oxygen and sulfur, and the sulfur may optionally be substituted with oxo (i.e., to form sulfoxide or sulfone); the other ring atoms are carbon. It is preferably 6- to 14-membered, and more preferably 7- to 10-membered (e.g., 7-membered, 8-membered, 9-membered or 10-membered). According to the number of constituent rings, the bridged heterocyclyl may be bicyclic, tricyclic, tetracyclic, etc., preferably bicyclic, tricyclic or tetracyclic, and more preferably bicyclic or tricyclic. Non-limiting examples of bridged heterocyclyl include:

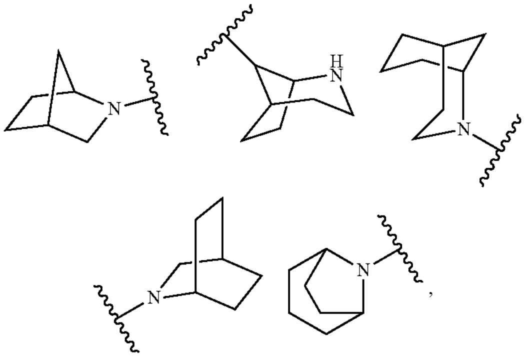

and the like.

The heterocyclyl ring includes those in which the heterocyclyl described above (including monocyclic, spiro, fused and bridged ones) fuses with an aryl, heteroaryl or cycloalkyl ring, wherein the ring connected to the parent structure is heterocyclyl; its non-limiting examples include:

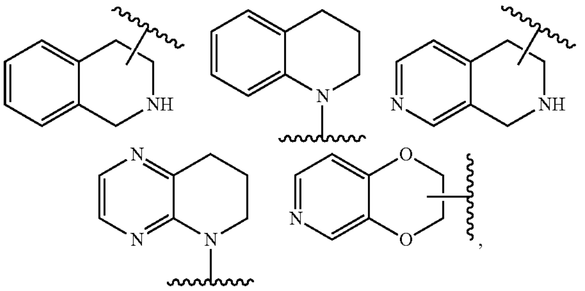

and the like.

Heterocyclyl may be substituted or unsubstituted. When substituted, it may be substituted at any accessible connection site, and the substituent is preferably selected from one or more of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl. The term "aryl" refers to a 6- to 14-membered, preferably 6- to 10-membered all-carbon monocyclic or fused polycyclic (in which the rings share a pair of adjacent carbon atoms) group having a conjugated π-electron system, e.g., phenyl and naphthyl. The aryl ring includes those in which the aryl ring described above fuses with a heteroaryl, heterocyclyl or cycloalkyl ring, wherein the ring connected to the parent structure is the aryl ring; its non-limiting examples include:

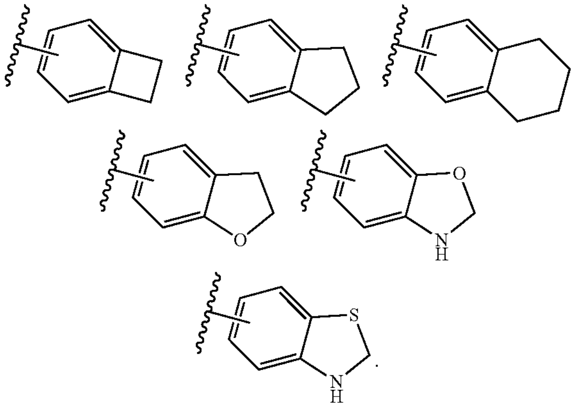

Aryl may be substituted or unsubstituted. When substituted, it may be substituted at any accessible connection site, and the substituent is preferably selected from one or more of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl.

The term "heteroaryl" refers to a heteroaromatic system containing 1 to 4 (e.g., 1, 2, 3 and 4) heteroatoms and 5 to 14 ring atoms, wherein the heteroatoms are selected from the group consisting of oxygen, sulfur and nitrogen. The heteroaryl is preferably 5- to 10-membered (e.g., 5-membered, 6-membered, 7-membered, 8-membered, 9-membered or 10-membered) and more preferably 5-membered or 6-membered, e.g., furyl, thienyl, pyridinyl, pyrrolyl, N-alkylpyrrolyl, pyridonyl, N-alkylpyridone (such as

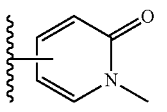
), pyrimidinyl, pyrazinyl, pyridazinyl, imidazolyl, pyrazolyl, triazolyl and tetrazolyl. The heteroaryl ring includes those in which the heteroaryl ring described above fuses with an aryl, heterocyclyl or cycloalkyl ring, wherein the ring connected to the parent structure is the heteroaryl ring; its non-limiting examples include:

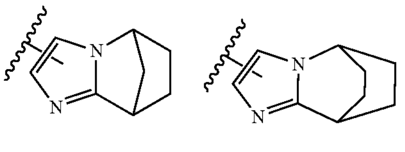

-continued

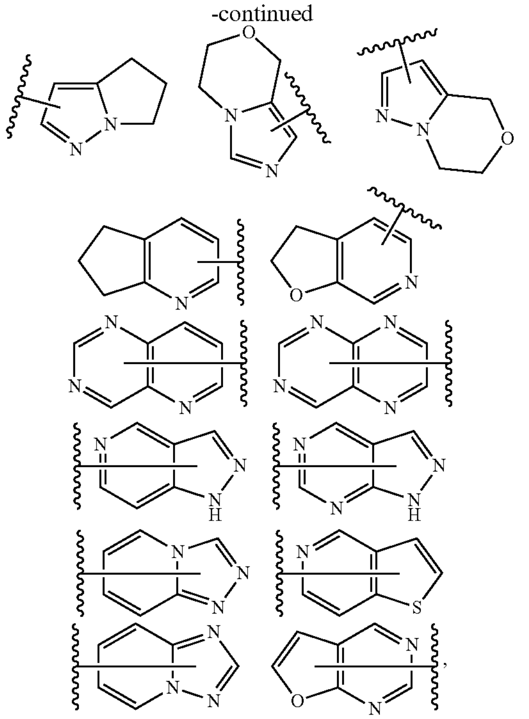
, and the like.

Heteroaryl may be substituted or unsubstituted. When substituted, it may be substituted at any accessible connection site, and the substituent is preferably selected from one or more of halogen, alkyl, alkoxy, haloalkyl, haloalkoxy, cycloalkyloxy, heterocyclyloxy, hydroxy, hydroxyalkyl, cyano, amino, nitro, cycloalkyl, heterocyclyl, aryl and heteroaryl. The cycloalkyl, heterocyclyl, aryl and heteroaryl described above include residues derived by removal of one hydrogen atom from a ring atom of the parent structure, or residues derived by removal of two hydrogen atoms from the same ring atom or two different ring atoms of the parent structure, i.e., "cycloalkylene", "heterocyclylene", "arylene" and "heteroarylene".

The term "amino protecting group" refers to a group that is introduced onto an amino group in order for the amino group to remain unchanged when other parts of the molecule are involved in reactions, and the group can be easily removed. Non-limiting examples include (trimethylsilyl) ethoxymethyl, tetrahydropyranyl, tert-butoxycarbonyl, acetyl, benzyl, allyl, p-methoxybenzyl, and the like. These groups may be optionally substituted with 1-3 substituents selected from the group consisting of halogen, alkoxy and nitro.

The term "hydroxy protecting group" refers to a group that is generally introduced onto a hydroxy group in order to block or protect the hydroxy group when other functional groups of the compound are involved in reactions, and the group can be easily removed. Non-limiting examples include trimethylsilyl (TMS), triethylsilyl (TES), triisopropylsilyl (TIPS), tert-butyldimethylsilyl (TBS), tert-butyldiphenylsilyl, methyl, tert-butyl, allyl, benzyl, methoxymethyl (MOM), ethoxyethyl, 2-tetrahydropyranyl (THP), formyl, acetyl, benzoyl, p-nitrobenzoyl, and the like.

The term "cycloalkyloxy" refers to cycloalkyl-O—, wherein the cycloalkyl is as defined above.

The term "heterocyclyloxy" refers to heterocyclyl-O—, wherein the heterocyclyl is as defined above.

The term "aryloxy" refers to aryl-O—, wherein the aryl is as defined above.

The term "heteroaryloxy" refers to heteroaryl-O—, wherein the heteroaryl is as defined above.

The term "alkylthio" refers to alkyl-S—, wherein the alkyl is as defined above.

The term "haloalkyl" refers to alkyl substituted with one or more halogens, wherein the alkyl is as defined above.

The term "haloalkoxy" refers to alkoxy substituted with one or more halogens, wherein the alkoxy is as defined above.

The term "deuterated alkyl" refers to alkyl substituted with one or more deuterium atoms, wherein the alkyl is as defined above.

The term "hydroxyalkyl" refers to alkyl substituted with one or more hydroxy groups, wherein the alkyl is as defined above.

The term "halogen" refers to fluorine, chlorine, bromine or iodine.

The term "hydroxy" refers to —OH.

The term "sulfhydryl" refers to —SH.

The term "amino" refers to —$NH_2$.

The term "cyano" refers to —CN.

The term "nitro" refers to —$NO_2$.

The term "oxo" refers to "═O".

The term "carbonyl" refers to C═O.

The term "carboxyl" refers to —C(O)OH.

The term "carboxylate group" refers to —C(O)O(alkyl), —C(O)O(cycloalkyl), (alkyl)C(O)O— or (cycloalkyl)C(O)O—, wherein the alkyl and cycloalkyl are as defined above.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomer, (L)-isomer, and racemic mixtures and other mixtures thereof, such as enantiomerically or diastereomerically enriched mixtures, all of which are within the scope of the present disclosure. Additional asymmetric carbon atoms may be present in substituents such as an alkyl group. All such isomers and mixtures thereof are included within the scope of the present disclosure. The compounds of the present disclosure containing asymmetric carbon atoms can be isolated in optically active pure form or in racemic form. The optically active pure form can be isolated from a racemic mixture or synthesized using chiral starting materials or chiral reagents.

In the chemical structure of the compound of the present disclosure, a bond "" represents an unspecified configuration, namely if chiral isomers exist in the chemical structure, the bond "" may be "" or "", or contains both the configurations of "" and "".

In the chemical structure of the compound described herein, a "" bond is not specified with a configuration—that is, it may be in a Z configuration or an E configuration, or includes both configurations. For all carbon-carbon double bonds, both Z- and E-forms are included, even if only one configuration is named.

The compounds and intermediates of the present disclosure may also exist in different tautomeric forms, and all such forms are included within the scope of the present disclosure. The term "tautomer" or "tautomeric form" refers to structural isomers of different energies that can interconvert via a low energy barrier. For example, proton tautomers (also known as proton transfer tautomers) include interconversion via proton migration, such as keto-enol and imine-enamine, lactam-lactim isomerization. An example of a lactam-lactim equilibrium is present between A and B as shown below.

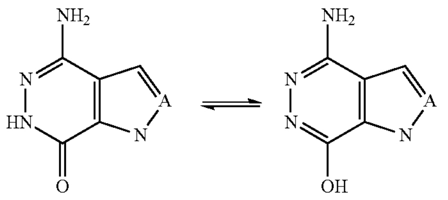

A B

All compounds in the present disclosure can be drawn as form A or form B. All tautomeric forms are within the scope of the present disclosure. The nomenclature of the compounds does not exclude any tautomers.

The present disclosure also comprises isotopically-labeled compounds which are identical to those recited herein but have one or more atoms replaced by an atom having an atomic mass or mass number different from the atomic mass or mass number usually found in nature. Examples of isotopes that can be incorporated into the compound of the present disclosure include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{3}S$, $^{18}F$, $^{123}I$, $^{125}I$ and $^{36}Cl$. Such a compound can be used as an analytical tool or a probe in, for example, a biological assay, or may be used as a tracer for in vivo diagnostic imaging of disease, or as a tracer in a pharmacodynamic, pharmacokinetic or receptor study.

The present disclosure further comprises various deuterated compounds. Each available hydrogen atom connected to a carbon atom may be independently replaced with a deuterium atom. Those skilled in the art can synthesize the compounds in deuterated form by reference to the relevant literature. Commercially available deuterated starting materials can be used in preparing the deuterated compounds, or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like. Unless otherwise stated, when a position is specifically designated as deuterium (D), that position shall be understood to be deuterium having an abundance that is at least 1000 times greater than the natural abundance of deuterium (which is 0.015%) (i.e., incorporating at least 10% deuterium). The compounds of examples comprise deuterium having an abundance that is greater than at least 1000 times the natural abundance, at least 2000 times the natural abundance, at least 3000 times the natural abundance, at least 4000 times the natural abundance, at least 5000 times the natural abundance, at least 6000 times the natural abundance, or higher times the natural abundance.

The term "optionally" or "optional" means that the event or circumstance subsequently described may, but not necessarily, occur, and that the description includes instances where the event or circumstance occurs or does not occur. For example, "$C_{1-6}$ alkyl optionally substituted with halogen or cyano" means that halogen or cyano may, but not necessarily, be present, and the description includes the instance where alkyl is substituted with halogen or cyano and the instance where alkyl is not substituted with halogen and cyano.

"Substituted" means that one or more, preferably 1 to 6, and more preferably 1 to 3 hydrogen atoms in the group are independently substituted with a corresponding number of substituents. Those skilled in the art can determine (experimentally or theoretically) possible or impossible substitution without undue effort. For example, it may be unstable when amino or hydroxy having a free hydrogen is bound to a carbon atom having an unsaturated (e.g., olefinic) bond.

The term "pharmaceutical composition" refers to a mixture containing one or more of the compounds described herein or a physiologically/pharmaceutically acceptable salt or pro-drug thereof, and other chemical components, and other components, for example, physiologically/pharmaceutically acceptable carriers and excipients. The pharmaceutical composition is intended to promote the administration to an organism, so as to facilitate the absorption of the active ingredient, thereby exerting biological activities.

The "pharmaceutically acceptable salt" refers to a salt of the compound disclosed herein, which may be selected from the group consisting of inorganic and organic salts. The salts are safe and effective for use in the body of a mammal and possess the requisite biological activity. The salts may be prepared separately during the final separation and purification of the compound, or by reacting an appropriate group with an appropriate base or acid. Bases commonly used to form pharmaceutically acceptable salts include inorganic bases such as sodium hydroxide and potassium hydroxide, and organic bases such as ammonia. Acids commonly used to form pharmaceutically acceptable salts include inorganic acids and organic acids.

For drugs or pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The term "pharmaceutically acceptable" used herein means that those compounds, materials, compositions and/or dosage forms that are, within the scope of reasonable medical judgment, suitable for use in contact with the tissues of patients without excessive toxicity, irritation, allergic reaction, or other problems or complications, and are commensurate with a reasonable benefit/risk ratio and effective for the intended use.

As used herein, the singular forms "a", "an" and "the" include plural references and vice versa, unless otherwise clearly defined in the context.

When the term "about" is applied to parameters such as pH, concentration and temperature, it means that the parameter may vary by ±10%, and sometimes more preferably within ±5%. As will be appreciated by those skilled in the art, when the parameters are not critical, the numbers are generally given for illustrative purposes only and are not intended to be limiting.

Synthesis of the Compounds of the Present Disclosure

To achieve the purpose of the present disclosure, the following technical schemes are adopted in the present disclosure:

Scheme 1

A method for preparing the compound of general formula (I) or the pharmaceutically acceptable salt thereof disclosed herein is provided, and the method comprises the following steps:

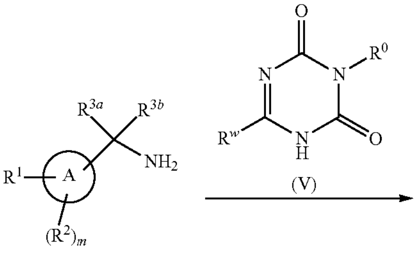

(V)

(IA)

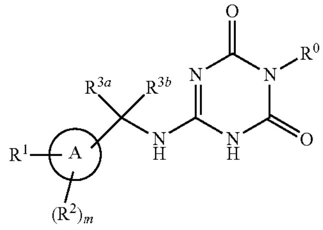

(I)

conducting, directly or in the presence of a base, a nucleophilic substitution reaction of a compound of general formula (IA) or a salt (preferably hydrochloride) thereof with a compound of general formula (V) to give the compound of general formula (I) or the pharmaceutically acceptable salt thereof;

wherein:

$R^w$ is a leaving group, preferably pyrazolyl;

ring A, $R^0$, $R^1$, $R^2$, $R^{3a}$, $R^{3b}$ and m are as defined in general formula (I).

Scheme 2

A method for preparing the compound of general formula (I-1) or the pharmaceutically acceptable salt thereof disclosed herein is provided, and the method comprises:

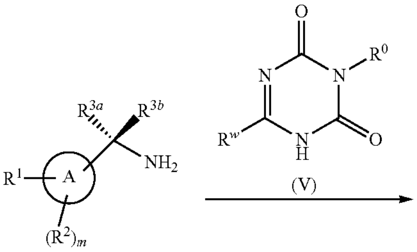

(V)

(IA-1)

-continued

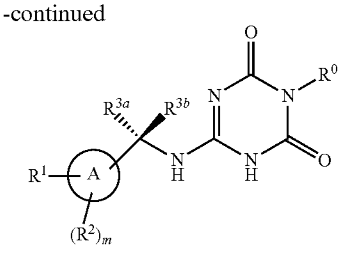

(I-1)

conducting, directly or in the presence of a base, a nucleophilic substitution reaction of a compound of general formula (IA-1) or a salt (preferably hydrochloride) thereof with a compound of general formula (V) to give the compound of general formula (I-1) or the pharmaceutically acceptable salt thereof;

wherein:

$R^w$ is a leaving group, preferably pyrazolyl;

ring A, $R^0$, $R^1$, $R^2$, $R^{3a}$, $R^{3b}$ and m are as defined in general formula (I-1).

Scheme 3

A method for preparing the compound of general formula (II) or the pharmaceutically acceptable salt thereof disclosed herein is provided, and the method comprises:

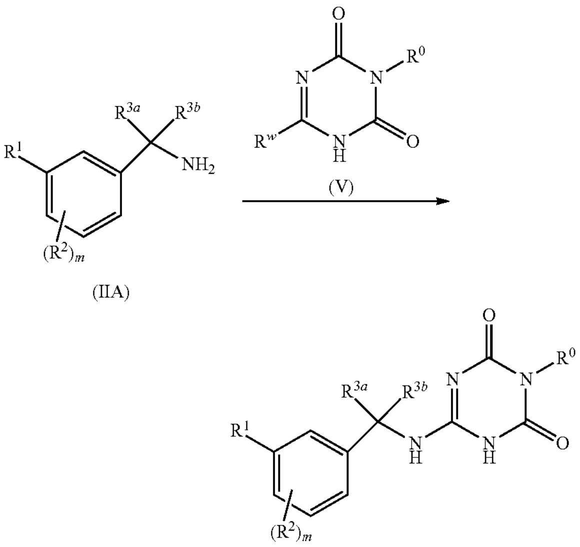

(IIA) (V) (II)

conducting, directly or in the presence of a base, a nucleophilic substitution reaction of a compound of general formula (IIA) or a salt (preferably hydrochloride) thereof with a compound of general formula (V) to give the compound of general formula (II) or the pharmaceutically acceptable salt thereof;

wherein:

$R^w$ is a leaving group, preferably pyrazolyl;

$R^0$, $R^1$, $R^2$, $R^{3a}$, $R^{3b}$ and m are as defined in general formula (II).

Scheme 4

A method for preparing the compound of general formula (II-1) or the pharmaceutically acceptable salt thereof disclosed herein is provided, and the method comprises:

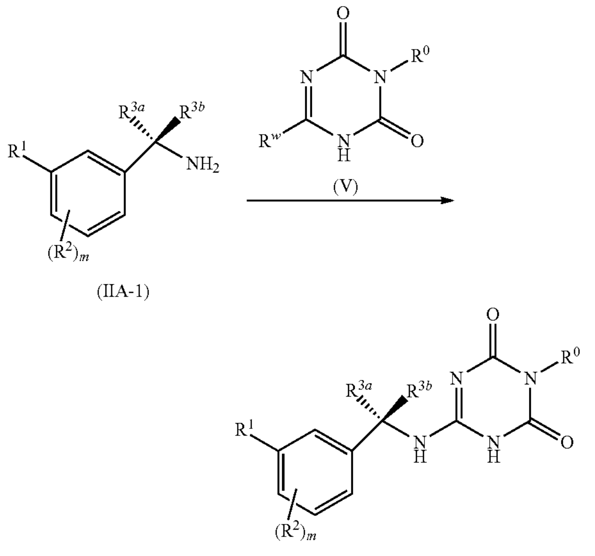

(IIA-1) (V) (II-1)

conducting, directly or in the presence of a base, a nucleophilic substitution reaction of a compound of general formula (IIA-1) or a salt (preferably hydrochloride) thereof with a compound of general formula (V) to give the compound of general formula (II-1) or the pharmaceutically acceptable salt thereof;

wherein:

$R^w$ is a leaving group, preferably pyrazolyl;

$R^0$, $R^1$, $R^2$, $R^{3a}$, $R^{3b}$ and m are as defined in general formula (II-1).

In the above schemes, the base includes organic bases and inorganic bases; the organic bases include, but are not limited to, triethylamine, N,N-diisopropylethylamine, n-butyllithium, lithium diisopropylamide, sodium acetate, potassium acetate, sodium ethoxide, sodium tert-butoxide and potassium tert-butoxide, preferably triethylamine and N,N-diisopropylethylamine; the inorganic bases include, but are not limited to, sodium hydride, potassium phosphate, sodium carbonate, potassium carbonate, cesium carbonate, sodium hydroxide, lithium hydroxide monohydrate, lithium hydroxide and potassium hydroxide.

The above reactions are preferably conducted in solvents including but not limited to N-methylpyrrolidone, ethylene glycol dimethyl ether, acetic acid, methanol, ethanol, acetonitrile, n-butanol, toluene, tetrahydrofuran, dichloromethane, petroleum ether, ethyl acetate, n-hexane, dimethyl sulfoxide, 1,4-dioxane, water, N,N-dimethylacetamide, N,N-dimethylformamide, 1,2-dibromoethane and mixtures thereof.

The nucleophilic substitution reactions are conventional reactions, and the reaction temperatures are 100-160° C., preferably 120° C.

The nucleophilic substitution reactions are conventional reactions, and the lengths of the reactions are 10-20 hours, preferably 16 hours.

The nucleophilic substitution reactions may also be conducted in microwaves, and the reaction temperatures of the microwave reactions are 100-160° C., preferably 140° C.

The nucleophilic substitution reactions may also be conducted in microwaves, and the lengths of the microwave reactions are 0.5-4 hours, preferably 2 h.

DETAILED DESCRIPTION

The present disclosure is further described below with reference to examples below, which are not intended to limit the scope of the present disclosure.

EXAMPLES

The structures of the compounds were determined by nuclear magnetic resonance (NMR) spectroscopy and/or mass spectrometry (MS). NMR shifts (δ) are given in $10^{-6}$ (ppm). NMR analyses were performed on a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as solvents and tetramethylsilane (TMS) as an internal standard.

MS analyses were performed on an Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: Waters, MS model: Waters ACQuity Qda Detector/Waters SQ Detector) and THERMO Ultimate 3000-Q Exactive (manufacturer: THERMO, MS model: THERMO Q Exactive).

High performance liquid chromatography (HPLC) analyses were performed on Agilent HPLC 1200DAD, Agilent HPLC 1200VWD and Waters HPLC e2695-2489 high performance liquid chromatographs.

Chiral HPLC analyses were performed on an Agilent 1260 DAD high performance liquid chromatograph.

Preparative HPLC was performed on Waters 2767, Waters 2767-SQ Detecor2, Shimadzu LC-20AP and Gilson-281 preparative chromatographs.

Preparative chiral chromatography was performed on a Shimadzu LC-20AP preparative chromatograph.

The CombiFlash preparative flash chromatograph used was CombiFlash Rf200 (TELEDYNE ISCO).

Yantai Huanghai HSGF254 or Qingdao GF254 silica gel plates, 0.15-0.2 mm layer thickness, were adopted for thin-layer chromatography (TLC) analysis and 0.4-0.5 mm layer thickness for TLC separation and purification.

Silica gel column chromatography generally used 200- to 300-mesh silica gel (Huanghai, Yantai) as the carrier.

The mean inhibition of kinase and the $IC_{50}$ value were determined on a NovoStar microplate reader (BMG, Germany).

The known starting materials of the present disclosure may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions could all be conducted in an argon atmosphere or a nitrogen atmosphere unless otherwise specified.

The argon atmosphere or nitrogen atmosphere means that the reaction flask is connected to a balloon containing about 1 L of argon or nitrogen.

The hydrogen atmosphere means that the reaction flask is connected to a balloon containing about 1 L of hydrogen.

Parr 3916EKX hydrogenator, Qinglan QL-500 hydrogenator or HC2-SS hydrogenator was used in the pressurized hydrogenation reactions.

Hydrogenation reactions generally involve 3 cycles of vacuumization and hydrogen purging.

A CEM Discover-S 908860 microwave reactor was used in microwave reactions.

In the examples, a solution refers to an aqueous solution unless otherwise specified.

In the examples, the reaction temperature is room temperature, i.e., 20° C. to 30° C., unless otherwise specified.

The monitoring of the reaction progress in the examples was conducted by thin-layer chromatography (TLC). The developing solvent for reactions, the eluent system for column chromatography purification and the developing solvent system for thin layer chromatography included: A: n-hexane/ethyl acetate system, and B: dichloromethane/methanol system. The volume ratio of the solvents was adjusted according to the polarity of the compound, or by adding a small amount of basic or acidic reagents such as triethylamine and acetic acid.

Example 1

6-(((S)-1-(2-Fluoro-5-(((S)-tetrahydrofuran-3-yl)oxy)phenyl)ethyl)amino)-3-isopropyl-1,3,5-triazine-2,4(1H,3H)-dione 1

1

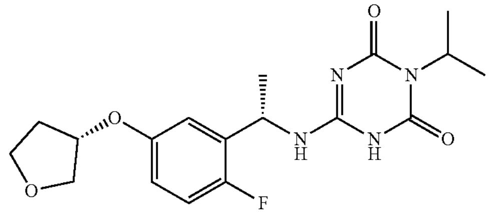

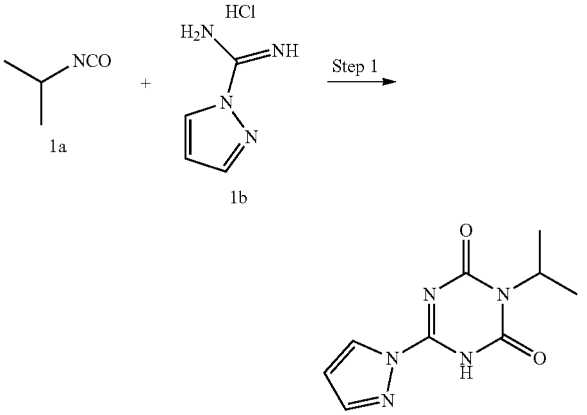

1a

1b

1c

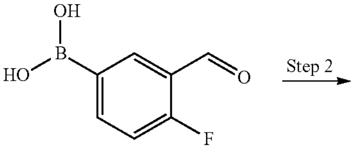

1d

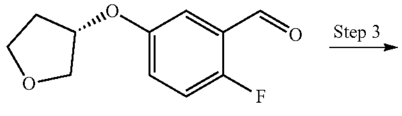

1e

-continued

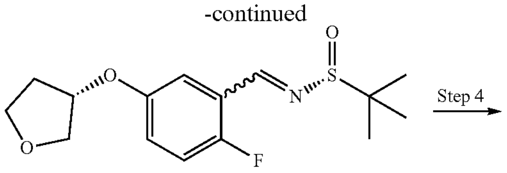

1f

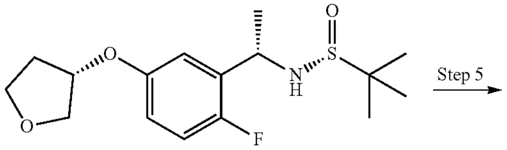

1g

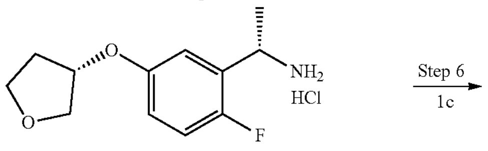

1h

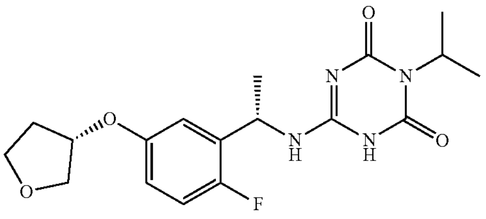

1

Step 1

3-Isopropyl-6-(1H-pyrazol-1-yl)-1,3,5-triazine-2,4 (1H,3H)-dione 1c

2-Isocyanatopropane 1a (4.06 g, 47.71 mmol, Shanghai Titan Scientific Co., Ltd.) and 1H-pyrazole-1-carboximidamide hydrochloride 1b (6.66 g, 45.44 mmol, Bide Pharmatech Ltd.) were dissolved in N,N-dimethylacetamide (35 mL). The solution was cooled to −10° C., and 1,8-diazabicycloundec-7-ene (12.00 g, 47.65 mmol) was added dropwise over 5 min. The reaction was stirred in an ice bath for another 30 min. N,N'-Carbonyldiimidazole (9.80 g, 68.08 mmol) was added under ice bath. The mixture was cooled to −5° C., and 1,8-diazabicycloundec-7-ene (17.14 g, 68.06 mmol) was added dropwise over 10 min. The reaction was stirred in an ice bath for another 1 h. 2 N hydrochloric acid (132 mL) was added dropwise at room temperature over 30 min. The mixture was filtered, and the filter cake was collected and dried in vacuo to give the title product 1c (3.30 g, yield: 32.9%).

MS m/z (ESI): 222.0 [M+1].

Step 2

(S)-2-Fluoro-5-((tetrahydrofuran-3-yl)oxy)benzaldehyde 1e

4-Fluoro-3-formylphenylbenzeneboronic acid 1d (10.00 g, 59.55 mmol, Hanhai Chemical Co., Ltd.) and (S)-tetrahydrofuran-3-ol (15.80 g, 179.33 mmol, Accela ChemBio Inc.) were dissolved in dichloromethane (100 mL), and copper acetate (22.00 g, 121.13 mmol), pyridine (10.00 g, 126.42 mmol) and triethylamine (13.00 g, 128.71 mmol) were added. The mixture was stirred at room temperature for 24 h, filtered, and concentrated under reduced pressure. The resulting residue was purified by silica gel column chromatography with eluent system A to give the title product 1e (1.00 g, yield: 8.0%).

MS m/z (ESI): 211.0 [M+1].

Step 3

(R)—N-(2-Fluoro-5-(((S)-tetrahydrofuran-3-yl)oxy) benzylidene)-2-methylpropane-2-sulfinamide 1f Compound 1e (1.00 g, 4.76 mmol) and (R)-2-methylpropane-2-sulfinamide (580 mg, 4.78 mmol, Bide Pharmatech Ltd.) were dissolved in dichloromethane (20 mL), and cesium carbonate (1.90 g, 5.83 mmol) was added. The mixture was stirred at room temperature for 16 h, filtered, and concentrated under reduced pressure to give the crude title product 1f (1.40 g, yield: 93.9%). The crude product was directly used in the next step without being purified.

MS m/z (ESI): 313.9 [M+1].

Step 4

(R)—N—((S)-1-(2-Fluoro-5-(((S)-tetrahydrofuran-3-yl)oxy)phenyl)ethyl)-2-methylpropane-2-sulfinamide 1g The crude compound 1f (100 mg, 0.32 mmol) was dissolved in dichloromethane (5 mL), and the system was purged with nitrogen three times. The reaction was cooled to −60° C., and a 3 M solution of methylmagnesium bromide in 2-methyltetrahydrofuran (0.22 mL, 0.66 mmol, Shanghai Titan Scientific Co., Ltd.) was added dropwise. The reaction was stirred at room temperature for 5 h in a nitrogen atmosphere. A saturated ammonium chloride solution (10 mL) was added, and the organic phase was separated. The aqueous phase was extracted with ethyl acetate (20 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system B to give the title product 1g (105 mg, yield: 99.9%).

MS m/z (ESI): 330.0 [M+1].

Step 5

(S)-1-(2-Fluoro-5-(((S)-tetrahydrofuran-3-yl)oxy) phenyl)ethan-1-amine hydrochloride 1h Compound 1g (105 mg, 0.32 mmol) was dissolved in ethanol (5 mL). The solution was cooled to 0° C., and thionyl chloride (101 mg, 0.85 mmol, Shanghai Hushi Chemical Co., Ltd.) was added dropwise. The reaction was stirred at room temperature for 1h. The reaction mixture was concentrated under reduced pressure to give the crude title product 1h (83 mg, yield: 99.5%). The crude product was directly used in the next step without being purified.

MS m/z (ESI): 208.9 [M−16].

Step 6

6-(((S)-1-(2-Fluoro-5-(((S)-tetrahydrofuran-3-yl) oxy)phenyl)ethyl)amino)-3-isopropyl-1,3,5-triazine-2,4(1H,3H)-dione 1

Compound 1c (70 mg, 0.32 mmol) and compound 1h (83 mg, 0.32 mmo) were dissolved in N-methylpyrrolidone (8 mL), and triethylamine (64 mg, 0.63 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 1 (6 mg, yield: 5.0%).

MS m/z (ESI): 379.0 [M+1].

$^1$H NMR (500 MHz, DMSO-$d_6$) δ 10.50 (brs, 1H), 7.66 (brs, 1H), 7.11 (m, 1H), 6.92 (m, 1H), 6.84 (m, 1H), 5.22 (m, 1H), 4.96 (m, 1H), 4.80 (m, 1H), 3.89-3.71 (m, 4H), 2.19 (m, 1H), 2.02-1.88 (m, 1H), 1.39 (d, 3H), 1.29 (d, 6H).

Example 2

6-(((S)-1-(2-Fluoro-5-(((R)-tetrahydrofuran-3-yl)oxy)phenyl)ethyl)amino)-3-isopropyl-1,3,5-triazine-2,4(1H,3H)-dione 2

2

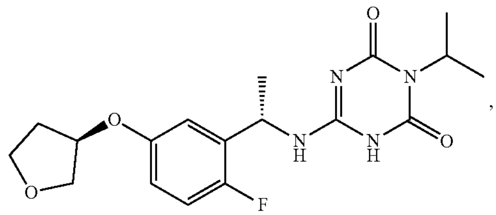

,

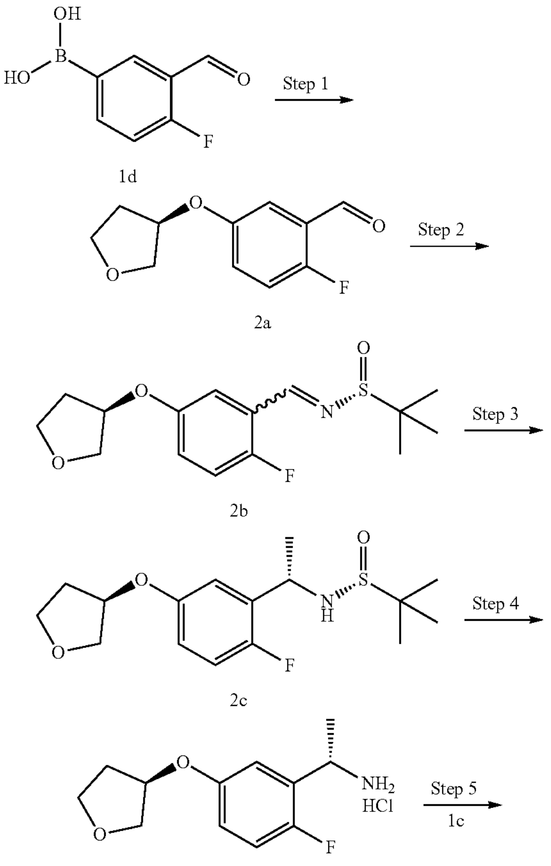

1d

2a

2b

2c

2d

-continued

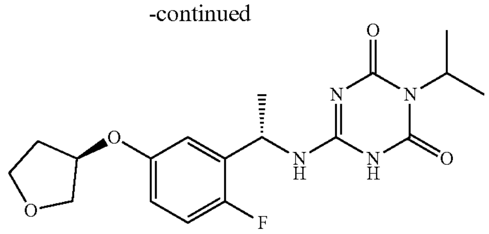

2

Step 1

(R)-2-Fluoro-5-((tetrahydrofuran-3-yl)oxy)benzaldehyde 2a

Compound 1d (10 g, 59.5 mmol) and (R)-tetrahydrofuran-3-ol (10 g, 113 mmol, Bide Pharmatech Ltd.) were dissolved in dichloromethane (100 mL), and pyridine (10 g, 126 mmol, adamas), triethylamine (13 g, 129 mmol, adamas) and anhydrous copper acetate (23 g, 127 mmol, Bide Pharmatech Ltd.) were added. The reaction was stirred for 24 h. The reaction mixture was filtered and concentrated under reduced pressure. The resulting residue was purified by silica gel column chromatography with eluent system A to give the title product 2a (1.9 g, yield: 15.2%).

MS m/z (ESI): 211.0 [M+1].

Step 2

(R)—N-(2-Fluoro-5-(((R)-tetrahydrofuran-3-yl)oxy)benzylidene)-2-methylpropane-2-sulfinamide 2b Compound 2a (1.9 g, 9.04 mmol) and (R)-2-methylpropane-2-sulfinamide (1.1 g, 9.08 mmol, adamas) were dissolved in dichloromethane (30 mL), and cesium carbonate (3.6 g, 11.4 mmol) was added. The reaction was stirred for 16 h. The reaction mixture was filtered and concentrated under reduced pressure. The resulting residue was purified by silica gel column chromatography with eluent system A to give the crude title product 2b (2.8 g, yield: 98.8%).

MS m/z (ESI): 313.9 [M+1].

Step 3

(R)—N—((S)-1-(2-Fluoro-5-(((R)-tetrahydrofuran-3-yl)oxy)phenyl)ethyl)-2-methylpropane-2-sulfinamide 2c The crude compound 2b (300 mg, 0.96 mmol) was dissolved in dichloromethane (10 mL), and the system was purged with nitrogen three times. The reaction was cooled to −60° C., and a 3 M solution of methylmagnesium bromide in 2-methyltetrahydrofuran (0.67 mL, 2.01 mmol, Shanghai Titan Scientific Co., Ltd.) was added dropwise. The reaction was stirred at room temperature for 5 h in a nitrogen atmosphere. A saturated ammonium chloride solution (10 mL) was added, and the organic phase was separated. The aqueous phase was extracted with ethyl acetate (20 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system B to give the title product 2c (315 mg, yield: 99.9%).

MS m/z (ESI): 330.0 [M+1].

Step 4

(S)-1-(2-Fluoro-5-(((R)-tetrahydrofuran-3-yl)oxy)phenyl)ethylamine hydrochloride 2d Compound 2c (315 mg, 0.96 mmol) was dissolved in ethanol (6 mL). The solution was cooled to 0° C., and thionyl chloride (303 mg, 2.55 mmol, Shanghai Hushi Chemical Co., Ltd.) was added dropwise. The reaction was stirred at room temperature for 1 h. The reaction mixture was concentrated under reduced pressure to give the crude title product 2d (250 mg, yield: 99.9%). The crude product was directly used in the next step without being purified.

MS m/z (ESI): 208.9 [M−16].

Step 5

6-(((S)-1-(2-Fluoro-5-(((R)-tetrahydrofuran-3-yl)oxy)phenyl)ethyl)amino)-3-isopropyl-1,3,5-triazine-2,4(1H,3H)-dione 2

Compound 1c (164 mg, 0.74 mmol) and compound 2d (250 mg, 0.96 mmo) were dissolved in N-methylpyrrolidone (8 mL), and triethylamine (75 mg, 0.74 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 2 (30 mg, yield: 10.7%).

MS m/z (ESI): 379.0 [M+1].

$^1$H NMR (500 MHz, DMSO-$d_6$): δ 10.52 (brs, 1H), 7.27 (brs, 1H), 7.13 (m, 1H), 6.92-6.83 (m, 2H), 5.20 (m, 1H), 4.97 (m, 1H), 4.79 (m, 1H), 3.88-3.73 (m, 4H), 2.20 (m, 1H), 1.95 (m, 1H), 1.39 (d, 3H), 1.29 (d, 6H).

Example 3

3-Isopropyl-6-(((1S)-1-(3-((tetrahydrofuran-3-yl)oxy)phenyl)ethyl)amino)-1,3,5-triazine-2,4(1H,3H)-dione 3

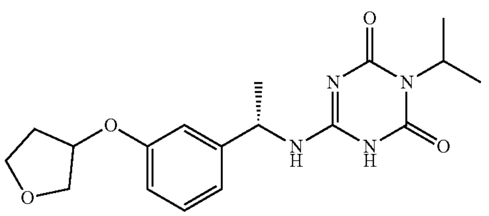

3

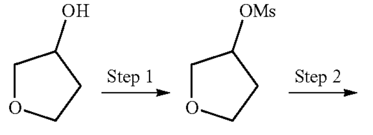

3a 3b

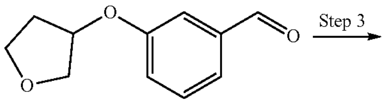

3c

-continued

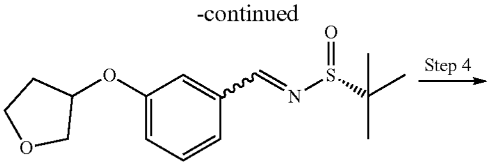

3d

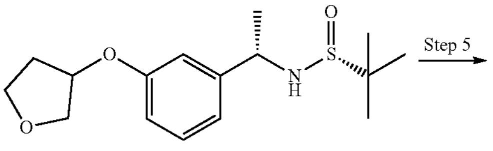

3e

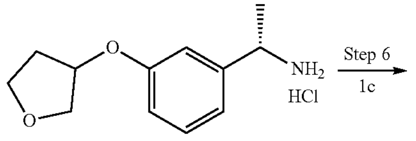

3f

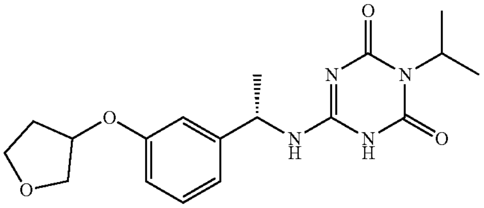

3

Step 1

Tetrahydrofuran-3-yl methanesulfonate 3b

Tetrahydrofuran-3-ol 3a (2.0 g, 22.7 mmol, Accela ChemBio Inc.) and triethylamine (3.4 g, 33.7 mmol) were dissolved in dichloromethane (20 mL), and methanesulfonyl chloride (2.84 g, 24.9 mmol, Sinopharm Chemical Reagent Co., Ltd.) was added at 0° C. The mixture was reacted at room temperature for 24 h. Water (100 mL) was added, and extraction was performed with dichloromethane (20 mL×2). The organic phases were combined and concentrated under reduced pressure. The resulting residue was purified by silica gel column chromatography with eluent system A to give the title product 3b (3.1 g, yield: 82.2%).

$^1$H NMR (500 MHz, $CDCl_3$) δ 5.34 (m, 1H), 4.06-3.89 (m, 4H), 3.06 (s, 3H), 2.29-2.24 (m, 2H).

Step 2

3-((Tetrahydrofuran-3-yl)oxy)benzaldehyde 3c

Compound 3b (700 mg, 4.21 mmol) and 3-hydroxybenzaldehyde (500 mg, 4.09 mmol, Accela ChemBio Inc.) were dissolved in N,N-dimethylformamide (10 mL), and potassium carbonate (850 mg, 6.16 mmol) was added. The mixture was reacted at 90° C. for 16 h. The reaction mixture was diluted with water (50 mL) and extracted with ethyl acetate (20 mL×2). The organic phases were combined and concentrated under reduced pressure. The resulting residue was purified by silica gel column chromatography with eluent system A to give the title product 3c (710 mg, yield: 90.2%).

MS m/z (ESI): 193.0 [M+1].

Step 3

(R)-2-Methyl-N-(3-((tetrahydrofuran-3-yl)oxy)benzylidene)propane-2-sulfinamide 3d Compound 3c (710 mg, 3.69 mmol) and (R)-2-methylpropane-2-sulfinamide (450 mg, 3.71 mmol) were dissolved in dichloromethane (10 mL), and cesium carbonate (1.5 g, 4.60 mmol) was added. The reaction was stirred for 16 h. The reaction mixture was filtered and concentrated. The resulting residue was purified by silica gel column chromatography with eluent system A to give the title product 3d (1.08 g, yield: 99.0%).

MS m/z (ESI): 296.0 [M+1].

Step 4

(R)-2-Methyl-N-((1S)-1-(3-((tetrahydrofuran-3-yl)oxy)phenyl)ethyl)propane-2-sulfinamide 3e Compound 3d (500 mg, 1.69 mmol) was dissolved in dichloromethane (10 mL). The solution was cooled to −60° C. in a nitrogen atmosphere, and a 3 M solution of methylmagnesium bromide in 2-methyltetrahydrofuran (1.2 mL, 3.6 mmol) was added dropwise. The reaction was warmed to room temperature and stirred for 16 h. A saturated aqueous ammonium chloride solution (20 mL) was added at 0° C., and the organic phase was separated. The aqueous phase was extracted with ethyl acetate (20 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system A to give the title product 3e (490 mg, yield: 92.9%).

MS m/z (ESI): 312.1 [M+1].

Step 5

(1S)-1-(3-((Tetrahydrofuran-3-yl)oxy)phenyl)ethylamine hydrochloride 3f

Compound 3e (490 mg, 1.57 mmol) was dissolved in ethanol (5.0 mL), and thionyl chloride (220 mg, 1.85 mmol) was added at 0° C. The mixture was stirred at room temperature for 1 h. The reaction mixture was concentrated under reduced pressure to give the crude title product 3f (390 mg, 102%). The crude product was directly used in the next step without being purified.

MS m/z (ESI): 208.1 [M+1].

Step 6

3-Isopropyl-6-(((1S)-1-(3-((tetrahydrofuran-3-yl)oxy)phenyl)ethyl)amino)-1,3,5-triazine-2,4(1H,3H)-dione 3

Compound 1c (150 mg, 0.68 mmol) and compound 3f (211 mg, 0.87 mmo) were dissolved in N-methylpyrrolidone (6 mL), and triethylamine (69 mg, 0.68 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 3 (40 mg, yield: 16.4%).

MS m/z (ESI): 361.0 [M+1].

$^1H$ NMR (500 MHz, DMSO-$d_6$) δ 10.45 (brs, 1H), 7.28-7.25 (m, 2H), 6.92-6.88 (m, 2H), 6.81 (m, 1H), 5.02-4.98 (m, 2H), 4.81 (m, 1H), 3.90-3.74 (m, 4H), 2.19 (m, 1H), 1.92 (m, 1H), 1.40 (d, 3H), 1.29 (d, 6H).

Example 4

(S)-3-Isopropyl-6-((1-(3-((6-methylpyridin-3-yl)oxy)phenyl)ethyl)amino)-1,3,5-triazine-2,4(1H,3H)-dione 4

4

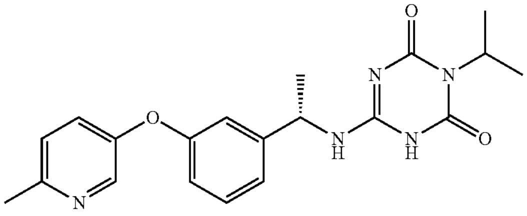

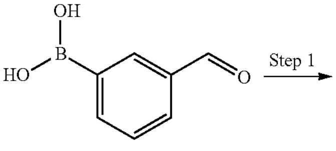

4a

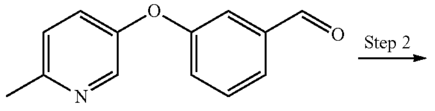

4b

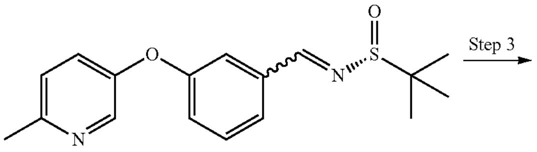

4c

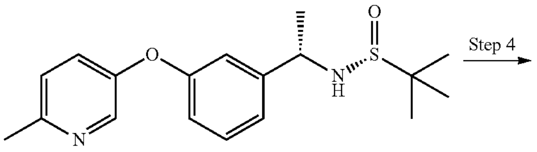

4d

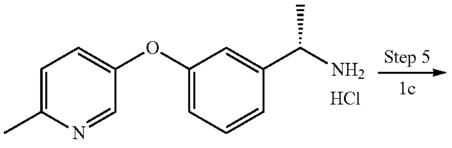

4e

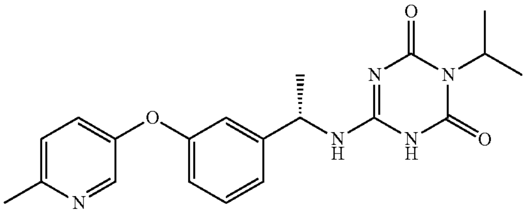

4

Step 1

3-((6-Methylpyridin-3-yl)oxy)benzaldehyde 4b (3-Formylphenyl)boronic acid 4a (800 mg, 5.34 mmol, Accela ChemBio Inc.) and 6-methylpyridin-3-ol (300 mg, 275 mmol, Bide Pharmatech Ltd.) were dissolved in dichloromethane (6.0 mL), and triethylamine (560 mg, 5.54 mmol), pyridine (440 mg, 5.56 mmol) and anhydrous copper acetate (1.0 g, 5.51 mmol, Bide Pharmatech Ltd.) were added. The reaction was stirred for 24 h. The reaction mixture was filtered through celite, and the filtrate was concentrated under reduced pressure. The resulting residue was purified by silica gel column chromatography with eluent system A to give the title product 4b (410 mg, yield: 69.9%).

MS m/z (ESI): 214.0 [M+1].

Step 2

(R)-2-Methyl-N-(3-((6-methylpyridin-3-yl)oxy)benzylidene)propane-2-sulfinamide 4c Compound 4b (410 mg, 1.92 mmol) and (R)-2-methylpropane-2-sulfinamide (235 mg, 1.94 mmol, adamas) were dissolved in dichloromethane (6 mL), and cesium carbonate (760 mg, 2.33 mmol) was added. The reaction was stirred for 16 h. The reaction mixture was filtered and concentrated under reduced pressure. The resulting residue was purified by silica gel column chromatography with eluent system A to give the title product 4c (560 mg, yield: 92.0%).

MS m/z (ESI): 317.1 [M+1].

Step 3

(R)-2-Methyl-N—((S)-1-(3-((6-methylpyridin-3-yl)oxy)phenyl)ethyl)propane-2-sulfinamide 4d Compound 4c (500 mg, 1.58 mmol) was dissolved in dichloromethane (10 mL). The reaction was cooled to −60° C. in a nitrogen atmosphere, and a 3 M solution of methylmagnesium bromide in 2-methyltetrahydrofuran (1.1 mL, 3.3 mmol, Shanghai Titan Scientific Co., Ltd.) was added dropwise. The reaction was warmed to room temperature and stirred for 16 h. A saturated aqueous ammonium chloride solution (20 mL) was added at 0° C., and the organic phase was separated. The aqueous phase was extracted with ethyl acetate (20 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system A to give the title product 4d (480 mg, yield: 91.3%).

MS m/z (ESI): 333.1[M+1].

Step 4

(S)-1-(3-((6-Methylpyridin-3-yl)oxy)phenyl)ethylamine hydrochloride 4e

Compound 4d (250 mg, 0.75 mmol) was dissolved in ethanol (6 mL). The solution was cooled to 0° C., and thionyl chloride (238 mg, 2.00 mmol, Shanghai Hushi Chemical Co., Ltd.) was added dropwise. The reaction was stirred at room temperature for 1 h. The reaction mixture was concentrated under reduced pressure to give the crude title product 4e (199 mg, yield: 99.9%). The crude product was directly used in the next step without being purified.

MS m/z (ESI): 229.0 [M+1].

Step 5

(S)-3-Isopropyl-6-((1-(3-((6-methylpyridin-3-yl)oxy)phenyl)ethyl)amino)-1,3,5-triazine-2,4(1H,3H)-dione 4

Compound 1c (129 mg, 0.58 mmol) and compound 4e (200 mg, 0.76 mmo) were dissolved in N-methylpyrrolidone (6 mL), and triethylamine (59 mg, 0.58 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 4 (4 mg, yield: 1.8%).

MS m/z (ESI): 382.0 [M+1].

$^1H$ NMR (500 MHz, DMSO-$d_6$) δ 10.46 (brs, 1H), 8.24 (s, 1H), 7.40-7.34 (m, 3H), 7.27 (m, 1H), 7.13 (m, 1H), 7.05 (s, 1H), 6.86 (m, 1H), 5.03 (m, 1H), 4.80 (m, 1H), 2.45 (s, 3H), 1.39 (d, 3H), 1.29 (d, 6H).

Example 5

(S)-3-Isopropyl-6-((1-(3-(trifluoromethoxy)phenyl)ethyl)amino)-1,3,5-triazine-2,4(1H,3H)-dione 5

5

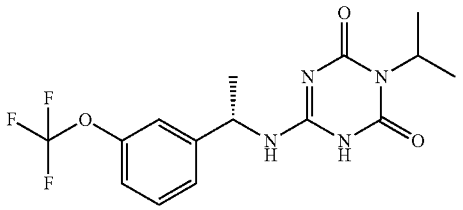

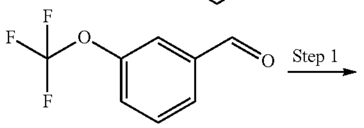

5a

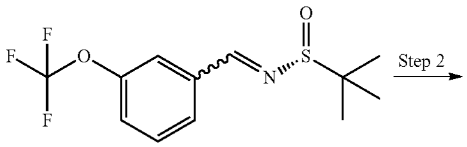

5b

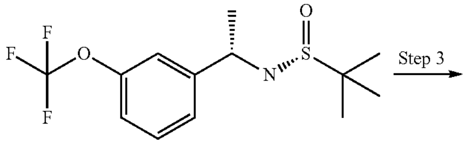

5c

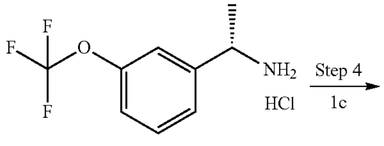

5d

-continued

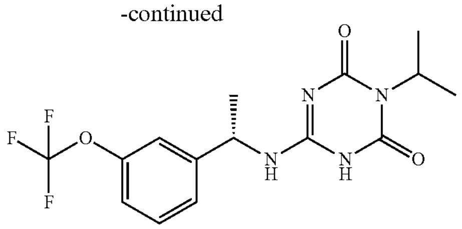

5

Step 1

(R)-2-Methyl-N-(3-(trifluoromethoxy)benzylidene) propane-2-sulfinamide 5b 3-(Tri fluoromethoxy)benzaldehyde 5a (1.0 g, 5.26 mmol, Bide Pharmatech Ltd.) and (R)-2-methylpropane-2-sulfinamide (640 mg, 5.28 mmol) were dissolved in dichloromethane (20 mL), and cesium carbonate (2.1 g, 6.44 mmol) was added. The reaction was stirred for 16 h. The reaction mixture was filtered and concentrated. The resulting residue was purified by silica gel column chromatography with eluent system A to give the title product 5b (1.45 g, yield: 94.0%).

MS m/z (ESI): 294.0 [M+1].

Step 2

(R)-2-Methyl-N—((S)-1-(3-(trifluoromethoxy)phenyl)ethyl)propane-2-sulfinamide 5c Compound 5b (500 mg, 1.70 mmol) was dissolved in dichloromethane (10 mL). The solution was cooled to −60° C. in a nitrogen atmosphere, and a 3 M solution of methylmagnesium bromide in 2-methyltetrahydrofuran (1.2 mL, 3.6 mmol) was added dropwise. The reaction was warmed to room temperature and stirred for 16 h. A saturated aqueous ammonium chloride solution (20 mL) was added at 0° C., and the organic phase was separated. The aqueous phase was extracted with ethyl acetate (20 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system A to give the title product 5c (490 mg, yield: 92.9%).

MS n/z (ESI): 310.0 [M+1].

Step 3

(S)-1-(3-(Trifluoromethoxy)phenyl)ethylamine hydrochloride 5d

Compound 5c (250 mg, 0.81 mmol) was dissolved in ethanol (10 mL). The solution was cooled to 0° C., and thionyl chloride (256 mg, 2.15 mmol, Shanghai Hushi Chemical Co., Ltd.) was added dropwise. The reaction was stirred at room temperature for 1 h. The reaction mixture was concentrated under reduced pressure to give the crude title product 5d (195 mg, yield: 99.9%). The crude product was directly used in the next step without being purified.

MS m/z (ESI): 188.8 [M−16].

Step 4

(S)-3-Isopropyl-6-((1-(3-(trifluoromethoxy)phenyl) ethyl)amino)-1,3,5-triazine-2,4(1H,3H)-dione 5

Compound 1c (119 mg, 0.54 mmol) and compound 5d (195 mg, 0.81 mmo) were dissolved in N-methylpyrrolidone (6 mL), and triethylamine (54 mg, 0.53 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 5 (30 mg, yield: 15.6%).

MS m/z (ESI): 359.0 [M+1].

$^1$H NMR (500 MHz, DMSO-$d_6$) δ 10.49 (brs, 1H), 7.68 (brs, 1H), 7.48 (m, 1H), 7.40-7.35 (m, 2H), 7.25 (m, 1H), 5.10 (m, 1H), 4.81 (m, 1H), 1.42 (d, 3H), 1.29 (d, 6H).

Example 6

(S)-6-((1-(5-Cyclopropyl-2-fluorophenyl)ethyl) amino)-3-isopropyl-1,3,5-triazine-2,4(1H,3H)-dione 6

6

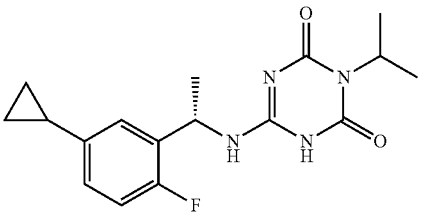

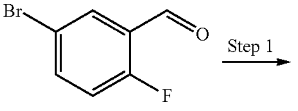

6a

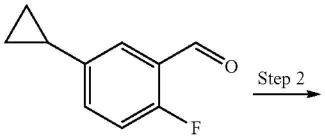

6b

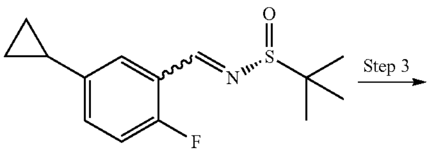

6c

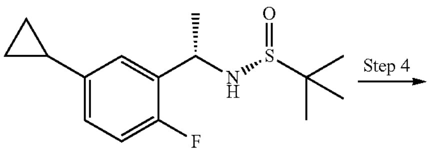

6d

-continued

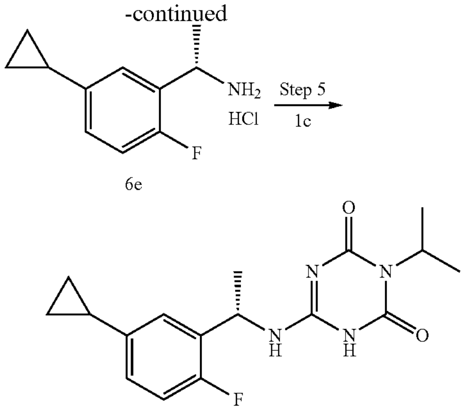

6e

6

Step 1

5-Cyclopropyl-2-fluorobenzaldehyde 6b

5-Bromo-2-fluorobenzaldehyde 6a (10.00 g, 49.26 mmol, Bide Pharmatech Ltd.) and cyclopropylboronic acid (6.35 g, 73.93 mmol, Accela ChemBio Inc.) were dissolved in 1,4-dioxane (100 mL) and water (5 mL), and [1,1'-bis(diphenylphosphino)ferrocene]dichloropalladium complexed with dichloromethane (2.42 g, 2.96 mmol) and tripotassium phosphate (27.15 g, 128.07 mmol) were added. The system was purged with nitrogen three times, and the mixture was stirred at 100° C. for 16 h, filtered, and concentrated under reduced pressure. The resulting residue was purified by silica gel column chromatography with eluent system A to give the title product 6b (7.00 g, yield: 86.6%).

$^1$H NMR (500 MHz, $CDCl_3$) δ 10.32 (s, 1H), 7.52 (m, 1H), 7.31 (m, 1H), 7.05 (m, 1H), 1.91 (m, 1H), 1.01-0.97 (m, 2H), 0.70-0.66 (m, 2H).

Step 2

(R)—N-(5-Cyclopropyl-2-fluorobenzylidene)-2-methylpropane-2-sulfinamide 6c

Compound 6b (1.00 g, 6.09 mmol) and (R)-2-methylpropane-2-sulfinamide (738 mg, 6.09 mmol, Bide Pharmatech Ltd.) were dissolved in dichloromethane (20 mL), and cesium carbonate (2.38 g, 7.30 mmol) was added. The reaction was stirred for 16 h. The reaction mixture was filtered and concentrated under reduced pressure to give the crude title product 6c (1.62 g, yield: 99.5%). The crude product was directly used in the next step without being purified.

MS m/z (ESI): 268.0 [M+1].

Step 3

(R)—N—((S)-1-(5-Cyclopropyl-2-fluorophenyl)ethyl)-2-methylpropane-2-sulfinamide 6d The crude compound 6c (1.62 g, 6.06 mmol) was dissolved in dichloromethane (10 mL), and the system was purged with nitrogen three times. The reaction was cooled to −60° C., and a 3 M solution of methylmagnesium bromide in 2-methyltetrahydrofuran (4.25 mL, 12.75 mmol, Shanghai Titan Scientific Co., Ltd.) was added dropwise. The reaction was stirred at room temperature for 5 h in a nitrogen atmosphere. A saturated ammonium chloride solution (10 mL) was added, and the organic phase was separated. The aqueous phase was extracted with ethyl acetate (40 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system B to give the title product 6d (1.70 g, yield: 99.0%).

MS m/z (ESI): 284.0 [M+1].

Step 4

(S)-1-(5-Cyclopropyl-2-fluorophenyl)ethylamine hydrochloride 6e

Compound 6d (300 mg, 1.06 mmol) was dissolved in ethanol (10 mL). The solution was cooled to 0° C., and thionyl chloride (335 mg, 2.82 mmol, Shanghai Hushi Chemical Co., Ltd.) was added dropwise. The reaction was stirred at room temperature for 1 h. The reaction mixture was concentrated under reduced pressure to give the crude title product 6e (228 mg, yield: 99.9%). The crude product was directly used in the next step without being purified.

MS m/z (ESI): 179.9 [M+1].

Step 5

(S)-6-((1-(5-Cyclopropyl-2-fluorophenyl)ethyl)amino)-3-isopropyl-1,3,5-triazine-2,4(1H,3H)-dione 6

Compound 1c (156 mg, 0.71 mmol) and compound 6e (190 mg, 0.88 mmo) were dissolved in N-methylpyrrolidone (8 mL), and triethylamine (71 mg, 0.71 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 6 (50 mg, yield: 21.3%).

MS m/z (ESI): 333.0 [M+1].

$^1$H NMR (500 MHz, DMSO-$d_6$) δ 10.48 (brs, R H), 7.20 (brs, 1H), 7.12 (m, 1H), 7.06 (m, 1H), 6.98 (m, 1H), 5.22 (m, 1H), 4.80 (m, 1H), 1.92 (m, 1H), 1.40 (d, 31H), 1.29 (d, 6H), 0.95-0.91 (m, 2H), 0.65-0.62 (in, 2H).

Example 7

(S)-6-((1-(Bicyclo[4.2.0]octan-1(6),2,4-trien-3-yl)ethyl)amino)-3-isopropyl-1,3,5-triazine-2,4(1H,3H)-dione 7

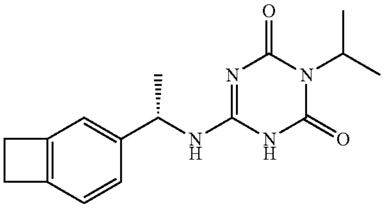

7

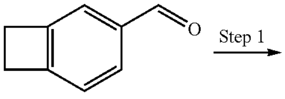

7a

-continued

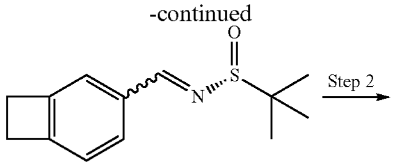

7b

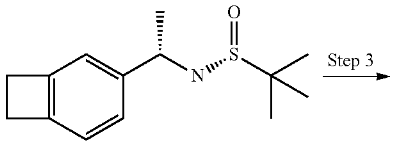

7c

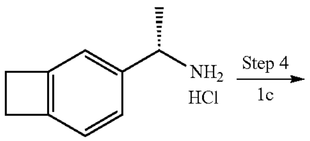

7d

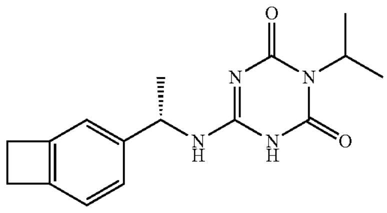

7

Step 1

(R)—N-(Bicyclo[4.2.0]oct-1(6),2,4-trien-3-ylmethylene)-2-methylpropane-2-sulfinamide 7b Bicyclo[4.2.0]octa-1(6),2,4-triene-3-carbaldehyde 7a (2.9 g, 22.0 mmol, prepared by "the method disclosed in step 1 on pp. 512-513 of the specification in the patent application WO2019023147A1") and (R)-2-methylpropane-2-sulfinamide (2.8 g, 23.0 mmol) were dissolved in dichloromethane (40 mL), and cesium carbonate (8.6 g, 26.4 mmol) was added. The reaction was stirred for 16 h. The reaction mixture was filtered, and the filtrate was concentrated under reduced pressure to give the crude title product 7b (5.7 g). The crude product was directly used in the next step without being purified.

MS m/z (ESI): 236.1 [M+1].

Step 2

(R)—N—((S)-1-(Bicyclo[4.2.0]oct-1(6),2,4-trien-3-yl)ethyl)-2-methylpropane-2-sulfinamide 7c To a solution of the crude compound 7b (2.8 g, 12.1 mmol) in anhydrous dichloromethane (80 mL), a 3 M solution of methylmagnesium bromide in methyltetrahydrofuran (8.1 mL, 24.2 mmol, Shanghai Titan Scientific Co., Ltd.) was added dropwise at −50° C. The mixture was reacted at room temperature for 16 h in a nitrogen atmosphere. A saturated aqueous ammonium chloride solution (50 mL) was added, and extraction was performed with dichloromethane (50 mL×2). The organic phases were combined, dried over anhydrous sodium sulfate, filtered, and concentrated under reduced pressure. The resulting residue was purified by silica gel column chromatography with eluent system A to give the title product 7c (2.0 g, yield: 66.2%).

MS m/z (ESI): 252.1 [M+1].

Step 3

(S)-1-(Bicyclo[4.2.0]octan-1(6),2,4-trien-3-yl)ethylamine hydrochloride 7d

Compound 7c (500.0 mg, 2.0 mmol) was dissolved in methanol (3 mL), and a 4 M solution of hydrogen chloride in 1,4-dioxane (2 mL) was added dropwise. The reaction was stirred for 1 h. The reaction mixture was concentrated under reduced pressure to give the crude title product 7d (366.0 mg). The crude product was directly used in the next step without being purified.

MS m/z (ESI): 131.1 [M−16].

Step 4

(S)-6-((1-(Bicyclo[4.2.0]octan-1(6),2,4-trien-3-yl)ethyl)amino)-3-isopropyl-1,3,5-triazine-2,4(1H,3H)-dione 7

Compound 1c (182 mg, 0.82 mmol) and compound 7d (182 mg, 0.99 mmo) were dissolved in N-methylpyrrolidone (6 mL), and triethylamine (83 mg, 0.82 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 7 (30 mg, yield: 12.1%).

MS m/z (ESI): 301.0 [M+1].

$^1$H NMR (500 MHz, DMSO-$d_6$) δ 10.46 (brs, 1H), 7.22 (brs, 1H), 7.15 (m, 1H), 7.10-7.01 (m, 2H), 4.96 (m, 1H), 4.80 (m, 1H), 3.14-3.08 (m, 4H), 1.39 (d, 3H), 1.29 (d, 6H).

Example 8

(S)-6-((1-(2,3-Dihydrobenzofuran-6-yl)ethyl)amino)-3-isopropyl-1,3,5-triazine-2,4(1H,3H)-dione 8

8

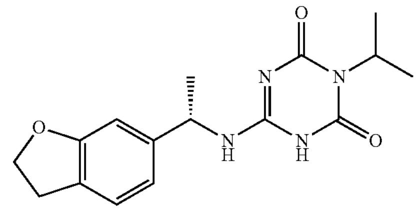

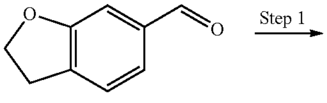

8a

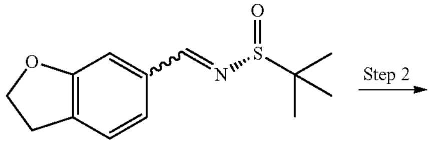

8b

-continued

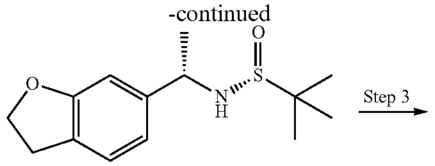

8c

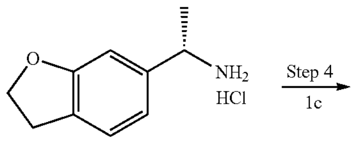

8d

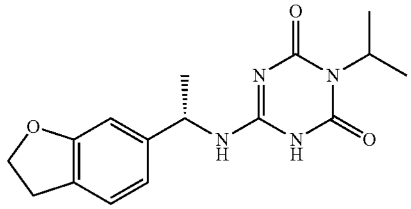

8

Step 1

(R)—N-((2,3-dihydrobenzofuran-6-yl)methylene)-2-methylpropane-2-sulfinamide 8b 2,3-Dihydrobenzofuran-6-carbaldehyde 8a (1.0 g, 6.8 mmol, Jiangsu Aikon Biopharmaceutical R&D Co., Ltd.) and (R)-2-methylpropane-2-sulfinamide (860.0 mg, 7.1 mmol, Shanghai Titan Scientific Co., Ltd.) were dissolved in dichloromethane (40 mL), and cesium carbonate (2.6 g, 8.1 mmol) was added. The reaction was stirred for 16 h. The reaction mixture was filtered, and the filtrate was concentrated under reduced pressure to give the crude title product 8b (1.8 g). The crude product was directly used in the next step without being purified.

MS m/z (ESI): 252.0 [M+1].

Step 2

(R)—N—((S)-1-(2,3-Dihydrobenzofuran-6-yl)ethyl)-2-methylpropane-2-sulfinamide 8c To a solution of the crude compound 8b (1.7 g, 6.8 mmol) in anhydrous dichloromethane (45 mL), a 3 M solution of methylmagnesium bromide in methyltetrahydrofuran (4.9 mL, 14.6 mmol) was added dropwise at −50° C. The mixture was reacted at room temperature for 16 h in a nitrogen atmosphere. A saturated aqueous ammonium chloride solution (30 mL) was added, and extraction was performed with dichloromethane (30 mL×2). The organic phases were combined, dried over anhydrous sodium sulfate, filtered, and concentrated under reduced pressure. The resulting residue was purified by silica gel column chromatography with eluent system A to give the title product 8c (1.6 g, yield: 90.6%).

MS m/z (ESI): 268.1 [M+1].

Step 3

(S)-1-(2,3-Dihydrobenzofuran-6-yl)ethylamine hydrochloride 8d

Compound 8c (534.0 mg, 2.0 mmol) was dissolved in methanol (3 mL), and a 4 M solution of hydrogen chloride in 1,4-dioxane (2 mL) was added dropwise. The reaction was stirred for 1 h. The reaction mixture was concentrated under reduced pressure to give the crude title product 8d (400.0 mg). The crude product was directly used in the next step without being purified.

MS m/z (ESI): 147.1 [M−16].

Step 4

(S)-6-((1-(2,3-Dihydrobenzofuran-6-yl)ethyl)amino)-3-isopropyl-1,3,5-triazine-2,4(1H,3H)-dione 8

Compound 1c (168 mg, 0.76 mmol) and compound 8d (186 mg, 0.93 mmo) were dissolved in N-methylpyrrolidone (8 mL), and triethylamine (77 mg, 0.76 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 8 (15 mg, yield: 6.2%).

MS m/z (ESI): 317.0 [M+1].

$^1$H NMR (500 MHz, DMSO-$d_6$) δ 10.45 (brs, 1H), 7.21-7.16 (m, 2H), 6.80-6.74 (m, 2H), 4.95 (m, 1H), 4.80 (m, 1H), 4.52-4.49 (m, 2H), 3.14-3.11 (m, 2H), 1.39 (d, 3H), 1.29 (d, 6H).

Example 9

(S)-6-((l-(2,3-Dihydro-1H-inden-5-yl)ethyl)amino)-3-isopropyl-1,3,5-triazine-2,4(1H,3H)-dione 9

9

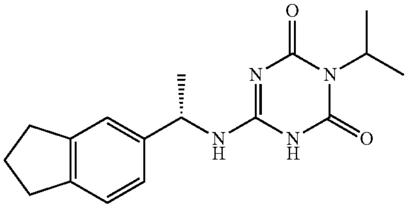

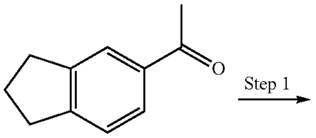

9a

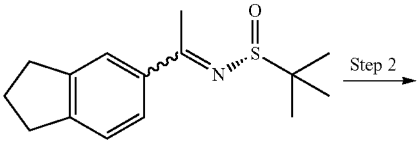

9b

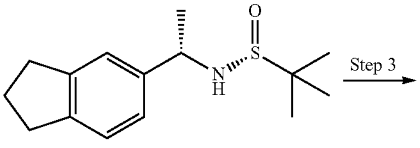

9c

-continued

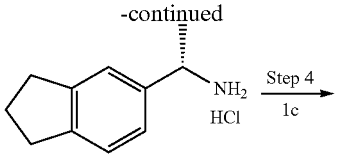

9d

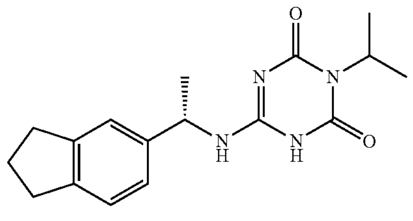

9

Step 1

(R)—N-(1-(2,3-Dihydro-1H-inden-5-yl)ethylidene)-2-methylpropane-2-sulfinamide 9b To a solution of 1-(2,3-dihydro-1H-inden-5-yl)ethan-1-one 9a (1.0 g, 6.3 mmol, TCI (Shanghai) Co., Ltd.) and (R)-2-methylpropane-2-sulfinamide (1.1 g, 8.8 mmol, Shanghai Titan Scientific Co., Ltd.) in anhydrous tetrahydrofuran (20 mL), a 1 M solution of chlorotriisopropoxytitanium in hexane (7.5 mL, 7.5 mmol, Shanghai Titan Scientific Co., Ltd.) was added. The reaction was stirred at 65° C. for 16 h. A saturated aqueous sodium bicarbonate solution (30 mL) was added, and extraction was performed with ethyl acetate (50 mL×2). The organic phases were combined, dried over anhydrous sodium sulfate, filtered, and concentrated under reduced pressure. The resulting residue was purified by silica gel column chromatography with eluent system A to give the title product 9b (570.0 mg, yield: 34.7%).

MS m/z (ESI): 264.0 [M+1].

Step 2

(R)—N—((S)-1-(2,3-Dihydro-1H-inden-5-yl)ethyl)-2-methylpropane-2-sulfinamide 9c

To compound 9b (570 mg, 2.2 mmol) in anhydrous tetrahydrofuran (10 mL), a 1 M solution of L-selectride in tetrahydrofuran (3.5 mL, 3.5 mmol, Shanghai Titan Scientific Co., Ltd.) was added dropwise at −78° C. The mixture was reacted at 0° C. for 1 h. A saturated aqueous ammonium chloride solution (20 mL) was added, and extraction was performed with ethyl acetate (30 mL×2). The organic phases were combined, dried over anhydrous sodium sulfate, filtered, and concentrated under reduced pressure to give the crude title product 9c (570 mg). The crude product was directly used in the next step without being purified.

MS m/z (ESI): 266.1 [M+1].

Step 3

(S)-1-(2,3-Dihydro-1H-inden-5-yl)ethylamine hydrochloride 9d

The crude compound 9c (570 mg, 2.2 mmol) was dissolved in methanol (3 mL), and a 4 M solution of hydrogen chloride in 1,4-dioxane (2 mL) was added dropwise. The reaction was stirred for 1 h. The reaction mixture was concentrated under reduced pressure to give the crude title product 9d (430.0 mg). The crude product was directly used in the next step without being purified.

MS m/z (ESI): 145.1 [M−16].

Step 4

(S)-6-((1-(2,3-Dihydro-1H-inden-5-yl)ethyl)amino)-3-isopropyl-1,3,5-triazine-2,4(1H,3H)-dione 9

Compound 1c (170 mg, 0.77 mmol) and compound 9d (186 mg, 0.94 mmo) were dissolved in N-methylpyrrolidone (8 mL), and triethylamine (78 mg, 0.77 mmol) was added. The mixture was stirred at 120° C. for 16 h and purified by high performance liquid chromatography (Boston Phlex C18 150×30 mm, 5 m; elution system: water (10 mmol of ammonium bicarbonate), acetonitrile, 20-95% acetonitrile; 20 min of gradient elution: flow rate: 30 mL/min) to give the title product 9 (30 mg, yield: 12.4%).

MS m/z (ESI): 315.0 [M+1].

$^1H$ NMR (500 MHz, DMSO-$d_6$) δ 10.45 (brs, 1H), 7.20-7.17 (m, 3H), 7.08 (m, 1H), 4.98 (m, 1H), 4.80 (m, 1H), 2.85-2.80 (m, 4H), 2.03-1.97 (m, 2H), 1.39 (d, 3H), 1.29 (d, 6H).

Example 10

(S)-3-Isopropyl-6-((1-(5,6,7,8-tetrahydronaphthalen-2-yl)ethyl)amino)-1,3,5-triazine-2,4(1H,3H)-dione 10

10

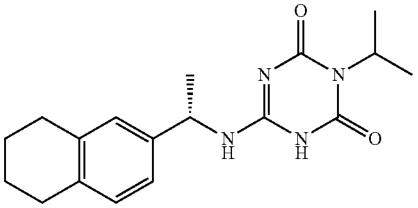

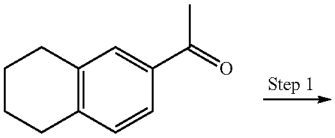

10a

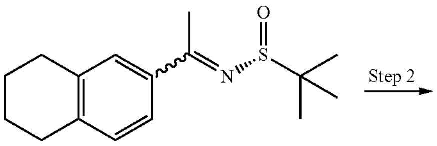

10b

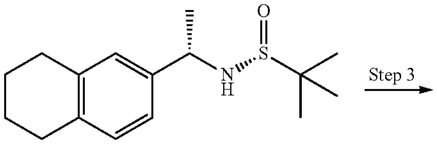

10c

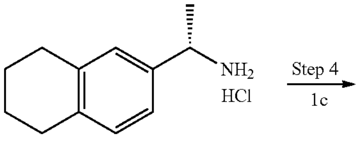

10d

-continued

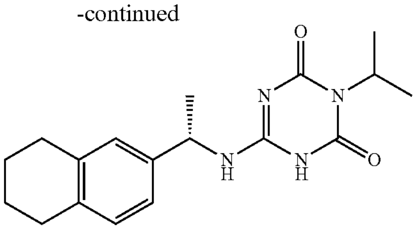

10

Step 1

(R)-2-Methyl-N-(1-(5,6,7,8-tetrahydronaphthalen-2-yl)ethylidene)propane-2-sulfinamide 10b To a solution of 1-(5,6,7,8-tetrahydronaphthalen-2-yl) ethan-1-one 10a (2.0 g, 11.5 mmol, Alfa Aesar (Tianjin) Chemical Co., Ltd.) and (R)-2-methylpropane-2-sulfinamide (2.1 g, 17.3 mmol, Shanghai Titan Scientific Co., Ltd.) in anhydrous tetrahydrofuran (20 mL), tetraethyl titanate (4.0 g, 17.3 mmol, Energy Chemical) was added. The reaction was stirred at 65° C. for 16 h. A saturated aqueous sodium bicarbonate solution (60 mL) was added, and extraction was performed with ethyl acetate (100 mL×2). The organic phases were combined, dried over anhydrous sodium sulfate, filtered, and concentrated under reduced pressure. The resulting residue was purified by silica gel column chromatography with eluent system A to give the title product 10b (2.6 g, yield: 81.6%).

MS m/z (ESI): 278.0 [M+1].

Step 2

(R)-2-Methyl-N—((S)-1-(5,6,7,8-tetrahydronaphthalen-2-yl)ethyl)propane-2-sulfinamide 10c Compound 10b (350 mg, 1.26 mmol) was dissolved in tetrahydrofuran (10 mL), and the system was purged with nitrogen three times. The reaction was cooled to −78° C., and a 1 M solution of L-selectride in tetrahydrofuran (2.02 mL, 2.02 mmol, Shanghai Titan Scientific Co., Ltd.) was added dropwise. The reaction was stirred at 0° C. for 1 h in a nitrogen atmosphere. A saturated ammonium chloride solution (10 mL) was added, and the organic phase was separated. The aqueous phase was extracted with ethyl acetate (40 mL×2). The organic phases were combined, washed with a saturated sodium chloride solution (100 mL), dried over anhydrous sodium sulfate, filtered, and concentrated under reduced pressure. The resulting residue was purified by silica gel column chromatography with eluent system B to give the title product 10c (340 mg, yield: 96.4%).

MS m/z (ESI): 280.0 [M+1].

Step 3

(S)-1-(5,6,7,8-Tetrahydronaphthalen-2-yl)ethylamine hydrochloride 10d

Compound 10c (340 mg, 1.22 mmol) was dissolved in ethanol (10 mL). The solution was cooled to 0° C., and thionyl chloride (290 mg, 2.43 mmol, Shanghai Hushi Chemical Co., Ltd.) was added dropwise. The reaction was stirred at room temperature for 1 h. The reaction mixture was concentrated under reduced pressure to give the crude title product 10d (257 mg, yield: 99.8%). The crude product was directly used in the next step without being purified.

MS m/z (ESI): 158.9 [M−16].

Step 4

(S)-3-Isopropyl-6-((1-(5,6,7,8-tetrahydronaphthalen-2-yl)ethyl)amino)-1,3,5-triazine-2,4(1H,3H)-dione 10

Compound 1c (271 mg, 1.23 mmol) and compound 10d (257 mg, 1.47 mmo) were dissolved in N-methylpyrrolidone (8 mL), and triethylamine (124 mg, 1.23 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 10 (40 mg, yield: 9.9%).

MS m/z (ESI): 329.0 [M+1].

$^1H$ NMR (500 MHz, DMSO-$d_6$) δ 10.48 (brs, 1H), 7.23 (brs, 1H), 7.04-6.99 (m, 3H), 4.94 (m, 1H), 4.80 (m, 1H), 2.71-2.63 (m, 4H), 1.75-1.69 (m, 4H), 1.37 (d, 3H), 1.29 (d, 6H).

Example 11

(S)-6-((1-(5-Fluoro-2,3-dihydrobenzofuran-6-yl)ethyl)amino)-3-isopropyl-1,3,5-triazine-2,4(1H,3H)-dione 11

11

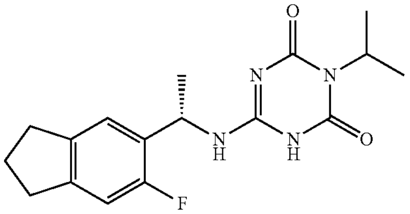

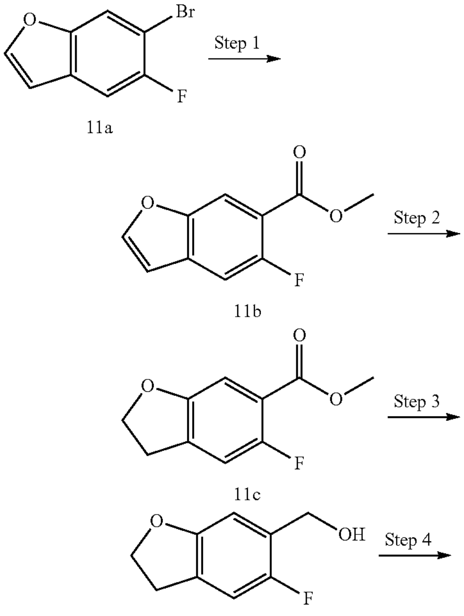

11a

11b

11c

11d

-continued

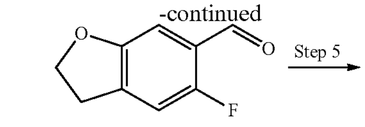

11e

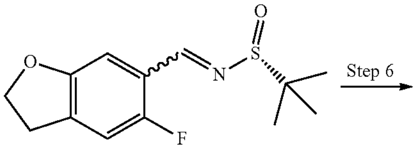

11f

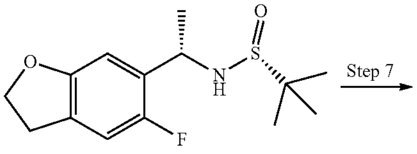

11g

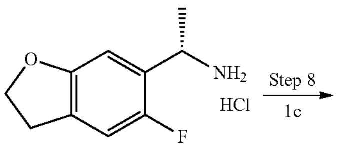

11h

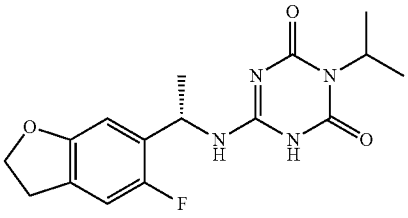

11

Step 1

Methyl 5-fluorobenzofuran-6-carboxylate 11b

6-Bromo-5-fluorobenzofuran 11a (3.20 g, 14.88 mmol, prepared by "the method of synthesizing intermediate A1.2b on page 36 of the specification in the patent application WO2017219948A1") was dissolved in methanol (50 mL), and [1,1'-bis(diphenylphosphino)ferrocene]dichloropalladium complexed with dichloromethane (1.26 g, 1.49 mmol) and N,N-diisopropylethylamine (3.01 g, 29.75 mmol) were added. The system was purged with carbon monoxide gas three times, and the reaction was stirred at 70° C. for 40 h. The reaction mixture was filtered and concentrated under reduced pressure. The resulting residue was purified by silica gel column chromatography with eluent system A to give the title product 11b (1.50 g, yield: 51.9%).

MS m/z (ESI): 194.8 [M+1].

Step 2

Methyl 5-fluoro-2,3-dihydrobenzofuran-6-carboxylate 11c

Compound 11b (1.50 g, 7.73 mmol) was dissolved in methanol (50 mL), and 10% palladium on carbon hydrogenation catalyst (wet) was added. The system was purged with hydrogen three times, and the reaction was stirred for 16 h. The reaction mixture was filtered and concentrated under reduced pressure. The resulting residue was purified by silica gel column chromatography with eluent system A to give the title product 11c (1.37 g, yield: 90.4%).

MS m/z (ESI): 196.8 [M+1].

Step 3

(5-Fluoro-2,3-dihydrobenzofuran-6-yl)methanol 11d

Compound 11c (1.37 g, 7.0 mmol) was dissolved in a tetrahydrofuran (30 mL) solution, and a 2 M solution of lithium borohydride in tetrahydrofuran (34.9 mL, 69.8 mmol) was added dropwise. The reaction was stirred at room temperature for 16 h. The reaction was quenched by addition of methanol (5 mL) in an ice bath, and the reaction mixture was adjusted to pH 6 with 1 M hydrochloric acid and extracted with ethyl acetate (30 mL×2). The organic phases were combined, dried over anhydrous sodium sulfate, filtered, and concentrated under reduced pressure. The resulting residue was purified by silica gel column chromatography with eluent system A to give the title product 11d (1.05 g, yield: 89.4%).

MS m/z (ESI): 190.0 [M+22].

Step 4

5-Fluoro-2,3-dihydrobenzofuran-6-carbaldehyde 11e

Compound 11d (1.05 g, 6.24 mmol) was dissolved in a dichloromethane (20 mL) solution, and Dess-Martin oxidant (3.97 g, 9.36 mmol) was added. The mixture was reacted at room temperature for 2 h. The reaction was quenched by addition of saturated sodium thiosulfate (20 mL) and saturated sodium bicarbonate (20 mL) in an ice bath, and extraction was performed with dichloromethane (30 mL×2). The organic phases were combined, dried over anhydrous sodium sulfate, filtered, and concentrated under reduced pressure. The resulting residue was purified by silica gel column chromatography with eluent system A to give the title product 11e (1.03 g, yield: 99.3%).

MS m/z (ESI): 167.0 [M+1].

Step 5

(R)—N-((5-Fluoro-2,3-dihydrobenzofuran-6-yl)methylene)-2-methylpropane-2-sulfinamide 11f Compound 11e (1.30 g, 7.82 mmol) and (R)-2-methylpropane-2-sulfinamide (1.42 g, 11.72 mmol, Bide Pharmatech Ltd.) were dissolved in dichloromethane (20 mL), and cesium carbonate (1.58 g, 14.09 mmol) was added. The reaction was stirred for 16 h. The reaction mixture was filtered, and the filtrate was concentrated under reduced pressure to give the crude title product 11f (2.80 g). The crude product was directly used in the next step without being purified.

MS m/z (ESI): 270.0 [M+1].

Step 6

(R)—N—((S)-1-(5-Fluoro-2,3-dihydrobenzofuran-6-yl)ethyl)-2-methylpropane-2-sulfinamide 11g To a solution of the crude compound 11f (2.80 g, 10.40 mmol) in anhydrous dichloromethane (45 mL), a 3 M solution of methylmagnesium bromide in methyltetrahydrofuran (6.93 mL, 20.79 mmol) was added dropwise at −50° C. The mixture was reacted at room temperature for 2 h in a nitrogen atmosphere. A saturated aqueous ammonium chloride solution (30 mL) was added, and extraction was performed with dichloromethane (30 mL×2). The organic phases were combined, dried over anhydrous sodium sulfate, filtered, concentrated under reduced pressure, and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 11g (1.50 g, yield: 50.56%).

MS m/z (ESI): 286.0 [M+1].

Step 7

(S)-1-(5-Fluoro-2,3-dihydrobenzofuran-6-yl)ethylamine hydrochloride 11h

Compound 11g (300 mg, 1.05 mmol) was dissolved in ethanol (10 mL), and thionyl chloride (250 mg, 2.10 mmol) was added dropwise. The reaction was stirred for 1 h. The reaction mixture was concentrated under reduced pressure to give the crude title product 11h (228 mg). The crude product was directly used in the next step without being purified.

MS m/z (ESI): 164.9 [M−16].

Step 8

(S)-6-((1-(5-Fluoro-2,3-dihydrobenzofuran-6-yl)ethyl)amino)-3-isopropyl-1,3,5-triazine-2,4(1H,3H)-dione 11

Compound 1c (232 mg, 1.05 mmol) and compound 11h (228 mg, 1.05 mmo) were dissolved in N-methylpyrrolidone (6 mL), and triethylamine (106 mg, 1.05 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 11 (90 mg, yield: 25.7%).

MS m/z (ESI): 334.9 [M+1].

$^1$H NMR (500 MHz, DMSO-$d_6$) δ 10.52 (brs, 1H), 7.28 (brs, 1H), 7.08 (d, 1H), 6.75 (m, 1H), 5.14 (m, 1H), 4.79 (m, 1H), 4.53-4.50 (m, 2H), 3.16-3.13 (m, 2H), 1.38-1.37 (d, 3H), 1.30-1.28 (d, 6H).

Example 12

(S)-6-((1-(2-Fluoro-5-((6-methylpyridin-3-yl)oxy)phenyl)ethyl)amino)-3-isopropyl-1,3,5-triazine-2,4(1H,3H)-dione 12

12

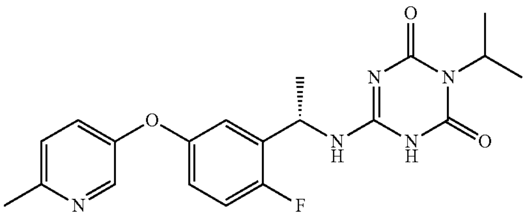

-continued

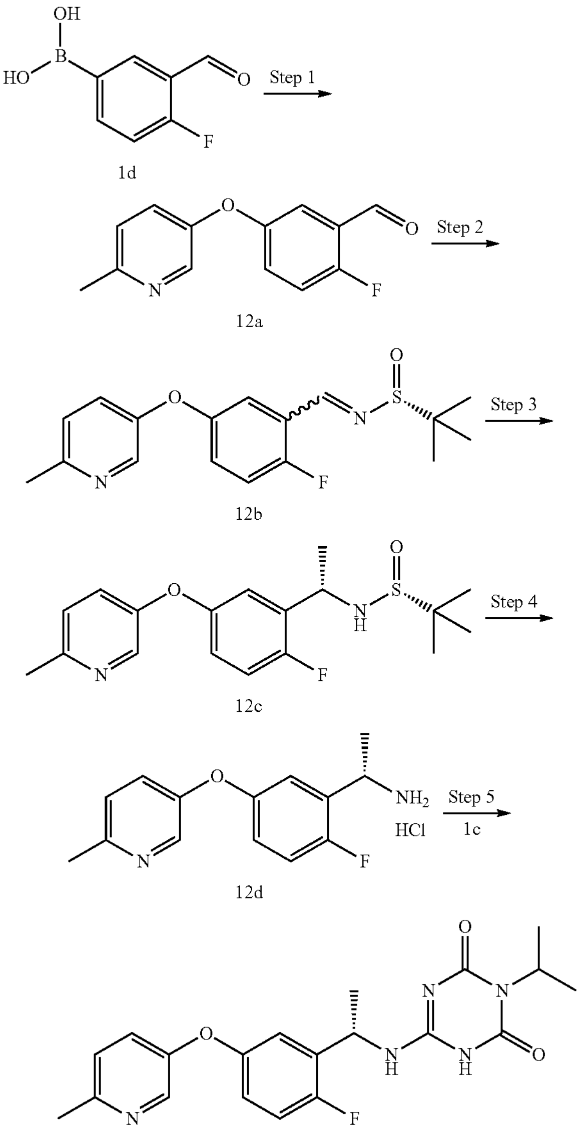

1d, 12a, 12b, 12c, 12d, 12

Step 1

2-Fluoro-5-((6-methylpyridin-3-yl)oxy)benzaldehyde 12a

Compound 1d (61.55 g, 363.25 mmol) and 6-methylpyridin-3-ol (20.00 g, 183.28 mmol, Bide Pharmatech Ltd.) were dissolved in dichloromethane (800 mL), and triethylamine (37.02 g, 366.53 mmol), pyridine (28.99 g, 366.50 mmol) and anhydrous copper acetate (66.58 g, 366.57 mmol, Bide Pharmatech Ltd.) were added. The reaction was stirred for 24 h. The reaction mixture was filtered through celite, and the filtrate was concentrated under reduced pressure. The resulting residue was purified by silica gel column chromatography with eluent system A to give the title product 12a (8.00 g, yield: 18.9%).

MS m/z (ESI): 231.9 [M+1].

Step 2

(R)—N-(2-Fluoro-5-((6-methylpyridin-3-yl)oxy) benzylidene)-2-methylpropane-2-sulfinamide 12b Compound 12a (8.00 g, 34.60 mmol) and (R)-2-methylpropane-2-sulfinamide (6.29 g, 51.90 mmol) were dissolved in dichloromethane (200 mL), and cesium carbonate (20.30 g, 62.27 mmol) was added. The reaction was stirred for 16 h. The reaction mixture was filtered and concentrated under reduced pressure. The resulting residue was purified by silica gel column chromatography with eluent system A to give the title product 12b (8.20 g, yield: 70.9%).

MS m/z (ESI): 334.9 [M+1].

Step 3

(R)—N—((S)-1-(2-Fluoro-5-((6-methylpyridin-3-yl) oxy)phenyl)ethyl)-2-methylpropane-2-sulfinamide 12c Compound 12b (8.20 g, 24.52 mmol) was dissolved in dichloromethane (100 mL). The reaction was cooled to −60° C. in a nitrogen atmosphere, and a 3 M solution of methylmagnesium bromide in 2-methyltetrahydrofuran (17.2 mL, 51.49 mmol, Shanghai Titan Scientific Co., Ltd.) was added dropwise. The reaction was warmed to room temperature and stirred for 5 h. A saturated aqueous ammonium chloride solution (100 mL) was added at 0° C., and the organic phase was separated. The aqueous phase was extracted with ethyl acetate (80 mL×2). The organic phases were combined, washed with a saturated sodium chloride solution (100 mL), dried over anhydrous sodium sulfate, filtered, concentrated under reduced pressure, and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 12c (2.10 g, yield: 24.4%).

MS m/z (ESI): 349.0[M−1].

Step 4

(S)-1-(2-Fluoro-5-((6-methylpyridin-3-yl)oxy)phenyl)ethylamine hydrochloride 12d Compound 12c (1.10 g, 3.14 mmol) was dissolved in ethanol (12 mL). The solution was cooled to 0° C., and thionyl chloride (747 mg, 6.28 mmol) was added dropwise. The reaction was stirred at room temperature for 1 h. The reaction mixture was concentrated under reduced pressure to give the crude title product 12d (887 mg, yield: 99.9%). The crude product was directly used in the next step without being purified.

MS m/z (ESI): 247.0 [M+1].

Step 5

(S)-6-((1-(2-Fluoro-5-((6-methylpyridin-3-yl)oxy) phenyl)ethyl)amino)-3-isopropyl-1,3,5-triazine-2,4 (1H,3H)-dione 12

Compound 1c (694 mg, 3.14 mmol) and compound 12d (887 mg, 3.14 mmo) were dissolved in N-methylpyrrolidone (12 mL), and triethylamine (317 mg, 3.13 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 12 (480 mg, yield: 38.3%). MS m/z (ESI): 399.9 [M+1].

$^1H$ NMR (500 MHz, DMSO-$d_6$) δ 10.53 (brs, 1H), 8.22 (d, 1H), 7.34-7.21 (m, 4H), 7.12 (m, 1H), 6.95 (m, 1H), 5.22 (m, 1H), 4.79 (m, 1H), 2.45 (s, 3H), 1.41 (d, 3H), 1.29 (d, 6H).

Example 13

(S)-6-((1-(2-Fluoro-5-methylphenyl)ethyl)amino)-3-isopropyl-1,3,5-triazine-2,4(1H,3H)-dione 13

13

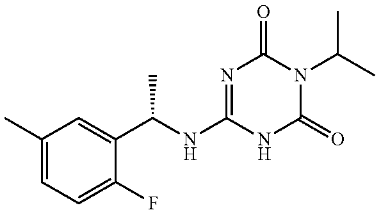

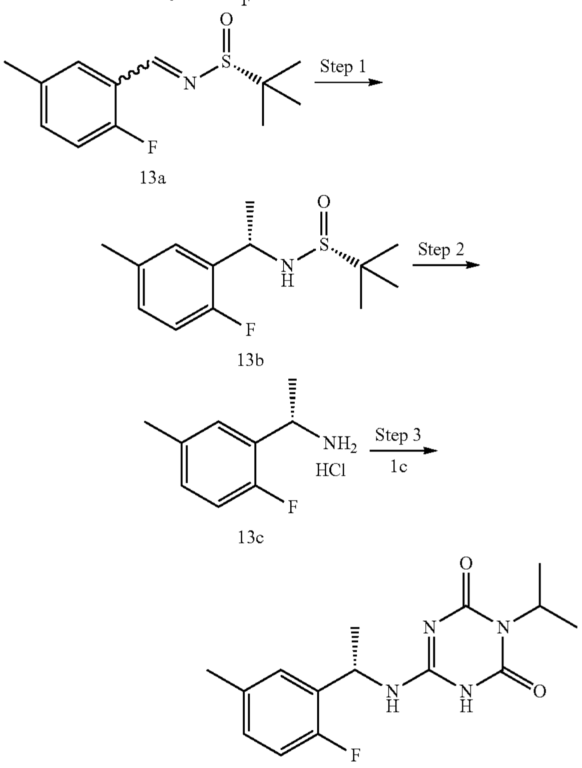

13a 13b 13c 13

Step 1

(R)—N—((S)-1-(2-Fluoro-5-methylphenyl)ethyl)-2-methylpropane-2-sulfinamide 13b (R)—N-(2-Fluoro-5-methylbenzylidene)-2-methylpropane-2-sulfinamide 13a (6.90 g, 28.59 mmol, prepared by "the method of synthesizing intermediate 3B on page 56 of the specification in the patent application WO2020092208A1") was dissolved in dichloromethane (100 mL), and the system was purged with nitrogen three times. The reaction was cooled to −60° C., and a 3 M solution of methylmagnesium bromide in 2-methyltetrahydrofuran (19.1 mL, 57.18 mmol) was added dropwise. The reaction was stirred at room temperature for 2 h in a nitrogen atmosphere. A saturated ammonium chloride solution (100 mL) was added, and the organic phase was separated. The aqueous phase was extracted with ethyl acetate (80 mL×2). The organic phases were combined, washed with a saturated sodium chloride solution (100 mL), dried over anhydrous sodium sulfate, filtered, concentrated under reduced pressure, and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 13b (5.60 g, yield: 76.1%).

MS m/z (ESI): 258.0 [M+1].

Step 2

(S)-1-(2-Fluoro-5-methylphenyl)ethylamine hydrochloride 13c

Compound 13b (670 mg, 2.60 mmol) was dissolved in ethanol (10 mL). The solution was cooled to 0° C., and thionyl chloride (620 mg, 5.21 mmol) was added dropwise. The reaction was stirred at room temperature for 1 h. The reaction mixture was concentrated under reduced pressure to give the crude title product 13c (493 mg, yield: 99.9%). The crude product was directly used in the next step without being purified.

MS m/z (ESI): 153.9 [M+1].

Step 3

(S)-6-((1-(2-Fluoro-5-methylphenyl)ethyl)amino)-3-isopropyl-1,3,5-triazine-2,4(1H,3H)-dione 13

Compound 1c (712 mg, 3.22 mmol) and compound 13c (493 mg, 2.60 mmo) were dissolved in N-methylpyrrolidone (10 mL), and triethylamine (326 mg, 3.22 mmol) was added. The mixture was stirred at 120° C. for 16 h and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 13 (400 mg, yield: 40.6%).

MS m/z (ESI): 306.9 [M+1].

$^1H$ NMR (500 MHz, DMSO-$d_6$) δ 10.42 (brs, 1H), 7.22-7.05 (m, 4H), 5.21 (m, 1H), 4.79 (m, 1H), 2.28 (s, 3H), 1.40 (d, 3H), 1.29 (d, 6H).

Example 14

(S)-6-((1-(2-Fluoro-5-((6-methylpyridin-3-yl)oxy)phenyl)ethyl)amino)-3-(tetrahydro-2H-pyran-4-yl)-1,3,5-triazine-2,4(1H,3H)-dione 14

14

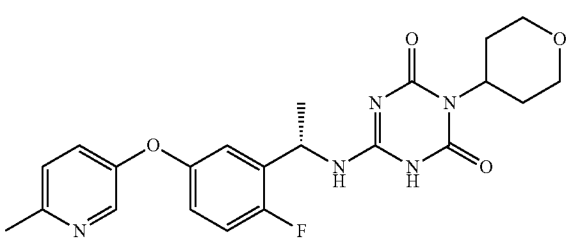

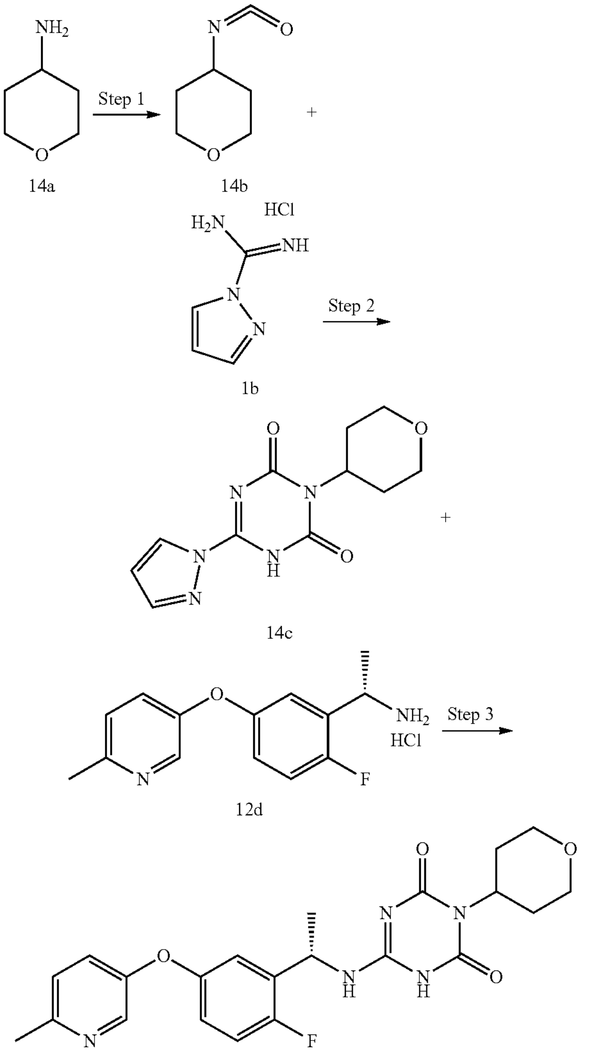

14a 14b 1b 14c 12d 14

Step 1

4-Isocyanatotetrahydro-2H-pyran 14b

To bis(trichloromethyl)carbonate (11.9 g, 40.0 mmol, Shanghai Titan Scientific Co., Ltd.) in anhydrous dichloromethane (30 mL), a solution of tetrahydro-2H-pyran-4-amine 14a (10.0 g, 100.0 mmol, Accela ChemBio Inc.) and N,N-diisopropylethylamine (28.4 g, 220.0 mmol, Shanghai Titan Scientific Co., Ltd.) in anhydrous dichloromethane (120 mL) was slowly added dropwise at 15° C. The mixture was reacted at room temperature for 2 h. The reaction mixture was concentrated under reduced pressure to give the crude title product 14b. The crude product was directly used in the next step without being purified.

Step 2

6-(1H-Pyrazol-1-yl)-3-(tetrahydro-2H-pyran-4-yl)-1,3,5-triazine-2,4(1H,3H)-dione 14c To a solution of compound 1b (10.5 g, 95.2 mmol) and the crude compound 14b in anhydrous N,N-dimethylacetamide (120 mL), 1,8-diazabicyclo[5.4.0]undec-7-ene (15.2 g, 100.0 mmol, Accela ChemBio Inc.) was slowly added dropwise at −10° C. The reaction was stirred at 0° C. for 1h. Subsequently, carbonyldiimidazole (23.2 g, 142.8 mmol, Bide Pharmatech Ltd.) and 1,8-diazabicyclo[5.4.0]undec-7-ene (21.7 g, 142.8 mmol, Accela ChemBio Inc.) were added to the reaction at 0° C. The reaction was stirred at 60° C. for 16 h. The reaction mixture was concentrated under reduced pressure, and dichloromethane was added to the resulting residue. The mixture was stirred and filtered, and the filter cake was collected and dried under reduced pressure to give the title product 14c (16.6 g, yield over two steps: 63.4%).

MS m/z (ESI): 264.1 [M+1].

Step 3

(S)-6-((1-(2-Fluoro-5-((6-methylpyridin-3-yl)oxy)phenyl)ethyl)amino)-3-(tetrahydro-2H-pyran-4-yl)-1,3,5-triazine-2,4(1H,3H)-dione 14

Compound 14c (148.3 mg, 0.7 mmol) and compound 12d (198.0 mg, 0.7 mmo) were dissolved in N-methylpyrrolidone (2 mL), and N,N-diisopropylethylamine (452.6 mg, 3.5 mmol) was added. The mixture was reacted in a microwave reactor at 140° C. for 2 h and purified by high performance liquid chromatography (Sharpsil-T Prep C18 5 μm 30×150 mm; elution system: water (10 mM ammonium bicarbonate), acetonitrile, acetonitrile was increased from 16% (v/v) to 36% (v/v) over 20 min, 30 mL/min; detection wavelengths: 214 & 254 nm) to give the title product 14 (95.0 mg, yield: 30.7%).

MS m/z (ESI): 442.1 [M+1].

$^1$H NMR (500 MHz, DMSO-$d_6$) δ 8.20 (s, 1H), 7.79 (brs, 1H), 7.30 (m, 1H), 7.23-7.19 (m, 2H), 7.14 (m, 1H), 6.92 (m, 1H), 5.26 (m, 1H), 4.66 (m, 1H), 3.87-3.83 (m, 2H), 3.32-3.25 (m, 3H), 2.51-2.44 (m, 3H), 2.41 (s, 31H), 1.42-1.33 (m, 4H).

Example 15

(S)-6-((1-(3-((6-Methylpyridin-3-yl)oxy)phenyl)ethyl)amino)-3-(tetrahydro-2H-pyran-4-yl)-1,3,5-triazine-2,4(1H,3H)-dione 15

15

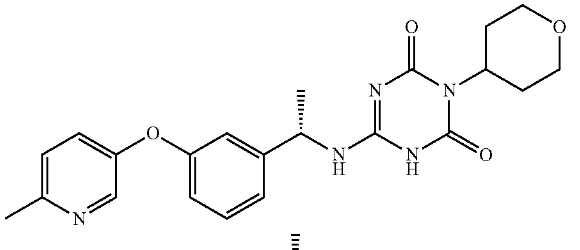

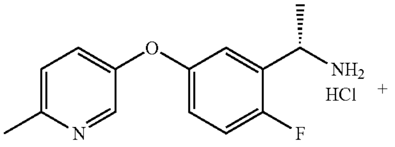

4e

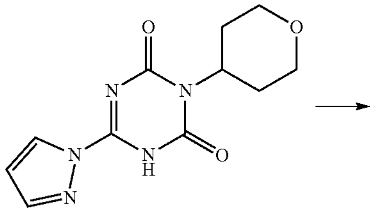

14c

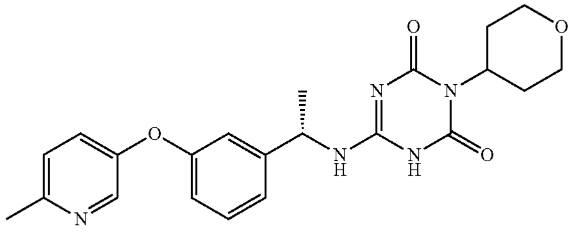

15

Compound 14c (337.0 mg, 1.3 mmol) and compound 4e (338.9 mg, 0.7 mmo) were dissolved in N-methylpyrrolidone (4 mL), and N,N-diisopropylethylamine (827.3 mg, 6.4 mmol) was added. The mixture was reacted in a microwave reactor at 140° C. for 2 h and purified by high performance liquid chromatography (Sharpsil-T Prep C18 5 μm 30×150 mm; elution system: water (10 mM ammonium bicarbonate), acetonitrile, acetonitrile was increased from 16% (v/v) to 36% (v/v) over 20 min, 30 mL/min; detection wavelengths: 214 & 254 nm) to give the title product 15 (166.0 mg, yield: 30.6%).

MS m/z(ESI):424.1 [M+1].

$^1$H NMR (500 MHz, DMSO-$d_6$) δ 8.24 (d, 1H), 7.66 (brs, 1H), 7.36-7.33 (m, 2H), 7.26 (d, 1H), 7.14 (d 1H), 7.05 (s, 1H), 6.85 (d 1H), 5.04 (m, 1H), 4.66 (m, 1H), 3.89-3.85 (m, 2H), 3.31-3.27 (m, 3H), 2.51-2.47 (m, 3H), 2.45 (s, 3H), 1.41-1.38 (m, 4H).

Example 16

(S)-6-((1-(2-Fluoro-5-methylphenyl)ethyl)amino)-3-(tetrahydro-2H-pyran-4-yl)-1,3,5-triazine-2,4(1H,3H)-dione 16

16

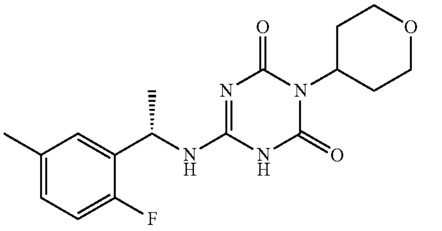

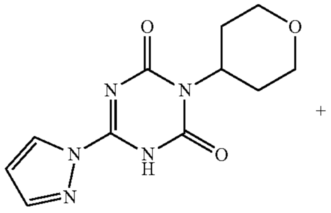

14c

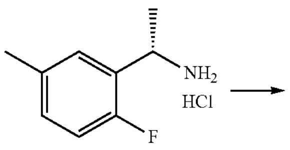

13c

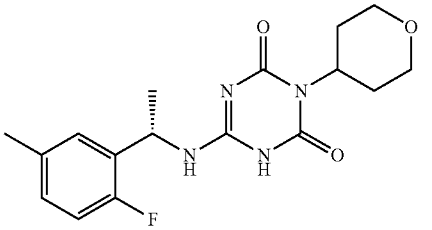

16

Compound 14c (425 mg, 1.61 mmol) and compound 13c (297 mg, 1.94 mmo) were dissolved in 1,4-dioxane (10 mL), and the reaction was stirred at 120° C. for 16 h. The reaction mixture was concentrated under reduced pressure and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 16 (310 mg, yield: 55.1%).

MS m/z (ESI): 349.0 [M+1].

$^1$H NMR (500 MHz, DMSO-$d_6$) δ 10.50 (brs, 1H), 7.28-7.05 (m, 4H), 5.22 (m, 1H), 4.64 (m, 1H), 3.90-3.86 (m, 2H), 3.33-3.27 (m, 2H), 2.54-2.42 (m, 2H), 2.28 (s, 3H), 1.45-1.39 (m, 5H).

Example 17

(S)-3-Cyclohexyl-6-((1-(2-fluoro-5-methylphenyl)ethyl)amino)-1,3,5-triazine-2,4(1H,3H)-dione 17

17

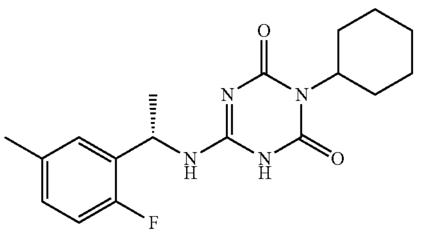

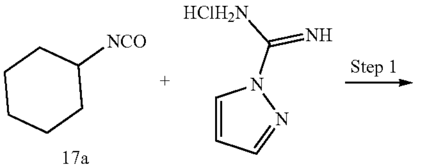

17a

1b

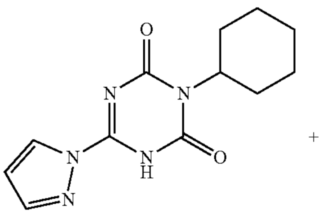

17b

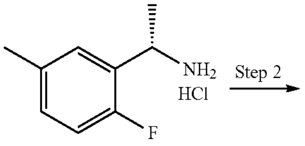

13c

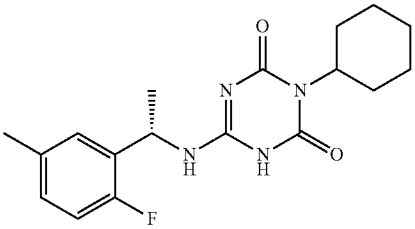

17

Step 1

3-Cyclohexyl-6-(1H-pyrazol-1-yl)-1,3,5-triazine-2,4(1H,3H)-dione 17b

Cyclohexyl isocyanate 17a (8.97 g, 71.66 mmol, Shanghai Titan Scientific Co., Ltd.) and compound 1b (10.00 g, 68.22 mmol) were dissolved in N,N-dimethylacetamide (50 mL). The reaction was cooled to −10° C., and 1,8-diazabicycloundec-7-ene (17.18 g, 68.22 mmol) was added dropwise over 5 min. The reaction was stirred in an ice bath for another 30 min. Subsequently, N,N'-carbonyldiimidazole (14.73 g, 102.33 mmol) was added under ice bath. The reaction was cooled to −5° C., and 1,8-diazabicycloundec- 7-ene (25.77 g, 102.33 mmol) was added dropwise over 10 min. The reaction was stirred in an ice bath for another 1h. 2 N hydrochloric acid (197 mL) was added dropwise at room temperature over 30 min. The mixture was filtered, and the filter cake was collected and dried in vacuo to give the title product 17b (16.00 g, yield: 89.8%).

MS m/z (ESI): 262.0 [M+1].

Step 2

(S)-3-Cyclohexyl-6-((1-(2-fluoro-5-methylphenyl) ethyl)amino)-1,3,5-triazine-2,4(1H,3H)-dione 17

Compound 17b (680 mg, 2.60 mmol) and compound 13c (392 mg, 2.56 mmo) were dissolved in 1,4-dioxane (10 mL), and the reaction was stirred at 120° C. for 16 h. The reaction mixture was concentrated to dryness and purified by high performance liquid chromatography (Boston Phlex C18 150×30 mm, 5 μm; elution system: water (10 mmol of ammonium bicarbonate), acetonitrile, 20-95% acetonitrile; 20 min of gradient elution; flow rate: 30 mL/min) to give the title product 17 (420 mg, yield: 46.6%).

MS m/z (ESI): 347.0 [M+1].

$^1$H NMR (500 MHz, DMSO-$d_6$) δ 10.45 (brs, 1H), 7.27-7.05 (m, 4H), 5.21 (m, 1H), 4.38 (m, 1H), 2.28 (s, 3H), 2.23-2.14 (m, 2H), 1.75-1.72 (m, 2H), 1.58 (m, 1H), 1.50-1.47 (m, 2H), 1.41-1.40 (d, 3H), 1.28-1.18 (m, 2H), 1.07 (m, 1H).

Biological Evaluation

The present disclosure is further described and explained below with reference to test examples, but these examples are not intended to limit the scope of the present disclosure.

Test Example 1: Inhibitory Effects of the Compounds Disclosed Herein on ATPase Activity of Myosin The method below was used to determine the inhibitory effects of the compounds disclosed herein on the ATPase activity of myosin, and the experimental method is briefly described below:

1. Materials and instruments

1. Myocardial actin (Cytoskeleton, AD99)
2. Myosin motor protein S 1 fragment (Cytoskeleton, CS-MYSO3)
3. ATP (Sigma, A7699-IG)
4. UltraPure™ 1 M Tris-HCl buffer, pH 7.5 (Thermo, 15567027)
5. CytoPhos™ phosphate assay biochem kit (Cytoskeleton, BK054)
6. Magnesium chloride solution (Sigma, 68475-100ML-F)
7. Potassium chloride solution (Sigma, 60142-100ML-F)
8. EGTA (Sigma, E3889-100G)
9. 96-well plate (Corning, 3697)
10. U-bottom 96-well plate (Corning, 3795)
11. Microplate reader (BMG, PHERAstar)
12. Constant-temperature incubator (BOXUN, SPX-100B-Z)

II. Procedures

Myocardial actin (1.61 μM) and myosin motor protein S 1 fragment (0.07 μM) were mixed with different concentrations of small-molecule compounds (initial concentration of 100 μM, serially diluted 3-fold to 9 concentrations), and the plate was incubated at 37° C. for 1 h. Then 120 μM ATP was added and the plate was incubated at 37° C. for 2 h. Finally, the assay solution in the CytoPhos™ phosphate assay biochem kit was added to each well (70 μL/well), and the plate was incubated at room temperature for 10 min. The OD readings at the wavelength of 650 nM were taken on a microplate reader. The Pi amount was calculated according to the standard curve. The data were processed using GraphPad software. An inhibition curve was plotted according to the compound concentrations and the corresponding inhibition rates, and the concentration at which the inhibition rate was 50%, i.e., the $IC_{50}$ value, was calculated. The experimental results are detailed in Table 1.

TABLE 1

The inhibitory activity of the compounds disclosed herein against myosin ATPase

| Example No. | $IC_{50}$(μM) |
|---|---|
| 1 | 2.41 |
| 2 | 2.55 |
| 3 | 5.11 |
| 4 | 1.66 |
| 5 | 1.98 |
| 6 | 0.45 |
| 7 | 1.33 |
| 8 | 3.75 |
| 9 | 0.68 |
| 10 | 0.62 |
| 11 | 1.39 |
| 12 | 0.81 |
| 13 | 1.00 |
| 14 | 0.35 |
| 15 | 1.13 |
| 16 | 1.06 |

Conclusion. The compounds disclosed herein have good inhibitory effects on myosin ATPase.

Test Example 2: Pharmacokinetic Evaluation of the Compound Disclosed Herein in Beagles 1. Abstract With beagles as test animals, the plasma concentrations of the test compounds were measured by LC/MS/MS at different time points after intragastric administration and intravenous injection. The pharmacokinetic performance of the compound disclosed herein was studied in beagles and its pharmacokinetic profile was evaluated.

2. Experimental Protocol 2.1. Experimental Compounds

The compound of Example 16, compound MYK-461

(MYK-461

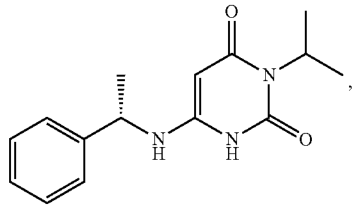

Example 1 of WO2014205223A1).

2.2. Experimental Animals

Pharmacokinetics of the compound of Example 16 in beagles: 8 beagles, an equal number of males and females, divided into 2 groups of 4, provided by Shanghai Medicilon Inc. Pharmacokinetics of compound MYK-461 in beagles: 6 beagles, male, divided into 2 groups of 3, provided by Shanghai Medicilon Inc.

2.3. Preparation of Compound Solutions

A certain amount of the compound of Example 16 was measured out, and 5% DMSO, 30% PG, 30% PEG400 and 35% normal saline were added to prepare a clear solution.

A certain amount of compound MYK-461 was measured out, and 5% DMSO, 20% PG, 20% PEG400 and 55% normal saline were added to prepare a clear solution.

2.4. Administration

Beagles were fasted overnight and then given compounds by intragastric administration and intravenous injection at doses of 2 mg/kg and 0.5 mg/kg, respectively, and at volumes of 5 mL/kg and 2 mL/kg, respectively.

3. Procedures 1.0-mL blood samples were collected from the jugular veins or forelimb veins of the animals in the intragastric administration group before administration and 0.25 h, 0.5 h, 1.0 h, 2.0 h, 4.0 h, 6.0 h, 8.0 h, 12.0 h and 24.0 h after administration, placed into EDTA-K2 anticoagulant tubes, and centrifuged at 10,000 rpm for 5 min (4° C.), and plasma was isolated within 1 h and stored at −80° C. before analysis. The blood collection to centrifugation process was performed under ice bath conditions. Three hours after administration, feeding was resumed.

Blood samples were collected from the animals in the intravenous injection group before administration and 5 min, 0.25 h, 0.5 h, 1.0 h, 2.0 h, 4.0 h, 8.0 h, 12.0 h and 24.0 h after administration and processed as in the intragastric administration group.

Determination of plasma concentrations in beagles after intragastric administration and intravenous injection of different concentrations of test compounds: 30 μL of beagle plasma at each time point post-dose was mixed with an internal standard solution (internal standard for the compound of Example 16: 100 ng/mL warfarin; internal standard for compound MYK-461: 100 ng/mL tolbutamide) and 300 μL of methanol; the mixture was vortexed for 1 min and centrifuged at 18,000 g for 7 min, and 200 μL of the supernatant was transferred to a 96-well plate; 1 μL of the supernatant was taken for LC/MS/MS analysis.

4. Pharmacokinetic Parameters

TABLE 2

The pharmacokinetic parameters of the compound disclosed herein in beagles

| Compound | Route of administration | Dose (mg/kg) | Plasma concentration Cmax (ng/mL) | Area under curve AUC (ng/mL*h) | Half-life $T_{1/2}$ (h) | Residence time MRT(h) | Clearance CL/F (mL/min/kg) | Apparent volume of distribution Vz/F (mL/kg) |
|---|---|---|---|---|---|---|---|---|
| Example 16 | Intravenous injection | 0.5 | 1077 | 716 | 5.6 | 7.5 | 10.4 | 5022 |
| | Intragastric administration | 2 | 1537 | 3102 | 7.5 | 9.5 | 9.26 | 6050 |
| MYK-461 | Intravenous injection | 0.5 | 215 | 1376 | 47.2 | 72.2 | 1.63 | 6308 |
| | Intragastric administration | 2 | 1437 | 8719 | 38.9 | 59.2 | 1.48 | 3897 |

Conclusion: The compound of Example 16 of the present disclosure demonstrated a good absorption profile in beagles. In addition, the compound of Example 16 of the present disclosure has a significantly shorter $T_{1/2}$. Compound MYK-461 has a longer $T_{1/2}$, so the accumulation is more serious clinically, and the clinical administration needs to be constantly adjusted, which increases the medication risk. Reducing $T_{1/2}$ can clinically reduce or prevent drug accumulation in the body, favoring the determination of dosages for patients and avoiding the risks posed by accumulation. It is clear that the compound of Example 16 of the present disclosure has significant pharmacokinetic advantages over compound MYK-461.

Test Example 3: Pharmacokinetic Evaluation of the Compound Disclosed Herein in Cynomolgus Monkeys I. Abstract With cynomolgus monkeys as test animals, the plasma concentrations of the test compounds were measured by LC/MS/MS at different time points after intragastric administration and intravenous injection. The pharmacokinetic performance of the compound disclosed herein was studied in cynomolgus monkeys and its pharmacokinetic profile was evaluated.

2. Experimental Protocol 2.1. Experimental Compounds

The compound of Example 16 and compound MYK-461.

2.2. Experimental Animals

Pharmacokinetics of the compound of Example 16 in cynomolgus monkeys: 8 cynomolgus monkeys, an equal number of males and females, divided into 2 groups of 4, provided by Shanghai Medicilon Inc.

Pharmacokinetics of compound MYK-461 in cynomolgus monkeys: 6 cynomolgus monkeys, male, divided into 2 groups of 3, provided by Shanghai Medicilon Inc.

2.3. Preparation of Compound Solutions

A certain amount of the compound of Example 16 was measured out, and 5% DMSO, 30% PG, 30% PEG400 and 35% normal saline were added to prepare a clear solution.

A certain amount of compound MYK-461 was measured out, and 5% DMSO, 20% PG, 20% PEG400 and 55% normal saline were added to prepare a clear solution.

2.4. Administration

Cynomolgus monkeys were fasted overnight and then given compounds by intragastric administration and intravenous injection at doses of 2 mg/kg and 0.5 mg/kg, respectively, and at volumes of 5 mL/kg and 2 mL/kg, respectively.

3. Procedures 1.0-mL blood samples were collected from the forelimb veins of the animals in the intragastric administration group before administration and 0.25 h, 0.5 h, 1h, 2 h, 4 h, 6 h, 8 h, 12 h and 24 h after administration, placed into EDTA-K2 anticoagulant tubes, and centrifuged at 10,000 rpm for 5 min (4° C.), and plasma was isolated within 1 h and stored at −80° C. before analysis. The blood collection to centrifugation process was performed under ice bath conditions. Three hours after administration, feeding was resumed, and ad libitum access to water was given.

Blood samples were collected from the animals in the intravenous injection group before administration and 5 min, 0.25 h, 0.5 h, 1.0 h, 2.0 h, 4.0 h, 8.0 h, 12.0 h and 24.0 h after administration and processed as in the intragastric administration group.

Determination of plasma concentrations in cynomolgus monkeys after intragastric administration and intravenous injection of different concentrations of test compounds: 20 μL of cynomolgus monkey plasma at each time point post-dose was mixed with an internal standard solution (internal standard for the compound of Example 16: 10 ng/mL verapamil; internal standard for compound MYK-461: 100 ng/mL camptothecin) and 400 μL of methanol; the mixture was vortexed for 1 min and centrifuged at 18,000 g for 7 min, and 200 μL of the supernatant was transferred to a 96-well plate: 2 μL of the supernatant was taken for LC/MS/MS analysis.

4. Pharmacokinetic Parameters

TABLE 3

The pharmacokinetic parameters of the compound disclosed herein in cynomolgus monkeys

| Compound | Route of administration | Dose (mg/kg) | Plasma concentration Cmax (ng/mL) | Area under curve AUC (ng/mL*h) | Half-life $T_{1/2}$ (h) | Residence time MRT (h) | Clearance CL/F (mL/min/kg) | Apparent volume of distribution Vz/F (mL/kg) |
|---|---|---|---|---|---|---|---|---|
| Example 16 | Intravenous injection | 0.5 | 1659 | 1022 | 5.6 | 6.8 | 7.46 | 3579 |
| | Intragastric administration | 2 | 553 | 2405 | 10.3 | 12.5 | 11.8 | 10263 |
| MYK-461 | Intravenous injection | 0.5 | 222 | 976 | 27.3 | 42.8 | 5.02 | 8203 |
| | Intragastric administration | 2 | 563 | 3521 | 78.3 | 114 | 2.34 | 11369 |

Conclusion: The compound of Example 16 of the present disclosure demonstrated a good absorption profile in cynomolgus monkeys. In addition, the compound of Example 16 of the present disclosure has a significantly shorter $T_{1/2}$. Compound MYK-461 has a longer $T_{1/2}$, so the accumulation is more serious clinically, and the clinical administration needs to be constantly adjusted, which increases the medication risk. Reducing $T_{1/2}$ can clinically reduce or prevent drug accumulation in the body, favoring the determination of dosages for patients and avoiding the risks posed by accumulation. It is clear that the compound of Example 16 of the present disclosure has significant pharmacokinetic advantages over compound MYK-461.

Test Example 4: Toxicokinetic Evaluation of 14-Day Repeated Intragastric Administration of the Compound Disclosed Herein to SD Rats 1. Abstract With SD rats as test animals, the plasma concentrations of the test compounds and the concentrations of the original forms of the compounds in the administration solutions were measured by LC/MS/MS at different time points after intragastric administration. The toxicokinetic performance of the compound disclosed herein was studied in SD rats and its toxicokinetic profile was evaluated.

2. Experimental Protocol 2.1 Test Compounds

The compound of Example 16 and compound MYK-461.

2.2. Experimental Animals

24 SD rats, an equal number of males and females, evenly divided into 6 groups of 4, an equal number of males and females in each group, provided by Vital River Laboratory Animal Technology Co., Ltd.

2.3. Preparation of Compound Solutions

A certain amount of the compound of Example 16 was measured out, and 15% PEG400 and 85% (10% TPGS+1% HPMC K100LV) were added to prepare a pale yellow homogenous suspension.

A certain amount of compound MYK-461 was measured out, and 0.5% MC was added to prepare a colorless clear solution.

2.4. Administration

The compound of Example 16 was intragastrically administered at doses of 5 mg/kg, 15 mg/kg and 30 mg/kg, at a volume of 10 mL/kg.

Compound MYK-461 was administered at doses of 0.5 mg/kg, 1.5 mg/kg and 3 mg/kg, at a volume of 10 mL/kg.

3. Procedures 0.2-mL blood samples were collected from the orbit 0.5 h, 1.0 h, 2.0 h, 4.0 h, 8.0 h and 24.0 h after administration on day 1, and before administration and 0.5 h, 1.0 h, 2.0 h, 4.0 h, 8.0 hi, 24.0 h after administration on day 7 and day 14, placed into EDTA-K2 anticoagulation tubes, and centrifuged at 10,000 rpm for 1 min (4° C.), and plasma was isolated within 1 h and stored at −20° C. before analysis. The blood collection to centrifugation process was performed under ice bath conditions. Two hours after administration, feeding was resumed.

Determination of plasma concentrations in SD rats after intragastric administration of different concentrations of test compounds: 20 μL of SD rat plasma at each time point post-dose was mixed with 50 μL of an internal standard solution (internal standard for the compound of Example 16: 100 ng/mL verapamil; internal standard for compound MYK-461: 100 ng(mL camptothecin) and 200 μL of acetonitrile; the mixture was vortexed for 5 min and centrifuged at 3700 rpm for 10 min, and 1 μL of the supernatant was taken for LC/MS/MS analysis.

4. Toxicokinetic Parameters

TABLE 4

The toxicokinetic parameters of the compound disclosed herein in SD rats

| Compound | Dose (mg/kg) | Date | Plasma concentration Cmax (ng/mL) | Area under curve AUC (ng/mL*h) | Half-life $T_{1/2}$ (h) | Residence time MRT(h) | Clearance CL/F (mL/min/kg) | Apparent volume of distribution Vz/F (mL/kg) |
|---|---|---|---|---|---|---|---|---|
| Example 16 | 5 | Day 1 | 5735 | 30026 | 4.8 | 5.0 | 3.06 | 1265 |
| | | Day 7 | 4473 | 28136 | 4.9 | 6.0 | 2.99 | 1279 |
| | | Day 14 | 4858 | 29780 | 5.1 | 6.2 | 2.80 | 1239 |
| | 15 | Day 1 | 16125 | 80443 | 5.1 | 5.4 | 3.08 | 1369 |
| | | Day 7 | 16800 | 70916 | 6.5 | 6.7 | 3.58 | 2129 |
| | | Day 14 | 14125 | 82906 | 5.6 | 6.4 | 2.98 | 1445 |
| | 30 | Day I | 18725 | 104640 | 5.6 | 6.4 | 4.72 | 2257 |
| | | Day 7 | 21550 | 120552 | 5.9 | 6.7 | 4.14 | 2146 |
| | | Day 14 | 20000 | 139432 | 5.6 | 6.9 | 3.52 | 1689 |
| MYK-461 | 0.5 | Day 1 | 40.2 | 491 | 13.3 | 19.0 | 12.9 | 13778 |
| | | Day 7 | 51.7 | 888 | 14.7 | 21.3 | 7.46 | 8412 |
| | | Day 14 | 89.3 | 1558 | 32.9 | 47.3 | 3.06 | 5861 |
| | 1.5 | Day 1 | 140 | 2577 | 19.1 | 28.2 | 6.39 | 9561 |
| | | Day 7 | 269 | 5181 | 20.5 | 30.2 | 3.58 | 4802 |
| | | Day 14 | 333 | 6320 | 26.2 | 38.5 | 2.57 | 5027 |
| | 3.0 | Day 1 | 297 | 5213 | 28.5 | 43.1 | 4.91 | 8931 |
| | | Day 7 | 628 | 12549 | 190 | 275 | 1.97 | 4355 |
| | | Day 14 | 767 | 15985 | 46.5 | 68.1 | 1.3 | 3802 |

Conclusion: The compound of Example 16 of the present disclosure did not show significant accumulation in SD rats after 14 days of repeated intragastric administration, while compound MYK-461 did, which increased the medication risk. It is clear that the compound of Example 16 of the present disclosure has significant toxicokinetic advantages over compound MYK-461.

Test Example 5: Identification of Reactive Metabolites of the Compound Disclosed Herein in Human Liver Microsomes The identification of reactive metabolites of the compound disclosed herein in human liver microsomes was carried out using the experimental method below:

I. Materials and Instruments

1. Phosphate-buffered saline (purchased from Shanghai Sangon)
2. NADPH (ACROS, A2646-71-1)
3. Human liver microsome (Corning Gentest, Cat No. 452161, Lot No. 905002)
4. Thermo UHPLC-Q-Exactive Orbitrap mass spectrometer (Thermo Fisher Scientific)
5. Acquity BEH $C_{18}$ column, 2.1×100 mm, 1.7 μm (Waters, USA)
6. Positive control compound (diclofenac).

II. Experimental Compounds

The compound of Example 16 and compound MYK-461.

III. Procedures

1. Preparation of test compound solutions: A proper amount of a test compound was precisely measured out and dissolved in a proper amount of DMSO. After the solution was well mixed, a 30 mM stock solution was obtained. A 10 mM stock solution was 10-fold diluted with 50% acetonitrile/water (v/v) to obtain a 3.0 mM working solution 1. The 3.0 mM working solution 1 was 10-fold diluted with PBS to obtain a 300 μM working solution 2, and the solution was stored at 4° C. before use.
2. Preparation of phosphate-buffered saline: Proper amounts of $K_2HPO_4$ and $KH_2PO_4$ were measured out and dissolved in 4 L of pure water to prepare a 100 mM buffer, and the pH was then adjusted with phosphoric acid or sodium hydroxide to 7.4.
3. Preparation of liver microsome solutions: Proper amounts of liver microsome stock solutions of various species (20 mg/mL) were measured out and diluted with the 100 mM phosphate-buffered saline (pH 7.4) to prepare 1.43 mg/mL microsome solutions.
4. Preparation of NADPH cofactor solution: Proper amounts of NADPH and magnesium chloride were measured out and dissolved in a proper amount of the 100 mM phosphate-buffered saline (pH 7.4) so the concentrations of NADPH and magnesium chloride were 10 mM and 30 mM, respectively, and the solutions were stored for later use.
5. Preparation of glutathione (GSH) solution: A proper amount of glutathione was measured out and dissolved in a proper amount of the 100 mM phosphate-buffered saline (pH 7.4) so the concentration of GSH was 50 mM, and the solution was stored for later use.
6. The incubation system is shown below:

| | |
|---|---|
| Liver microsomal protein concentration | 1 mg/mL |
| Species | Human |
| Test compound concentration | 30 μM |
| NADPH concentration | 1.0 mM |
| $MgCl_2$ concentration | 3.0 mM |
| GSH concentration | 5 mM |
| Incubation medium | 100 mM PBS |
| pH of system | 7.4 |
| Incubation temperature | 37° C. |
| Length of incubation | 60 min |

-continued

| | |
|---|---|
| Incubation volume | 200 μL |
| Positive control | Diclofenac (10 μM) |

To a 1.5 mL centrifuge tube, 20 μL of the 300 μM working solution 2 was precisely transferred and 140 μL of a 1.43 mg/mL liver microsome solution was then added so the concentration of liver microsomal protein in the incubation system was 1 mg/mL. After 20 μL of 10 mM NADPH solution and 20 μL of 50 mM GSH solution were added, the tube was placed into a 37° C. constant-temperature incubator for shaking incubation, and a timer was set. After 60 min of incubation, the incubated sample was taken out of the incubator, and 1000 μL of ice-cold acetonitrile solution was added. The reaction was stopped, and the sample was left to stand at room temperature for 10 min and then centrifuged at 12,000 rpm for 10 min. All the supernatant was transferred to a centrifuge tube and concentrated to dryness in vacuo at 37° C. The residue was reconstituted with 200 μL of 25% acetonitrile/water solution and centrifuged at 12,000 rpm for 10 min. The supernatant was transferred to a 96-well plate, and 5 μL of it was pipetted for LC/MS analysis. For a blank sample, 20 μL of PBS was added instead of working solution 2. For an NCF sample, 20 μL of PBS was added instead of GSH solution. Positive control diclofenac (10 μM) was tested in the same way as the test compound. The collected data were processed and analyzed using Xcalibur software. According to the exact molecular weight, tandem mass spectrometry fragments were analyzed to see if the compound disclosed herein would be metabolically activated to produce reactive metabolites.

TABLE 5

Identification of reactive metabolites of the compound disclosed herein in human liver microsomes

| Compound | Result |
|---|---|
| Example 16 | Negative |
| MYK-461 | Positive |

Conclusion: In the experiment, no glutathione (GSH) conjugate associated with the compound of Example 16 of the present disclosure was detected, but a GSH conjugate associated with compound MYK-461 was detected. Therefore, the compound of Example 16 of the present disclosure is safer than compound MYK-461.

The invention claimed is:

1. A compound that is:

16

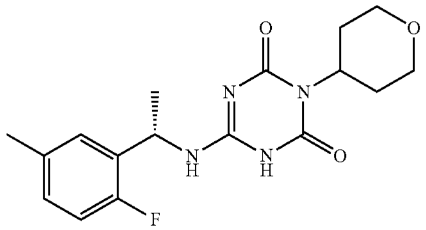

or a pharmaceutically acceptable salt thereof.

2. A pharmaceutical composition comprising the compound or the pharmaceutically acceptable salt thereof according to claim 1, and one or more pharmaceutically acceptable carriers, diluents or excipients.

* * * * *